US011111487B2

(12) United States Patent
Jovanovich et al.

(10) Patent No.: US 11,111,487 B2
(45) Date of Patent: Sep. 7, 2021

(54) METHOD AND APPARATUS FOR ENCODING CELLULAR SPATIAL POSITION INFORMATION

(71) Applicant: SILICON VALLEY SCIENTIFIC, INC., Livermore, CA (US)

(72) Inventors: Stevan B. Jovanovich, Livermore, CA (US); Peter Wagner, Menlo Park, CA (US)

(73) Assignee: SILICON VALLEY SCIENTIFIC, INC., Livermore, CA (US)

( * ) Notice: Subject to any disclaimer, the term of this patent is extended or adjusted under 35 U.S.C. 154(b) by 0 days.

(21) Appl. No.: 15/771,607

(22) PCT Filed: Oct. 27, 2016

(86) PCT No.: PCT/US2016/059232
§ 371 (c)(1),
(2) Date: Apr. 27, 2018

(87) PCT Pub. No.: WO2017/075293
PCT Pub. Date: May 4, 2017

(65) Prior Publication Data
US 2018/0305681 A1   Oct. 25, 2018

Related U.S. Application Data

(60) Provisional application No. 62/247,368, filed on Oct. 28, 2015.

(51) Int. Cl.
*C12N 15/10* (2006.01)
*C12Q 1/6806* (2018.01)

(52) U.S. Cl.
CPC ..... *C12N 15/1003* (2013.01); *C12N 15/1017* (2013.01); *C12N 15/1093* (2013.01); *C12Q 1/6806* (2013.01)

(58) Field of Classification Search
CPC ............ C12N 15/1003; C12N 15/1017; C12N 15/1093; C12Q 1/6806
See application file for complete search history.

(56) References Cited

U.S. PATENT DOCUMENTS

| | | |
|---|---|---|
| 5,234,809 A | 8/1993 | Boom et al. |
| 5,665,554 A | 9/1997 | Reeve et al. |
| 5,898,071 A | 4/1999 | Hawkins |
| 5,952,215 A | 9/1999 | Dwulet et al. |
| 6,190,616 B1 | 2/2001 | Jovanovich et al. |
| 6,534,262 B1 | 3/2003 | McKernan et al. |
| 6,551,839 B2 | 4/2003 | Jovanovich et al. |
| 7,244,961 B2 | 7/2007 | Jovanovich et al. |
| 8,288,106 B2 | 10/2012 | Fekete et al. |
| 8,536,322 B2 | 9/2013 | Han |
| 9,133,511 B2 | 9/2015 | Ju et al. |
| 9,371,598 B2 | 6/2016 | Chee |
| 2003/0170617 A1 | 9/2003 | Pasloske |
| 2008/0286161 A1* | 11/2008 | Heaney ............. B01L 3/502715 422/400 |
| 2010/0126286 A1* | 5/2010 | Self ........................ G01N 35/04 73/863.81 |
| 2011/0092376 A1* | 4/2011 | Colston, Jr. ........... B01F 3/0807 506/7 |
| 2012/0228142 A1* | 9/2012 | Sibbett ............. G01N 27/44765 204/627 |
| 2014/0066318 A1 | 3/2014 | Frisen et al. |
| 2014/0228255 A1* | 8/2014 | Hindson .............. C12Q 1/6874 506/26 |
| 2015/0148239 A1 | 5/2015 | Peter et al. |
| 2016/0253584 A1 | 9/2016 | Fodor et al. |

FOREIGN PATENT DOCUMENTS

| | | | |
|---|---|---|---|
| WO | 2012138926 A1 | 10/2012 | |
| WO | WO-2014135232 A1 * | 9/2014 | ........ B01L 3/502715 |
| WO | 2014210225 A1 | 12/2014 | |

OTHER PUBLICATIONS

Nature biotechnology 33.5 (2015): 503; 9 pages (Year: 2015).*
Crosetto, "Spatially resolved, transcriptomics and beyond", Nature Review Genetics, Jan. 1, 2015, pp. 57-66, Retrieved from the Internet: URL:http://www.nature.com/nrg/journal/v16/n1/pdf/nrg3832.pdf.
European Patent Office; "Extended European Search Report and European Search Opinion", dated Feb. 4, 2019, 7 pages.
ISA/US, International Search Report/Written Opinion for PCT/US16/59232 dated Mar. 2, 2017, 7 pages.
Je Hyuk Lee et al., "Fluorescent in situ sequencing (FISSEQ) of RNA for gene expression profiling in intact cells and tissues", Nature Protocols, vol. 10, No. 3, Feb. 12, 2015, p. 442-458.
K. H. Chen et la, "Spatially resolved, highly multiplexed RNA profiling in single cells", Science, vol. 348, No. 6233, Apr. 9, 2015, pp. aaa6090-1116090.

(Continued)

*Primary Examiner* — Sahana S Kaup
(74) *Attorney, Agent, or Firm* — Storella, P.C.

(57) ABSTRACT

A system, methods, and apparatus are described to collect and prepare single cells and groups of cells from microsamples of specimens and encode spatial information of the physical position of the cells in the specimen. In some embodiment, beads or surfaces with oligonucleotides containing spatial barcodes are used to analyze DNA or RNA. The spatial barcodes allow the position of the cell to be defined and the nucleic acid sequencing information, such as target sequencing, whole genome, gene expression, used to analyze the cells in a microsample for cell type, expression pattern, DNA sequence, and other information, in the context of the cell's physical position in the specimen. In other embodiment, markers such as isotopes are added to a microsample to encode spatial position with mass spectoscopy or other analysis. The spatial encoded information is then readout by analysis such as DNA sequencing, mass spectrometry, fluorescence, or other methods.

21 Claims, 27 Drawing Sheets

(56) References Cited

OTHER PUBLICATIONS

Kjetil Hodne et al> "Single-Cell Isolation and Gene Analysis: Pitfalls and Possibilities", International Journal of Molecular Sciences, vol. 16. No. 11, Nov. 10, 2015, pp. 26832-26849.
Macosko et al., Highly Parallel Genome-wide Expression Profiling of Individual Cells Using Nanoliter Droplets. Cell May 21, 2016 vol. 161 No. 5 pp. 1202-1214. Especially p. 1203 fig 1A; p. 1205 fig 2A, B.

\* cited by examiner

Encoding spatial information into DNA

Tissue or Specimen

Single Cell Spatial Analysis System

| | |
|---|---|
| Spatial Sampler | Collect cells and groups of cells in physical order in known order in microsamples from tissue or specimens |
| Spatial Encoder | Add paramagnetic beads with oligonucleotides with known spatial barcodes and targeted DNA capture regions to microsamples in known order to produce nanodroplets or boluses in known order with known barcodes |
| Spatial Librarian | Restriction or fragmentation<br>Capture genomic DNA from single cells onto single beads<br>DNA polymerase or ligase incorporates spatial and other barcodes into DNA<br>((N)NGS library preparation |

(N)NGS sequencing and bioinformatics

| | |
|---|---|
| Spatial Analysis | Decode Spatial barcode from DNA and cell and molecular barcodes to identify 3-D position within tissue of single cells and their genetic profiles |

Spatial information correlated with cell type and genetic profile and/or DNA sequence analysis and/or imaging with (N)NGS analysis

*FIG. 22*

Encoding spatial information into DNA with targeted capture
Tissue or Specimen

Single Cell Spatial Analysis System

| | |
|---|---|
| Spatial Sampler | Collect cells and groups of cells in physical order in known order in microsamples from tissue or specimens |

| | |
|---|---|
| Spatial Encoder | Add paramagnetic beads with oligonucleotides with known spatial barcodes and targeted DNA capture regions to microsamples in known order to produce nanodroplets or boluses in known order with known barcodes |

| | |
|---|---|
| Spatial Librarian | Restriction or fragmentation<br>Capture target DNA from single cells onto single beads<br>DNA polymerase or ligase incorporates spatial and other barcodes into DNA<br>((N)NGS library preparation |

(N)NGS sequencing and bioinformatics

| | |
|---|---|
| Spatial Analysis | Decode Spatial barcode from DNA and cell and molecular barcodes to identify 3-D position within tissue of single cells and their genetic profiles |

Spatial information correlated with cell type and genetic profile and/or DNA sequence analysis and/or imaging with (N)NGS analysis

*FIG. 23*

METHOD AND APPARATUS FOR ENCODING CELLULAR SPATIAL POSITION INFORMATION

CROSS REFERENCE TO RELATED APPLICATIONS (IF ANY)

This application claims the benefit of the priority date of provisional patent application 62/247,368, filed Oct. 28, 2015 (Jovanovich and Wagner, "Method and apparatus for encoding cellular spatial position information"), the contents of which are incorporated herein in their entirety.

STATEMENT OF FEDERALLY SPONSORED RESEARCH OR DEVELOPMENT (IF ANY)

None.

THE NAMES OF THE PARTIES TO A JOINT RESEARCH AGREEMENT IF THE CLAIMED INVENTION WAS MADE AS A RESULT OF ACTIVITIES WITHIN THE SCOPE OF A JOINT RESEARCH AGREEMENT

None.

REFERENCE TO A "SEQUENCE LISTING"

None.

BACKGROUND OF THE INVENTION

Analysis of single cells and groups of cells is now beginning to provide information to dissect and understand how cells function individually and unprecedented insight into the range of individual responses aggregated in ensemble measurements. Single cell methods for electrophysiology, flow cytometry, imaging, mass spectrometry (Lanni, E. J., et. al. J Am Soc Mass Spectrom. 2014; 25(11):1897-907.), microarray (Wang L and K A Janes. Nat Protoc. 2013; 8(2):282-301.), and Next Generation Sequencing (NGS) (Saliba A. E., et. al. Nucleic Acids Res. 2014; 42(14):8845-60.) have been developed and are driving an increased understanding of fundamental cellular processes, functions, and interconnected networks. As the individual processes and functions are understood and differentiated from ensemble measurements, the individual information can in turn lead to discovery of how network processes among cells operate. The networks may be in tissues, organs, multicellular organisms, symbionts, biofilms, surfaces, environments, or anywhere cells interact.

Next Generation Sequencing (NGS) of single cells is rapidly changing the state of knowledge of cells and tissue, discovering new cell types, and increasing understanding of the diversity of how cells and tissue function. Single cell NGS RNA sequencing (Saliba A. E., et. al., Nucleic Acids Res. 2014; 42(14):8845-60.) (Shapiro E. et. al., Nat Rev Genet. 2013; 14(9):618-30.) is unveiling the complexity of cellular expression, and the heterogenity from cell to cell, and from cell type to cell type (Buettner F. et. al., Nat Biotechnol. 2015; 33(2):155-60.). In situ sequencing (Ke R et. al., Nat Methods. 2013; 10(9):857-60.), (Lee J H, et. al., Nat Protoc. 2015; 10(3):442-58.) (Lee J H, et. al., Science. 2014, 21; 343(6177):1360-3.) has shown the feasability of directly sequencing of fixed cells. However, for RNA, many fewer reads are generated with in situ sequencing, biasing against detection of low abundant transcripts. Photoactivatable tags have been used to capture mRNA from single cells (Lovatt D et. al., Nat Methods. 2014; 11(2):190-6.) from known location in tissue, albeit with low throughput capture and manual cell collection.

Single cell nucleic acid sequencing technology and methods using NGS and Next Next Generation Sequencing (NNGS) are rapidly evolving. Common components are incorporation of a marker or barcode for each cell and molecule, reverse transcriptase for RNA sequencing, amplification, and pooling of sample for NGS and NNGS (collectively termed (N)NGS) library preparation and analysis. Starting with isolated single cells in wells, barcodes for individual cells and molecules have been incorporated by reverse transcriptase template switching before pooling and PCR amplification (Islam S. et. al. Genome Res. 2011; 21(7):1160-7.) (Ramsköld D. et. al. Nat Biotechnol. 2012; 30(8):777-82.) or on a barcoded poly-T primer with linear amplification (Hashimshony T. et. al. Cell Rep. 2012 Sep. 27; 2(3):666-73.) and unique molecular identifiers (Jaitin D. A. et. al. Science. 2014; 343(6172):776-9.).

Recent pioneering work has used the power of nanodroplets to perform highly parallel processing of mRNA from single cells with reverse transciption incorporating cell and molecular barcodes from freed primers (inDrop) (Klein A. M. et. al. Cell. 2015; 161(5):1187-201.) or primers attached to paramagnetic beads (DropSeq) (Macosko E. Z. et. al. Cell. 2015; 161(5):1202-14.). Both inDrop and DropSeq represent scalable approaches that will change the scale from 100s of cells previously analyzed to 1,000s and more. However, neither method encodes where in the physical three dimensional (3D) tissue the cell originated and what cells were in that microenvironment.

In the future, the spatial position of each individual cell (or groups of cells in a microenvironment) and what the state of individual cell(s) is, i.e., DNA sequence, DNA modifications, RNA splicing, RNA modifications, RNA expression pattern, proteome, metabolome, etc., will further the understanding of how tissue functions, how the diversity of cells and the heterogeneity affects human health, including cancer formation and progression, how the microbiome interacts with the host, cell and tissue response to stimuli including therapeutic agents (Crosetto N. et. al. Nat Rev Genet. 2015; 16(1):57-66.), and how cells interact in the environment among other fundamental questions.

BRIEF SUMMARY OF THE INVENTION

Disclosed herein is a Single Cell Spatial Analysis System™ 100 that encodes the information of the spatial position 130 where a microsample 125 was collected from tissue or from a specimen 301 for single cell sequencing, proteomics, cellular analysis, metabolomics and other analysis modalities. The Single Cell Spatial Analysis System 100 will give researchers, clinicians, forensic scientists, and many other applications and disciplines, a fundamental new capability to understand how single cells function, combining two and three dimensional spatial information with gene expression, and/or sequencing information, cellular response to chemical/enviromental challenges, protein expression, and other analysis methods.

The Spatial Subsystem (also referred to herein as the "Spatial Preparation Subsystem" or "Spatial Preparation System" or "Spatial Preparation Module") 200, which collects microsamples 125, is an automated approach to collecting and generating single cells or groups of cells from microsamples 125 from matrices such as tissue without painstaking, lower throughput, or labor intensive manipulations, e.g., Laser Capture Microdissection (Datta S. et. al. Histol Histopathol. 2015 Apr. 20: 11622.), manual pipette collection (Morris J. et. al. 2011. *J. Vis. Exp.* (50), e2634,) (Kajiyama T. et. al. Plant Cell Physiol. 2015; 56(7):1320-8.), or Fluidigm's low throughput C1 system (https://www.fluidigm.com/products/c1-system). Compared to in situ sequencing, the Single Cell Spatial Analysis System allows the full power of current commercially available (N)NGS systems to be used for the analysis engine.

The Single Cell Spatial Analysis System can encode the position of where the microsample 125 was located in the tissue or specimen 301 by different methods for different analyses. For genomic analysis, the Single Cell Spatial Analysis System 100 can use primer sets with nucleic acid barcodes for spatial position attached to beads or other surfaces such as flow cells to encode the spatial position 130 into DNA. For proteomic analysis by mass spectrometry, isotopes or other markers can be added to the microsamples 125 to encode the position while for enzyme activity assays fluorescent, Raman, optical, or other markers can be added to encode the spatial position 130. For metabolomic analysis, isotopes, fluorescent, or other markers can be added.

This approach of encoding into the microsample 125 where it originated in three dimensions from the specimen 301 is a fundamentally new approach to prepare samples from single cells and to understand the genetics, gene and protein regulation, metabolism of individual cells, how they function in a 3D tissue or biofilm structure, and what cell types, including rare cells, are present and where among other scientific, clinical, and applied information.

The Single Cell Spatial Analysis System 100 described can input raw, unprocessed samples, or other primary or secondary samples, and for genomic analysis produce either cDNA or prepared DNA libraries ready for DNA sequencing. The Single Cell Spatial Analysis System 100 for genomic assays has additional advantages over existing technology. Automated preparation of samples for NGS typically starts with purified bulk DNA or RNA and only part of the workflow is integrated, such as library preparation with manual steps of QC and post-library preparation amplification if needed. Automated sample preparation has not yet been integrated from raw samples, such as blood, tissue samples, fine needle aspirates, and other samples, to libraries ready for sequencing and remains largely manual. No automated NGS library preparation systems have yet been commercialized for single cells or for researchers and clinicians to routinely sequence cells from tissue. No system currently exists that collects single cells with positional information for nucleic acid analysis, or performs high throughput single cell RNA-Seq, or processes raw samples to libraries.

Disclosed herein is a system that can integrate one or more of the overall steps to take samples from specimens (i.e., tissue, biofilms, and other multi-dimensional matrices with cells or viruses) and prepare single cells, groups of cells, or cells and viruses (collectively or individually referred to as cells) to produce samples with information encoded about the cell's spatial positions in the original specimen. The cell's spatial position in the original specimen can be encoded in a marker, e.g., a spatial barcode, which is added to the specimen, a subregion, a microsample, or other part of a specimen, in a manner that encodes the single cell's position into the cell or components of the cell. Alternatively, the spatial position can be encoded by physical position of the sample as it is readout from a flow cell for NGS.

An instance of a spatial barcode for nucleic acids is described and one embodiment illustrated in detail. Microsamples from a subregion of a specimen are collected in physical order, such as a raster pattern or by rows or columns, and the microsamples placed in a known order into a fluidic stream or fixed wells or onto a surface. The term "microsample" is used to mean the smallest portion of the specimen that is collected as an individual sample that will be encoded with a single spatial marker or barcode and is the smallest unit sampled from the specimen by the system; microsamples may contain single cells to groups of cells. Single cells can be produced from the microsamples in microdrops, e.g., nanodroplets or boluses generated with a paramagnetic bead which has an attached oligonucleotide with a unique spatial DNA barcode, a type of spatial barcode, for the microsample. The beads with known unique spatial DNA barcodes are added in known order to the microsamples, which thereby will encode the order of the microsamples and cells in the microsamples and produce spatially encoded single cells. Additional barcodes may be unique for each cell or molecule or have quality control or other information. Nucleic acid is released from the single cell inside the nanodroplet or bolus and enzymology used to attach the oligonucleotide containing the spatial barcode to the cellular nucleic acid: this encodes the nucleic acid sequence to analyzed with the spatial DNA barcode on the oligonucleotide. After library preparation and DNA sequencing, the sequence of the spatial barcode is determined along with DNA or RNA sequence information. The spatial barcode, which was added in known order to microsamples that were also ordered in known order, can decode where in the specimen the microsample orginated. Two and three dimensional spatial relationships of the microsamples and cells can then be determined and interpreted with the DNA or RNA sequence information to develop spatial information of what cells were present in the specimen, where the cells were located, the cell's DNA sequence and/or RNA expression, and other information.

Different embodiments of the Single Cell Spatial Analysis System can encode the spatial information for decoding by analytical methods comprised of DNA sequencing, DNA microarrays, RNA sequencing, mass spectrometry, Raman spectroscopy, electrophysiology, flow cytometry, and many other analytical methods well known to one skilled in the art including multidimensional analysis. For nucleic acids, the spatial position of where the cells originated from the specimen or tissue is encoded into the DNA sequence information, in one embodiment, by utilizing paramagnetic beads with a spatial barcode in an attached oligonucleotide that is unique for each cell/bead combination. The spatial barcode may be incorporated into the cDNA product by reverse transcriptase or RNA ligase if RNA is being analyzed, or into DNA by DNA polymerase or DNA ligase if DNA is being analyzed. The RNA from the specimen is processed into cDNA and then into sequencing libraries for (N)NGS analysis, while preserving the information of the spatial organization of the cells within the original specimen by attachment of a spatial encoding nucleic acid barcode. In other instances, DNA is processed to a ready to sequence library; both RNA and DNA may be analyzed from a single cell, or nucleic acid and other properties, such as metabolites or proteomics, can be analyzed. The system described is compatible with commercially available downstream library preparation and analysis by both NGS and NNGS sequencers. The term (N)NGS is used to connote either NGS or NNGS sequencers or sample preparation methods as appropriate. For protein or metabolomic analysis, the Single Cell Spatial Analysis System encodes the spatial position of the microsample for downstream analysis by adding barcodes comprising markers or isotopes. As contemplated herein, next generation sequencing (NGS) or next-next generation sequencing (NNGS) refers to high-throughput sequencing, such as massivley parallel sequencing, (e.g., simultaneously (or in rapid succession) sequencing any of at least 100,000, 1 million, 10 million, 100 million, or 1 billion polynucleotide molecules). Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Maxam-Gilbert or Sanger sequencing, primer walking, sequencing using PacBio, SOLiD, Ion Torrent, Genius (GenapSys) or Nanopore (e.g., Oxford Nanopore) platforms and any other sequencing methods known in the art.

The Single Cell Spatial Analysis System described can have multiple subsystems and modules that perform processing or analysis. In a preferred embodiment, there is a subsystem, the Spatial Preparation Subsystem™, that inputs tissue and/or other specimens and outputs microsamples of single cell(s) encoded with cellular location information which may be DNA barcodes or other encoding methods. In one embodiment, the first module, the Spatial Sampler™ module, collects samples from defined areas of specimen(s) to provide single cells through a fluidic system in the order of their original spatial orientation to the second module, the Spatial Encoder™ module.

In one embodiment, cell imaging solutions, such as cell specific antibodies, stains, or other reagents, can be added to the tissue and an optical or other imaging device scans the tissue in the Spatial Sampler module. The optical cellular image information can be used to decide which part or subregions of the specimen should be analyzed or to gather information to correlate with the downstream analysis. In other embodiments, solutions comprised of antagonists, chemicals, biologicals, therapeutic drugs, or other compounds can be added to the tissue as needed before sampling and analysis. The Spatial Sampler module can then apply solution(s) to disassociate tissue or other specimens; as needed, the progression of dissociation can be monitored optically or by other means in the Spatial Sampler module. In one embodiment, for protein, metabolic, or other analysis, the Spatial Sampler module can apply solutions that encode the spatial position, comprised of combinations of isotopes or fluors, or marker molecules not present in the specimen, that are later decoded to identify where in the specimen the microsample originated.

In a preferred embodiment of the Spatial Sampler module, after tissue dissociation, a transfer device, such as a multifunctional head, can then collect a layer from the specimen onto a surface such as a cell impermeable transfer membrane with vacuum applied. The transfer device can be moved to an input device for a fluidic system which has one or more fluidic channels, wells, or surfaces where microsamples from a subregion of the surface are transferred in physical positional order into the fluidic channel(s), well, or surface. When fluidic channels or microchannels are used, the microsamples are entrained in a fluidic flow in known order that can be tracked to the physical position of the microsample in the original specimen. The channels may be capillaries, microchannels, micropipettes, or of other forms. Microsamples may be transferred one at a time or multiple samples transferred in parallel. In another embodiment, the input device directly samples the specimen.

In the Spatial Encoder module, for nucleic acids, the spatial position of where the cells originated from the tissue is encoded into the DNA sequence information in one embodiment by utilizing paramagnetic beads with an attached oligonucleotide with a spatial barcode unique for each cell/bead combination. The spatial barcode can be incorporated into the cDNA product by reverse transcriptase if RNA is being analyzed or into DNA from a primer by DNA polymerase or DNA ligase if DNA is being analyzed. In some instances the primer is attached to a solid surface such as a paramagnetic bead, microparticles, fibers, channel, wall, flowcell, membranes, test tubes, pipette tips or microwells or other surface. The term bead is used to encompass any solid surface, porous surface, or other implementations without limitation including flat surfaces.

In a preferred embodiment for nucleic acids, the Spatial Encoder module integrates delivery of spatially barcoded beads entrained in known order with microdrops, e.g., nanofluidic droplet or bolus generation and sample preparation of DNA, RNA, or cDNA. The spatially encoded beads have DNA or other barcodes that identify which microsample is being analyzed and, by knowing the order the microsamples were taken and subsequent handling, the physical position of the microsample in the specimen is encoded. In some embodiments, the spatially barcoded beads are added using a microfluidic nozzle to generate microdrops (nanodroplets or in others boluses are generated from the microsample in an immiscible fluid with preferably one spatically barcoded bead per droplet or bolus and only one cell. In some instances the nanodroplets or boluses may perform cellular lysis, mRNA binding, and cDNA reaction workflows. In others, cellular lysis, DNA binding, and DNA amplification reactions may be performed.

In some instances, a third module, the Spatial Librarian Subsystem (also referred to as a "Spatial Librarian System" or "Spatial Librarian Module") prepares an (N)NGS library for nucleic acid analysis from the microdrops (nanodroplets or boluses). In the Spatial Librarian Subsystem, the nanodroplets or boluses are processed separately or in the preferred embodiment the nanodroplets or boluses are pooled after spatial encoding to process many single cells and microsamples simultaneously. The Spatial Librarian module performs the necessary biochemistry to add adapters as needed, prepare an (N)NGS sequencing library, amplify as necessary, and perform quality control of the library. In other embodiments, the analytical function, such as DNA sequencing, is incorporated to create a sample-to-answer system.

In one aspect provided herein is a system comprising: (i) a biological specimen; and (ii) added to each of a plurality of different microsamples from the biological specimen, a marker comprising spatial information that encodes the original spatial position of the microsample within the biological specimen. In one embodiment the biological specimen comprises human tissue, animal tissue, or plant tissue, a biopsy, a cellular conglomerate, an organ fragment, an organism, whole blood, bone marrow, biome, a biofilm, a fine needle aspirate or any other solid, semi-solid, gelatinous, or frozen three dimensional or two dimensional matrix of biological nature. In another embodiment the microsamples comprise a single cell or a plurality of cells. In another embodiment the marker comprises a polynucleotide. In another embodiment the nucleic acid is bound to a membrane, chip surface, bead, surface, flow cell, or particle or is indirectly bound via an adapter molecule e.g., a complementary nucleic acid or a chemical crosslinker. In another embodiment the marker comprises a peptide, antibody, protein, small molecule, isotope such as lanthanide, Raman marker, mass tag, fluorescent or chemiluminescent probe. In another embodiment the microsamples are dissociated from the biological specimen. In another embodiment the microsamples are entrained in microdrops in a fluidic stream. In another embodiment the microsamples are supported by at least one substrate, e.g., a membrane.

In another aspect provided herein is a device for the analysis of a biological sample, the device comprising: a sample module configured to extract microsamples from a biological specimen; and a recipient module configured to receive the microsample biological specimen from the sample module for analysis. In one embodiment the recipient module performs a downstream analysis selected from nucleic acid sequencing, next generation sequencing, next next generation sequencing, proteomic, genomic, gene expression, gene mapping, carbohydrate characterization and profiling, lipid characterization and profiling, flow cytometry, imaging, microarray, metabolic profiling, functional, or mass spectrometry or combinations thereof.

In another aspect provided herein is a device comprising: an element selected from a membrane, filter, surface, capillary, microchannel, device, and microfabricated chip; and means to bring the element into direct contact or close proximity to a biological specimen for the purpose of labeling or extracting a plurality of microsamples in an order based on their original spatial position within the biological specimen.

In another aspect provided herein is a system comprising: a stage for supporting a biological specimen; a device comprising an array of markers comprised in beads, surfaces, flat or microfabricated structures; means for transferring the array of markers into or onto the biological specimen at predetermined spatial positions.

In another aspect provided herein is a method comprising: adding, to each of a plurality of different microsamples from a biological specimen, a marker comprising spatial information that encodes the original spatial position of the microsample within the biological specimen. In one embodiment the method further comprises dissociating the microsamples from the biological specimen. In another embodiment the method comprises adding the markers to the microsamples before dissociating the microsamples from the biological specimen. In another embodiment the method comprises adding the markers to the microsamples after dissociating the microsamples from the biological specimen. In another embodiment each microsample comprises a single cell. In another embodiment each microsample comprises a plurality of cells. In another embodiment dissociating the microsamples comprises extracting the microsamples in a raster pattern across the biological specimen. In another embodiment the microsamples are dissociated in a 3-D pattern. In another embodiment dissociating comprises contacting the biological specimen with a membrane, applying vacuum to the membrane to hold a layer comprising the microsamples; and removing the microsamples held by the membrane from the biological specimen. In another embodiment the method comprises removing a second layer of the microsamples from the biological specimen after a first layer is removed. In another embodiment the method further comprises moving the dissociated microsamples into a fluidic stream. In another embodiment the method comprises the microsamples are moved into the fluidic stream in an order correlated with their original spatial position in the biological specimen. In another embodiment the method comprises microsamples are incorporated into microdrops (e.g., nanodroplets or boluses) in the fluidic stream. In another embodiment the method comprises the microdrops contain one or more beads. In another embodiment the method comprises the beads are paramagnetic. In another embodiment the method comprises the beads are functionalized with oligonucleotides comprising the spatial information in the form of a nucleotide barcode. In another embodiment the method comprises the nucleotide barcode is unique for each cell or group of cells in the microsample. In another embodiment the method comprises the oligonucleotide comprises barcodes for cellular, molecular, or quality control purposes. In another embodiment the method comprises the nucleic acid of the sample component including but not limited to groups of cells or single cells is enzymatically combined with the oligonucleotide of the bead. In another embodiment the method comprises the nucleic acid is subjected to library preparation and nucleic acid sequencing. In another embodiment the method comprises the oligonucleotide further comprises a poly T tail, and the method comprises capturing mRNA molecules from the microsamples having a poly T tail; and reverse transcribing the mRNA molecules to produce cDNA molecules comprising the barcode where the barcode provides the spatial information. In another embodiment the method comprises the oligonucleotide further comprises a capture sequence complementary to a target sequence, and the method comprises capturing DNA molecules from the microsample having the target sequence; and extending the oligonucleotide to produce a nucleic acid molecule having a copy of the target sequence and comprising the barcode, wherein the barcode provides the spatial information. In another embodiment the method comprises dissociating comprises contacting the biological sample with a cell dissociation solution comprising at least one protease that digests extracellular matrix. In another embodiment the method comprises the at least one protease is selected from collagenases, elastase, trypsin, papain, hyaluronidase, chymotrypsin, neutral protease, clostripain, caseinase, neutral protease (Dispase®), DNAse, protease XIV. In another embodiment the method comprises the cell dissociation solution is in the form of a fluid, mist, fog, or aerosol applied to the biological sample. In another embodiment the method further comprises decoding the spatial information in the microsamples to determine the original spatial position of each microsamples.

In another aspect provided herein is a method comprising: providing a biological specimen; collecting microsamples from each of a plurality of different spatial positions in the biological specimen; attaching to nucleic acids in each microsample a marker comprising a nucleic acid barcode comprising spatial information that encodes the original spatial position of the microsample within the biological specimen, thereby producing spatial encoded nucleic acids; sequencing the spatial encoded nucleic acids; and based on the spatial information attached to each spatial encoded nucleic acids, determining the original spatial location of the nucleic acid in the biological specimen. In one embodiment the method comprises sequencing spatial encoding nucleic acids combined from a plurality of different microsamples in a single high throughput sequencing run.

In another aspect provided herein is a system having a graphical user interface that presents, based on spatial information obtained from microsamples of a biological specimen, a graphical representation of the biological specimen including original spatial position of a plurality of polynucleotides or polypeptides in the biological specimen.

In another aspect provided herein is a spatial preparation system configured to entrain in a fluidic stream a plurality of microsamples from a biological specimen, wherein the microsamples are contained in spatially separated microdrops in a fluidic stream and positioned in an order based on their original spatial position within the biological specimen, wherein the system comprises: a) a spatial sampler subsystem configured to extract a plurality of microsamples from different original spatial positions in a biological specimen; and b) a spatial encoder subsystem comprising one or more spatial encoder microchannels, each having an inlet and an outlet; wherein the spatial sampler subsystem delivers the microsamples to the spatial encoder microchannel inlets in a predetermined order based on their original spatial position in the biological specimen, and the spatial encoder subsystem incorporates the microsamples into spatially separated microdrops in a fluidic stream. In one embodiment of the spatial preparation system: (i) the spatial sampler subsystem comprises: (1) a specimen holder, and (2) a multifunctional head comprising a transfer head comprising one or more extraction channels, wherein the extraction channels communicate with a liquid source and, optionally, a gas source, each under positive and/or negative pressure, and wherein the one or more extraction channels comprise ends covered with one or more air permeable, cell impermeable transfer membranes, and wherein, the multifunctional head is mounted on a three axis stage to position the multifunctional head to extract, by contact adhesion or by vacuum, the microsamples from the specimen holder onto the one or more transfer membranes; and (ii) the spatial encoder subsystem comprises: (1) a microdroplet generator comprising a source of immiscible liquid in communication with each spatial encoder microchannel at a junction, wherein mixture of the immiscible liquid with the fluidic stream at the junction forms spatially separated microdrops comprising the microsamples; and (2) optionally, a microsample encoder assembly comprising a plurality of reservoirs, each comprising a different spatial marker and each communicating with the spatial encoder microchannel, and, optionally reservoirs comprising a reactants sufficient to attach the tags to analytes in the microsamples, wherein different spatial markers are incorporated with microsamples in different microdrops. In another embodiment the multifunctional head further comprises a dispense head configured to dispense liquids, e.g., imaging reagents or dissociation solution, onto the biological specimen. In another embodiment the transfer head comprises a plurality of extraction channels where in the extraction channels are arrayed in a two dimensional array (e.g., a line) or a three-dimensional array (e.g., a plane). In another embodiment the spatial encoder subsystem comprises a plurality of fluidic channels that merge into the encoder channel in which each has an inlet configured to receive the microsamples from an extraction channels. In another embodiment the transfer membranes have attached thereto a plurality of capture elements, each capture element comprising a particle, which is optionally paramagnetic, having attached thereto one or more antibodies that bind into cells in the biological specimen, and nucleic acid markers comprising positional barcodes comprising spatial information where the spatial information calling to the position of the particle on the multifunctional head. In another embodiment the nucleic acid markers further comprise cell markers identifying the cell to which particle binds, and/or molecular barcodes that differently label different nucleic acid molecules and a single cell.

In another aspect provided herein is a spatial analysis system comprising: a) a spatial preparation subsystem as disclosed herein, and b) a spatial librarian subsystem configured to perform a series of biochemical reactions on an emulsion comprising microdrops produced by the spatial preparation subsystem, wherein the spatial librarian subsystem comprises: a) a reaction device comprising an inlet configured to receive microdrops from the spatial preparation subsystem, at least one reaction chamber, and an outlet; b) a reagent rail communicating with the reaction device through a microchannel and comprising reagent sufficient to perform at least one of biochemical reaction on analytes in the microdrops; and c) one or more pumps configured to move the reagents from the reagent rail through the microchannel to the reaction chamber of the reaction device. In another embodiment the spatial librarian subsystem further comprises: c) a temperature controller configured to control temperature in the reaction chamber. In another embodiment the spatial librarian subsystem further comprising: c) a magnet configured to reversibly immobilize paramagnetic particles contained in the reaction chamber. In another embodiment the biochemical reactions comprise at least: (i) reverse transcription of messenger RNA into cDNA; and (ii) amplification of cDNA. In another embodiment the biochemical reactions comprise at least: (i) primer extension of a primer hybridized to a DNA template to create an extension product; and (ii) amplification of the extension product.

In another aspect provided herein is a method comprising entraining in a fluidic stream a plurality of microsamples from a biological specimen, wherein the microsamples are contained in spatially separated microdrops in the fluidic stream and positioned in an order based on their original spatial position within the biological specimen. In one embodiment the method comprises: a) providing a biological specimen; b) collecting microsamples from each of a plurality of different spatial positions in the biological specimen; c) introducing the microsamples in a predetermined order into a fluidic stream in a fluidic channel; d) dividing the fluidic stream into microdrops by introducing boluses of immiscible liquid into the fluidic channel, whereby the microsamples are incorporated into microdrops that are spatially separated from each other in the fluidic stream. In another embodiment the method further comprises: (i) introducing into the fluidic stream a plurality of different spatial markers encoding spatial information, wherein the different spatial markers are incorporated into different microdrops in the fluidic stream, thereby encoding each microdrop with spatial information. In another embodiment the analytes comprise nucleic acids and the spatial markers comprise nucleic acids comprising nucleic acid barcodes, wherein the method further comprises: (e) combining microdrops in a container in the form of an emulsion; (f) generating spatially tagged nucleic acids by tagging nucleic acid analytes with the nucleic acid barcodes; (g) breaking the emulsion; (h) amplifying the tagged nucleic acids. In another embodiment the analytes comprise polyadenylated mRNA and the nucleic acid markers further comprise polyT tail, and generating spatially tagged nucleic acids comprises: hybridizing the polyT tail to polyadenylated mRNA nucleic acid markers to the mRNA molecules barcodes and reverse transcribing the polyadenylated messenger RNA to produce that spatially tagged cDNA molecules; performing second strand synthesis on the spatially tagged cDNA molecules to produce tagged double stranded cDNA molecules. In another embodiment the analytes comprise DNA molecules and the nucleic acid markers further comprise a nucleotide sequence complementary to a target sequence, and generating spatially tagged nucleic acids comprises:hybridizing the complementary nucleotide sequence to a target sequence in the nucleic acid molecules and extending the nucleic acid markers to produce a double-stranded DNA molecule. In another embodiment the method further comprises: applying imaging reagent to the biological sample; imaging the biological sample to which the imaging reagent has been applied; based on the imaging selecting features of interest at predetermined spatial positions in the biological sample; and extracting the microsamples including the selected features of interest. In another embodiment the method further comprises, based on spatial information encoded in the microsamples, determining the initial spatial position of the selected features in the biological specimen.

In another aspect provided herein is an apparatus, composition of matter, or article of manufacture, and any improvements, enhancements, and modifications thereto, as described in part or in full herein and as shown in any applicable Figures, including one or more features in one or more embodiment.

In another aspect provided herein is an apparatus, composition of matter, or article of manufacture, and any improvements, enhancements, and modifications thereto, as described in part of in full herein and as shown in any applicable Figures, including each and every feature.

In another aspect provided herein is a method or process of operation or production, and any improvements, enhancements, and modifications thereto, as described in part or in full herein and as shown in any applicable Figures, including one or more feature in one or more embodiment.

In another aspect provided herein is a method or process of operation or production, and any improvements, enhancements, and modifications thereto, as described in part or in full herein and as shown in any applicable Figures, including each and every feature.

In another aspect provided herein is a product, composition of matter, or article of manufacture, and any improvements, enhancements, and modifications thereto, produced or resulting from any processes described in full or in part herein and as shown in any applicable Figures.

BRIEF DESCRIPTION OF THE SEVERAL VIEWS OF THE DRAWINGS

The skilled artisan will understand that the drawings, described below, are for illustration purposes only. The drawings are not intended to limit the scope of the present teachings in any way.

FIG. 22 illustrates a workflow to spatially encode genomic DNA from single cells from a specimen.

FIG. 23 illustrates a workflow to spatially encode targeted regions of genomic DNA from single cells from a specimen.

DETAILED DESCRIPTION OF THE INVENTION

Figure 1:
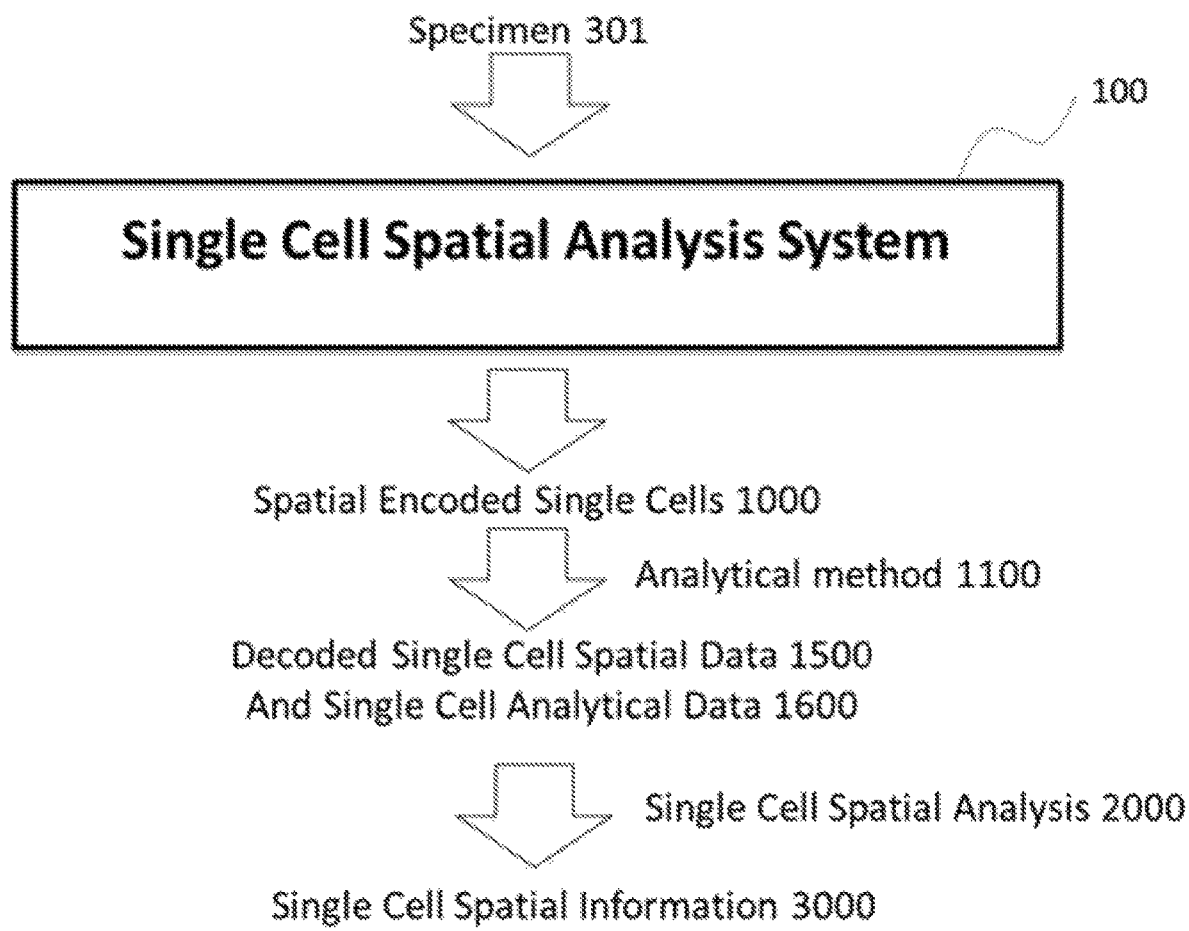
FIG. 1 shows an overview of the overall workflow to generate single cell spatial information from specimens.

NGS information, mass spectrometry and other modern high-throughput analysis systems have revolutionized life and medical sciences. However, these and other high-throughput analysis systems fail to retain spatial information about where in the specimen the sample or microsample originated. It is anticipated that single cell spatial information, or spatial information from groups of cells, of genomic, proteomic including protein expression, carbohydrate, lipid, and metabolism of individual cells will provide fundamental scientific knowledge and revolutionize new research and clinical capacities.

All patents, patent applications, published applications, treatises and other publications referred to herein, both supra and infra, are incorporated by reference in their entirety. If a definition and/or description is set forth herein that is contrary to or otherwise inconsistent with any definition set forth in the patents, patent applications, published applications, and other publications that are herein incorporated by reference, the definition and/or description set forth herein prevails over the definition that is incorporated by reference.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Specimen: The term "specimen," as used herein, refers to an in vitro cell, cell culture, virus, bacterial cell, fungal cell, plant cell, bodily sample, or tissue sample that contains genetic material. In certain embodiments, the genetic material of the specimen comprises RNA. In other embodiments, the genetic material of the specimen is DNA, or both RNA and DNA. In certain embodiments the genetic material is modified. In certain embodiments, a tissue specimen includes a cell isolated from a subject. A subject includes any organism from which a specimen can be isolated. Non-limiting examples of organisms include prokaryotes, eukaryotes or archaebacteria, including bacteria, fungi, animals, plants, or protists. The animal, for example, can be a mammal or a non-mammal. The mammal can be, for example, a rabbit, dog, pig, cow, horse, human, or a rodent such as a mouse or rat. In particular aspects, the tissue specimen is a human tissue sample. The tissue specimen can be, for example, a blood sample. The blood sample can be whole blood or a blood product (e.g., red blood cells, white blood cells, platelets, plasma, serum). The specimen, in other non-limiting embodiments, can be saliva, a cheek, throat, or nasal swab, a fine needle aspirate, a tissue print, cerebral spinal fluid, mucus, lymph, feces, urine, skin, spinal fluid, peritoneal fluid, lymphatic fluid, aqueous or vitreous humor, synovial fluid, tears, semen, seminal fluid, vaginal fluids, pulmonary effusion, serosal fluid, organs, bronchio-alveolar lavage, tumors, frozen cells, or constituents or components of in vitro cell cultures. In other aspects, the tissue specimen is a solid tissue sample or a frozen tissue sample. In still further aspects, the specimen comprises a virus, bacteria, or fungus. The specimen can be an ex vivo tissue or sample or a specimen obtained by laser capture microdissection. The specimen can be a fixed specimen, including as set forth by U.S. Published Patent Application No. 2003/0170617 filed Jan. 28, 2003.

In some embodiments, biomolecules including one or more polynucleotides or polypeptides are spatially encoded. In some embodiments, the polynucleotide can include a single-stranded or double-stranded polynucleotide. In some embodiments, the polypeptide can include an enzyme, antigen, hormone or antibody. In some embodiments, the one or more biomolecules can include RNA, mRNA, cDNA, DNA, genomic DNA, microRNA, long noncoding RNA, ribosomal RNA, transfer RNA, chloroplast DNA, mitochondrial DNA, or other nucleic acids.

It will be readily apparent to one of ordinary skill in the art that the embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

Referring to FIG. 1, the Single Cell Spatial Analysis System 100 accepts specimens 301 and processes one or more microsamples 125 to encode the physical location of the microsample 125 within the specimen 301 to produce spatially encoded single cells 1000 in microdrops, e.g., nanodroplets or boluses, by adding a marker such as a DNA barcode that encodes for the location of the microsample 125. Known markers are added in known order to ordered microsamples 125 to encode the spatial position. Analysis method 1100, such as DNA sequencing, mass spectrometry, or other analytical methods, generates single cell analytical data 1600, such as DNA sequence or proteomics, and also decodes the encoded spatial information to produce decoded single cell spatial information 1500. Multiple sample preparation and analytical methods can be used on a specimen. In some aspects where the biomolecules are nucleic acids, the downstream processes can include without limitation, nucleic acid sequencing, targeted resequencing, genotyping analysis, mutation analysis, copy number variation assessment, allele frequency assessment, plasmid construction, cloning, and the like. The decoded single cell spatial information 1500 identifies the spatial position 130 where microsample 125 originated in specimen 301. The single cell analytical data 1600 is analyzed by single cell spatial analysis 2000 software to produce single cell spatial information 3000 which has the analytical data and associated physical position information of the microsample 125.

Figure 2:
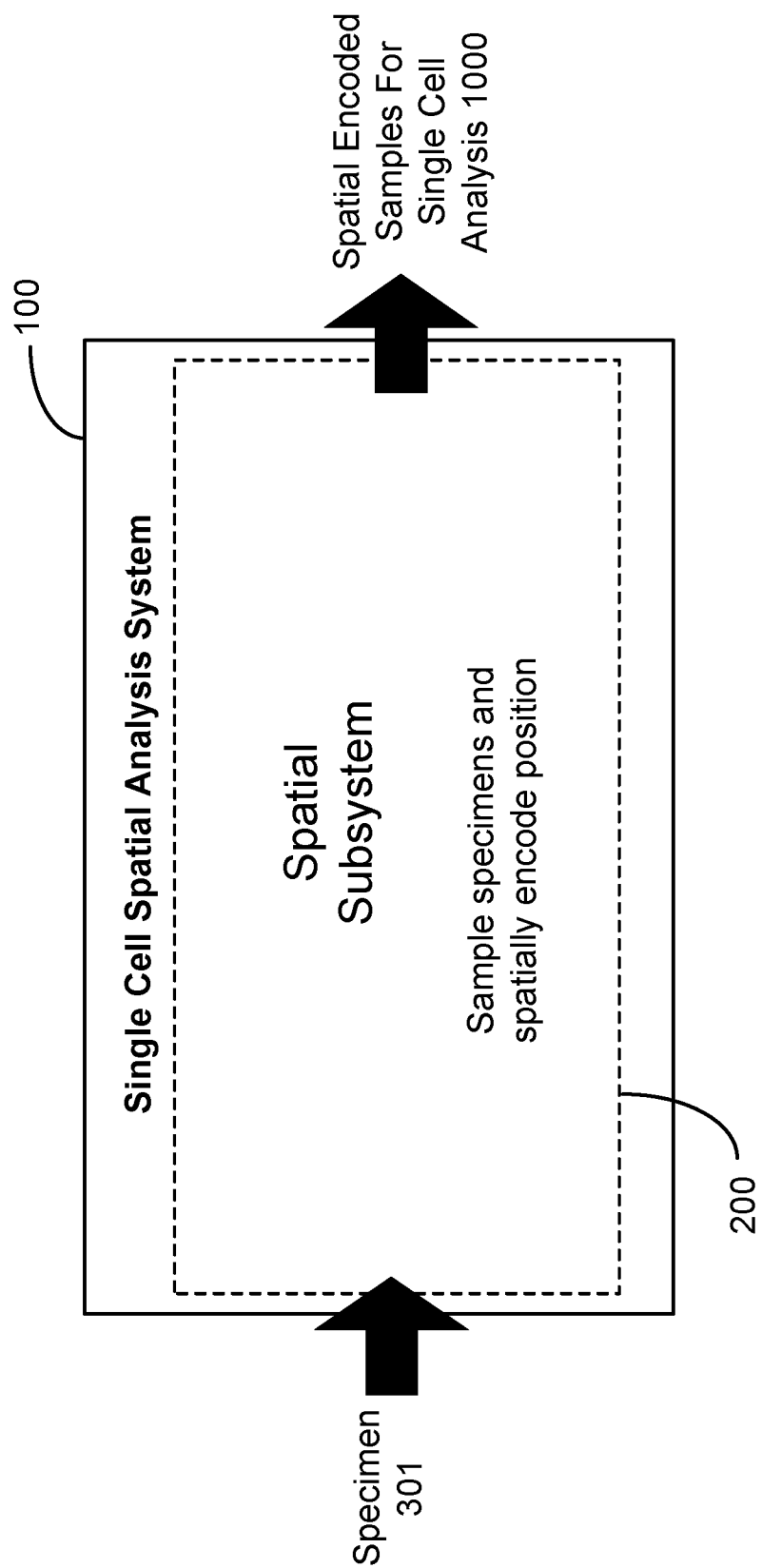
FIG. 2 shows an overview of a Single Cell Spatial Analysis System. Tissue or other specimens are converted to single cells and encoded with spatial information.

Referring to FIG. 2, the Single Cell Spatial Analysis System 100 is in some embodiments an automated sample preparation system that collects cells from areas of tissue, biofilms, and other matrices containing biological material and generates spatially-encoded samples for analysis of single cells 1000 and groups of cells from the same subregion. The Single Cell Spatial Analysis System 100 can have pushbutton operation for either specialists or non-specialists to generate samples with spatial information encoded from specimens for medical, health, life science research, and other applications.

The Single Cell Spatial Analysis System 100 in one embodiment has a Spatial Subsystem 200 that inputs specimens and outputs samples for spatially encoded single cells 1000. The Spatial Preparation Subsystem 200 can accommodate many different types of specimens, comprised of fresh and snap-frozen tissue in the form of microtome slices (cryo, laser or vibrating); bulk material obtained by surgical excision, biopsies, fine needle aspirates; samples from surfaces, and other matrices. The specimens are positioned onto the sampling stage. Subregions 150 will then be addressed automatically by a multifunctional head 330 to transfer subregions 150 of microsamples 125 in 2-D spatial order to generate single cells and process them into cDNA or DNA with a spatial nucleic acid barcode, or other spatial markers added, or other analytes, e.g., proteins, metabolites, enzymes, with isotopes or other spatial markers added. The next physical layer of the specimen 301 subregion of interest can then be collected and analyzed to generate a second 2-D spatial patterns of DNA sequence, RNA expression, protein expression, protein activity, RNA activity, lipid composition and abundance, carbohydrate composition and abundance, and metabolites as well as any other biological components. The third physical layer can then be collected and analyzed. The physical layers can then be oriented to produce a three dimensional pattern.

The basic elements of the Single Cell Spatial Analysis System 100 can be configured in multiple ways depending on the specimen(s) and analytes to be analyzed. In the following examples, a few of the numerous configurations are described in detail but in no way is the invention limited to these configurations as will be obvious to one skilled in the art. Nonetheless in many configurations, there are many common elements, in particular adding a barcode or other exogenous material to the microsample 125, or to single cells or groups of single cells from the microsample 125 to encode where physically from the specimen the microsample 125 originated. Once the single cells or groups of cells have been analyzed, the barcode can be decoded and the physical position of the microsample 125 in the 3-D structure of the specimen used to understand the composition, function, cell type, activity, genetics, physiology, interconnections, and other attributes of the specimen with single cell spatial information 3000.

Figure 3:
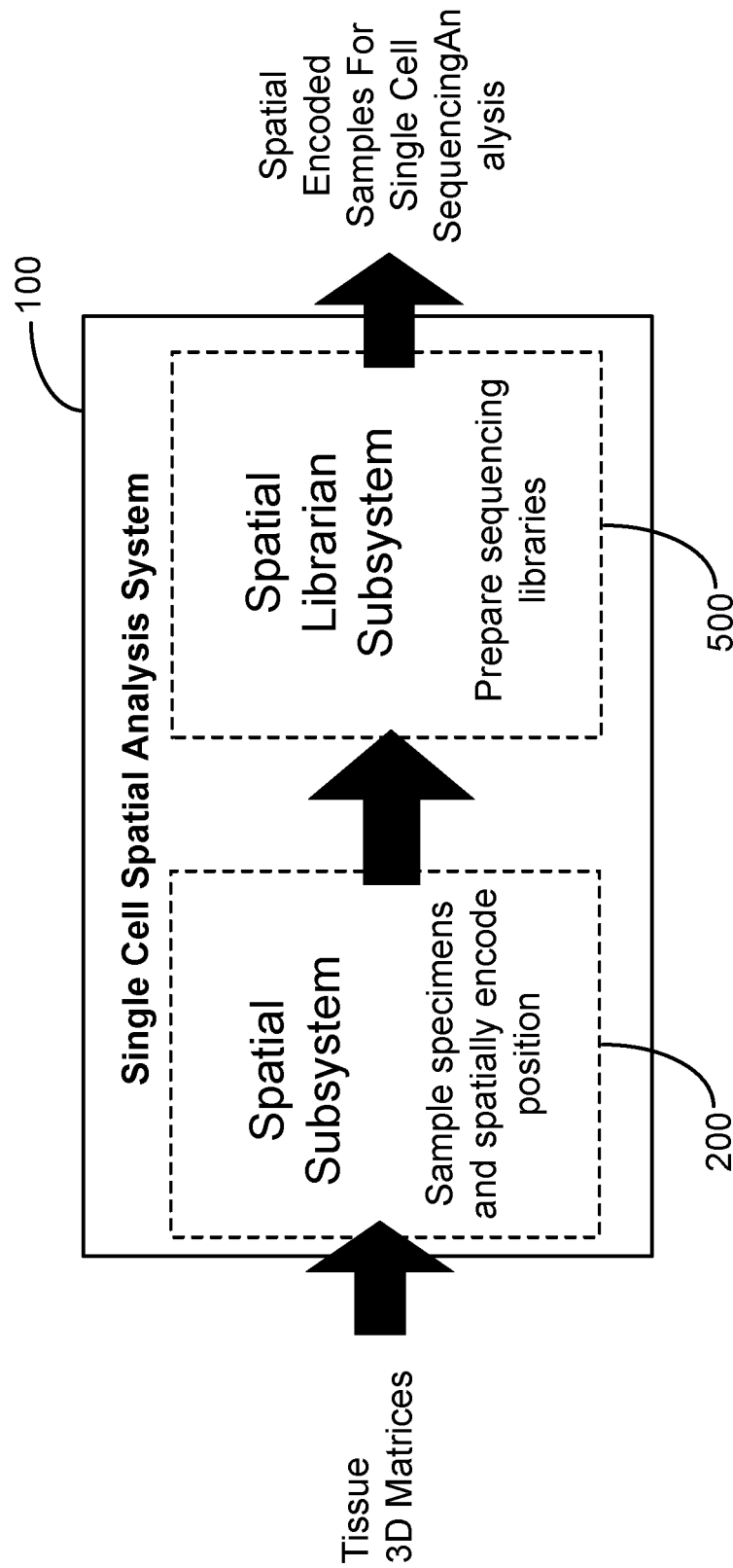
FIG. 3 shows an overview of a Single Cell Spatial Analysis System configured for nucleic acid sequencing. Specimens are converted to single cells and encoded with spatial information in the Spatial Preparation Subsystem for integrated NGS library preparation in the Spatial Librarian Subsystem.

In a preferred embodiment, referring to FIG. 3, for nucleic acid analysis, the Single Cell Spatial Analysis System 100 has two subsystems, the Spatial Preparation Subsystem 200 and the Spatial Librarian Subsystem 500.

Figure 4:
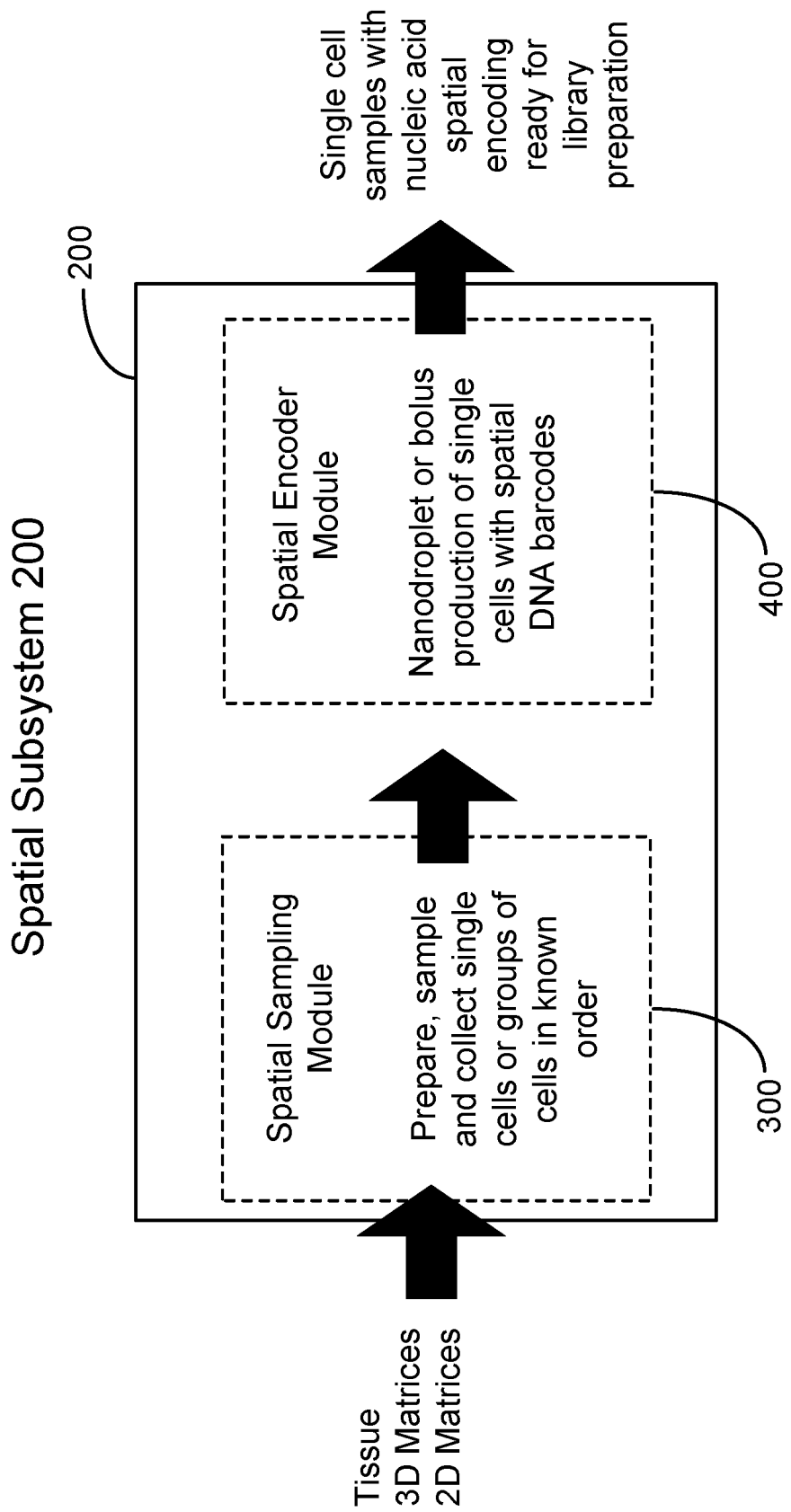
FIG. 4 shows modules of the Spatial Preparation Subsystem configured for nucleic acid sequencing. The Spatial Sampler module collects cells from defined areas and dispenses them in known order into the Spatial Encoder module that encodes the original position within the tissue into DNA using unique primers as barcodes attached to beads. The Spatial Preparation Subsystem can output samples of single cells encoded with spatial DNA barcodes that are ready for library preparation.

The Spatial Preparation Subsystem 200 can in turn be composed of two modules, the Spatial Sampler module 300 and the Spatial Encoder 400, as shown in FIG. 4. In a preferred embodiment, Spatial Sampler module 300 (i) releases cells from tissue, (ii) collects, and (iii) transfers single cells or groups of cells with defined spatial relationships in a known order into a single fluidic or microfluidic process stream, or onto a surface such as a flow cell, or into a two-dimensional array of wells, or other ordered or unordered processes. In a preferred embodiment, the output of the Spatial Sampler 300 is single cells in a microfluidic flow in a known order. Spatial Encoder module 400 adds spatial barcodes to the sample and outputs the single cells with spatial barcodes. FIG. 4 shows Spatial Encoder module 400 configured for DNA sequencing.

A. Spatial Sampler Description

Figure 5:
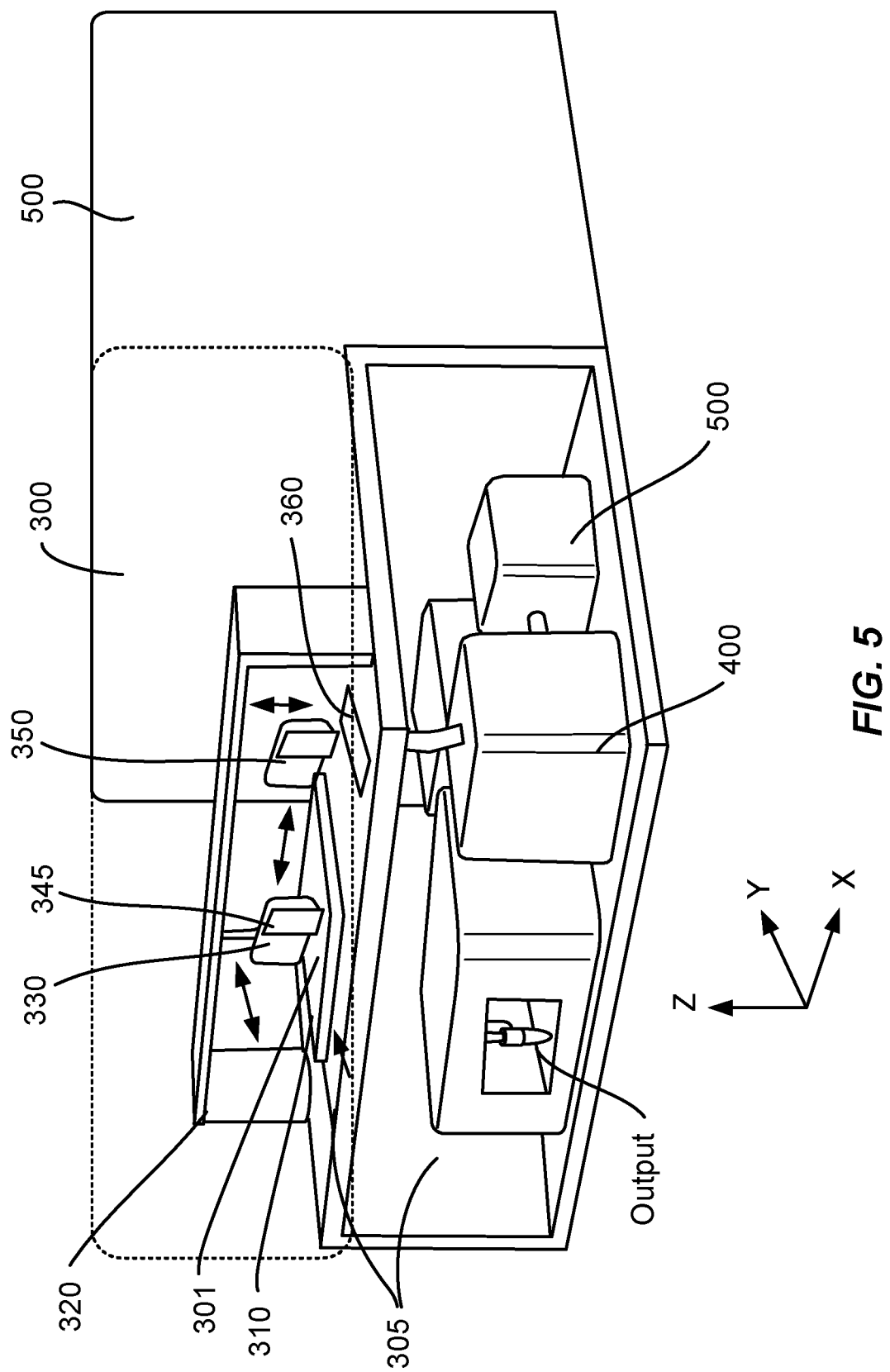
FIG. 5 shows a Single Cell Spatial Analysis System configured for production of nucleic acid spatial libraries.

Referring to FIG. 5, in a preferred embodiment, configured for nucleic acid analysis, specimen 301 is placed in a specimen holder 310 which is inserted into the Spatial Sampler module 300 by loading mechanism 305. Specimen holder 310 may be temperature controlled. The loading mechanism can have a mechanical slide, stage, pneumatic actuator, or other mechanism, that accepts specimen holder 310 and moves it into the Single Cell Analysis System 100, either automated or manually, into a fixed position in the Spatial Sampler module 300 or other mechanism. Spatial Sampler module 300 can have a three axis stage 320 that moves a multifunctional head in the x, y and z directions 330 to collect microsamples 125 in a spatially defined manner from specimen 301 at capture position 345 and dispenses the collected microsamples 125 at dispense position 350 into input device 360.

In some embodiments the fluidics of the Single Cell Spatial Analysis System 100 are incorporated onto cartridge(s) 4000. In some embodiments of the Single Cell Spatial Analysis System 100, the valves for the subsystems are microvalves, which in some embodiments are created in microchips with microchannels. Microvalves are well know to those skilled in the art. Microvalves can be actuated by, for example, mechanical force, pneumatic pressure, electrostatic force, piezoelectric force, or thermal expansion force. They may be have internal or external actuators. Pneumatic valves include, for example, diaphragm valves that employ a flexible membrane of the pneumatic pressure or vacuum to close or open a fluid channel. Electrostatic valves may include, for example, a polysilicon membrane or a polyimide cantilever that is operable to cover a hole formed in a substrate. Piezoelectric valves may include external (or internal) piezoelectric disks that expand against a valve actuator. Thermal expansion valves may include a sealed pressure chamber bounded by a diaphragm. Heating the chamber causes the diaphragm to expand against a valve seat.

Microvalves can comprise mechanical (thermopneumatic, pneumatic, and shape memory alloy), non-mechanical (hydrogel, sol-gel, paraffin, and ice), and external (modular built-in, pneumatic, and non-pneumatic) microvalves (as described in C. Zhang, D. Xing, and Y. Li., Micropumps, microvalves, and micromixers within PCR microfluidic chips: Advances and trends. Biotechnology Advances. Volume 25, Issue 5, September-October 2007, Pages 483-514; Díaz-González M., C. Fernández-Sánchez, and A. Baldi A. Multiple actuation microvalves in wax microfluidics. Lab Chip. 2016 Oct. 5; 16(20):3969-3976.; Kim J., Stockton A M, Jensen E C, Mathies R A. Pneumatically actuated microvalve circuits for programmable automation of chemical and biochemical analysis. Lab Chip. 2016 Mar. 7; 16(5):812-9. doi: 10.1039/c5lc01397f; Samad M F, Kouzani A Z. Design and analysis of a low actuation voltage electrowetting-on-dielectric microvalve for drug delivery applications. Conf Proc IEEE Eng Med Biol Soc. 2014; 2014:4423-6. doi: 10.1109/EMBC.2014.6944605.; Samad M F, Kouzani A Z. Design and analysis of a low actuation voltage electrowetting-on-dielectric microvalve for drug delivery applications. Conf Proc IEEE Eng Med Biol Soc. 2014; 2014:4423-6. doi: 10.1109/EMBC.2014.6944605.; Lee E, Lee H, Yoo S I, Yoon J. Photothermally triggered fast responding hydrogels incorporating a hydrophobic moiety for light-controlled microvalves. ACS Appl Mater Interfaces. 2014 Oct. 8; 6(19):16949-55. doi: 10.1021/am504502y. Epub 2014 Sep. 25.; Liu X, Li S. An electromagnetic microvalve for pneumatic control of microfluidic systems. J Lab Autom. 2014 October; 19(5):444-53. doi: 10.1177/2211068214531760. Epub 2014 Apr. 17; Desai A V, Tice J D, Apblett C A, Kenis P J. Design considerations for electrostatic microvalves with applications in poly(dimethylsiloxane)-based microfluidics. Lab Chip. 2012 Mar. 21; 12(6):1078-88. doi: 10.1039/c2lc21133e. Epub 2012 Feb. 3.; Kim J, Kang M, Jensen E C, Mathies R A Lifting gate polydimethylsiloxane microvalves and pumps for microfluidic control. Anal Chem. 2012 Feb. 21; 84(4):2067-71. doi: 10.1021/ac202934x. Epub 2012 Feb. 1; Lai H, Folch A. Design and dynamic characterization of "single-stroke" peristaltic PDMS micropumps. Lab Chip. 2011 Jan. 21; 11(2):336-42. doi: 10.1039/c0lc00023j. Epub 2010 Oct. 19) In some embodiments, cartridges 4000 are used with functionality from a group of reagents, valves or microvalves, microchannels, syringe pumps, optical devices, integrated electronics for control of cartridge 4000 functions, and lot tracking. In some embodiments microchips are used as parts of instrument or cartridges 4000. The cartridges 4000 in some embodiments hold kits to perform the chemistries including all needed reagents, including spatial barcodes attached to beads, emulsion oil, breaking solution, stains, library preparation chemistry, and other consumables.

Figure 6:
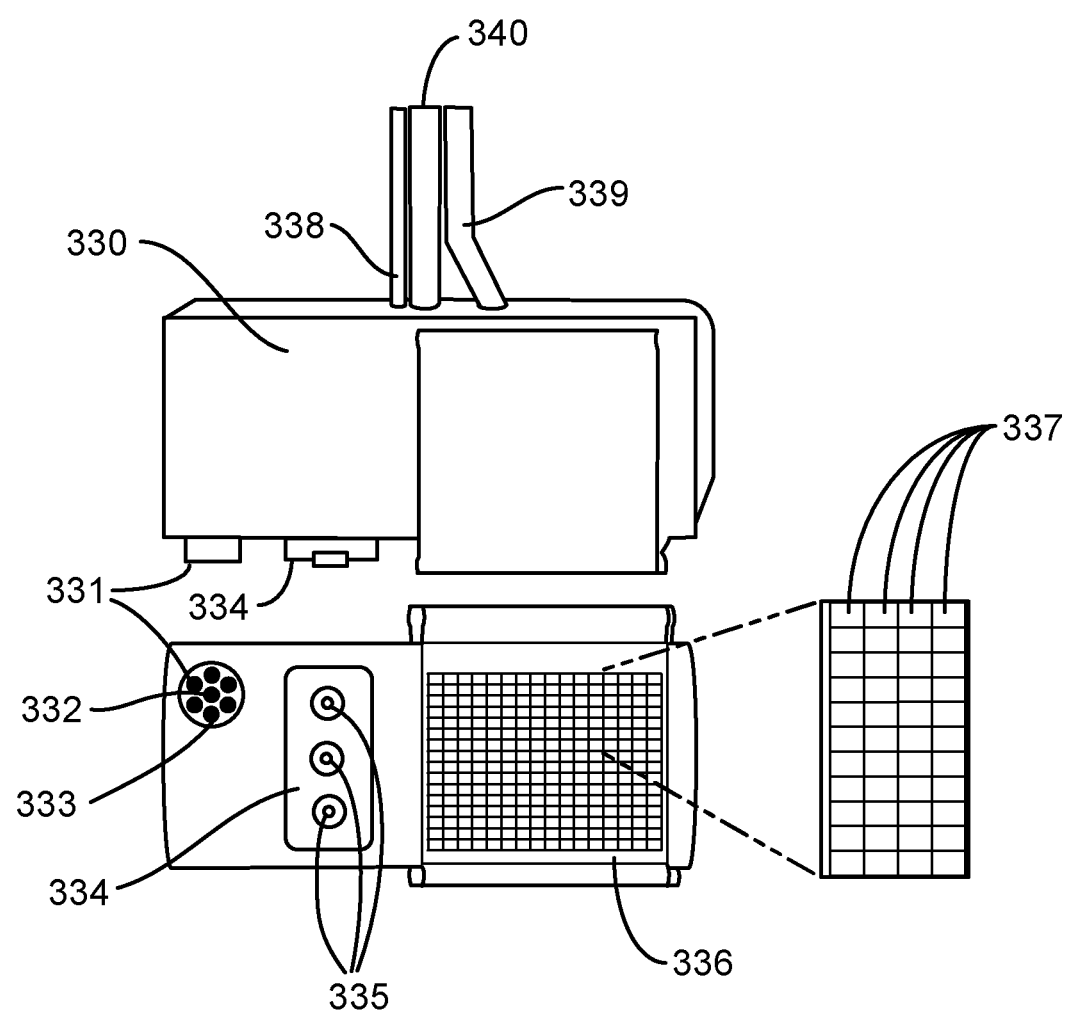
FIG. 6 shows a multifunctional head from a side view and a bottom view with an optical head, dispense head, and a changeable transfer membrane. The insert of the right of the figure shows the transfer membrane may have individually addressable subregions.

The multifunctional head 330, supported by strut 340, can have multiple functions integrated into a single head as shown in FIG. 6 or multiple heads that are moved independently can be used. As shown in FIG. 6, the multifunctional head can have an optics head 331 that in a preferred embodiment has illumination fiber 332 surrounded by multiple collection fibers 333. The illumination and collection fibers can have lenses to focus the illumination beam(s), such as a laser, arc lamp, UV lamp, or other light source, and collect reflected, fluorescent, Raman, reflected, or other light for delivery to an optics analysis device via optical fiber bundle 338. Many other optical configurations may be used or no optical capability may be used.

Multifunctional head 330 can have a dispense head 334 with one or more dispensers 335 that can apply one or more solutions to specimen 301. The dispense head 334 may use piezoelectric pumps, inkjet technology, pressure driven flow through a nozzle, or other methods to dispense liquids, gels, or gases from fluidics and pneumatic bundle 339 to specimen 301 or subregions 150 of specimen 301.

Multifunctional head 330 can have a transfer head for extracting the microsamples from a biological specimen and transferring them, e.g., into a fluidic stream. The transfer head can comprise a transfer membrane 336 to transfer a layer of the specimen. Referring to FIG. 6, a transfer membrane 336 may be made of many different materials with characteristics that prevent cells passing through it but in preferred embodiments can be permeable to air or liquids, have low adhesion for collected cells, and can be changed as needed. The transfer membrane may be selected from many materials, including semipermeable membranes; filter papers comprising cellulose and cellulose derivatives, glass fiber filters, polytetrafluoroethylene (PTFE) filters, quartz fiber filters and others; blotting membranes comprising membranes made of nitrocellulose such as ProTran, polyvinylidene difluoride (PVDF) such as Immobilon® or Hybond, nylon, cellulose nitrate, polyestersulfone, track etched polycarbonate, PVC, and others with pore sizes smaller than the cells of interest. The multifunctional head 330 may be able to apply vacuum, pressure, or fluids to the whole membrane through fluidic and pneumatic bundle 339 either to the complete surface of the membrane at the bottom of the multifunctional head or to portions of the membrane. In some embodiments, portions of the membrane are individually addressable subregions 337 to enable subregions of the specimen 301 to be collected or dispensed individually. The transfer membrane 336 can be changed through swapping out a disposable fixed membrane head, or by advancing a roll of membrane to have unused membrane, or other mechanisms. In some embodiments, the transfer membrane may be reused multiple times and not changeable. In other embodiments, the transfer membrane 336 is simply cleaned by separate cleaning modules that operate in direct contact or non-contact mode utilizing various cleaning mechanisms including, but not limited to, mechanical brushes and chemical agents such as ethanol, detergents, water, buffers, and other chemicals. The term transfer membrane 336 is used but is not intended to limit the composition or material which can be a filter, membrane, surface, film, or other material.

The Single Cell Spatial Analysis System Spatial Sampler module 300 can function as follows in one embodiment. The multifunctional head 330 is moved to the x, y directions to capture position 345. The optics head 331 scans the specimen by the multifunctional head 330 moving to the appropriate z height and being moved in the x-y axis to scan specimen 301. As needed, solutions can be dispensed onto specimen 301 or portions of the specimen by dispense head 334. The solutions can be imaging reagents, such as fluorescently directly conjugated antibodies or secondary antibodies, stains, fluorescent probes and dyes; imaging nanomaterials (including quantum dots and other nanoparticles), or other contrast or straining reagents; or reagents to stimulate or treat specimen 301 such as anticancer compounds, antibiotics, antivirals, energy sources, or other liquids, gels, or gases for the same or other functions. In some embodiments, the information gathered by the optics or other sensors is used to decide which subregions 150 of the specimen are to be sampled or to decide the next step, such as adding another reagent, scanning at a different wavelength, or another action. In some embodiments, after the application of a reagent, the transfer membrane 336 portion of the multifunctional head 330 may be used to aspirate excess reagent or all unbound reagents.

In a preferred embodiment, after optical scanning, the dispense head 334 can use a dispenser 335 to apply a dissociation solution, such as Liberase™ DH Research Grade Roche or equivalent products or custom formulations, in form of a spray, mist, or liquid to a region of the top most layer of the tissue to dissociate intercellular adhesion between cells and free the cells from the extracellular matrix. A dissociation solution comprises at least one collegenase or protease that digests extracellular matrix (F. E Dwulet and M. E. Smith, "Enzyme composition for tissue dissociation," U.S. Pat. No. 5,952,215, Sep. 14, 1999). The dissociation solutions to dissociate the tissue can be comprised of collagenases (e.g. collagenases type I, II, III, IV, and others), elastase, trypsin, papain, hyaluronidase, chymotrypsin, neutral protease, clostripain, caseinase, neutral protease (Dispase®), DNAse, protease XIV or other enzymes. The dissociation solution can be applied in one embodiment such that only the uppermost layers of cells are dissociated or deeper layer are dissociated depending on the amount and concentration of the dissociation solution, time of contact, temperature, and other parameters.

Figure 7A:
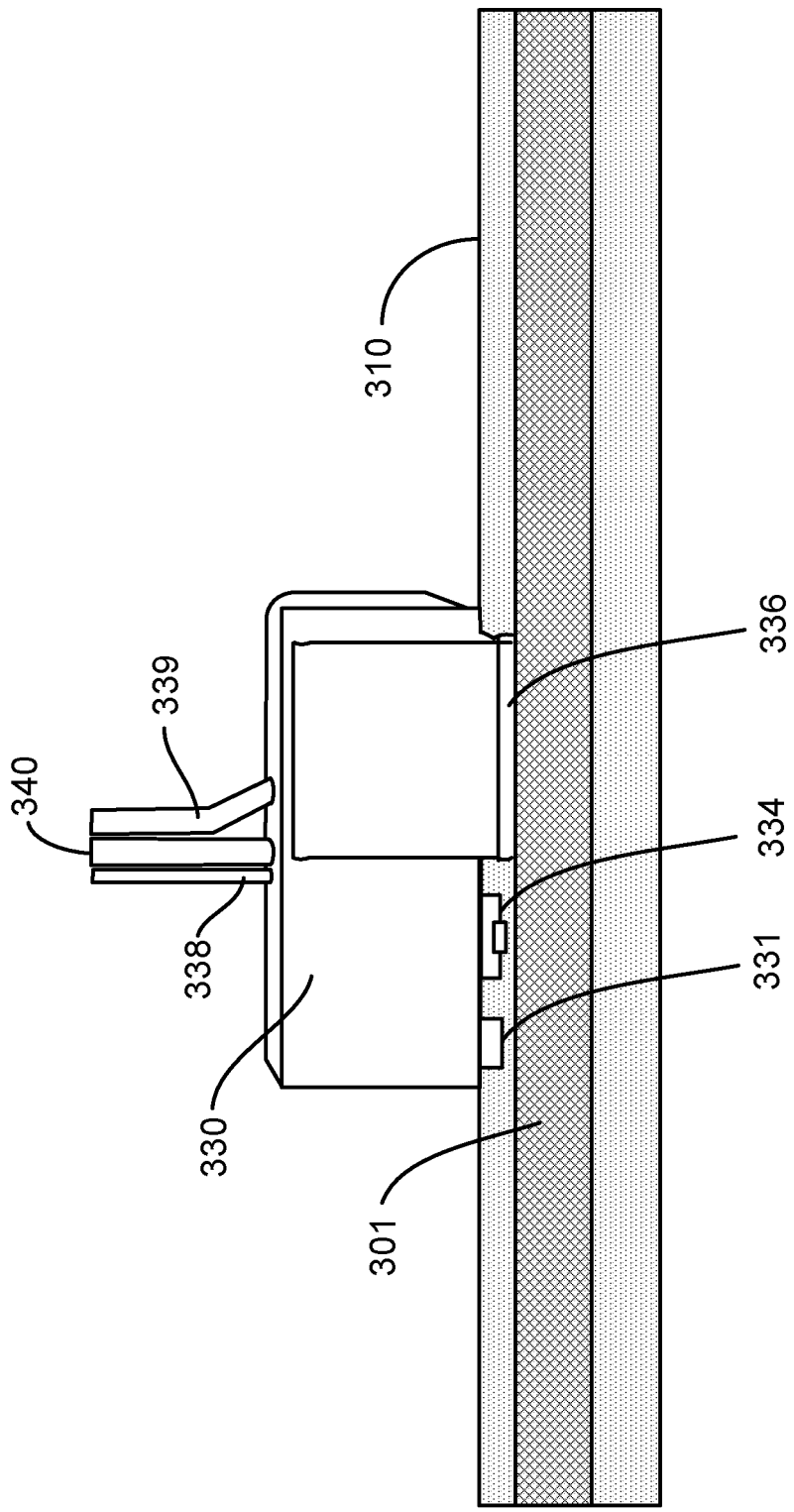
FIG. 7a shows an example of a multifunctional head with transfer membrane contacting a specimen.

Referring to FIG. 7a, after treatment to dissociate the tissue, samples are collected from the specimen by moving multifunctional head 330 in the x and y axes to the appropriate subregion 150 of specimen 301 and then multifunctional head 330 is lowered in the z direction to contact specimen 301 in specimen holder 310 with the transfer membrane 336. Cells from the top layer of the dissociated tissue are gently picked up by vacuum, contact, absorption, and other methods to air-permeable, cell-impermeable, transfer membrane 336 located at the bottom of the multifunctional head 330 for sample transfer; this can be similar to vacuum assisted blotting when vacuum is used. The transfer membrane 336 limits the amount of transfer to preferably less than 20 um or less than 100 µm of tissue thickness and minimizes contamination by replacing the surface of the transfer membrane 336 with fresh membrane material between sequential sampling steps or cleaning. In some embodiments, an array of individually addressable vacuum/pressure or fluidic lines behind the membrane can be used to selectively apply vacuum to individually addressable subregions 337 of the membrane.

Figure 7B:
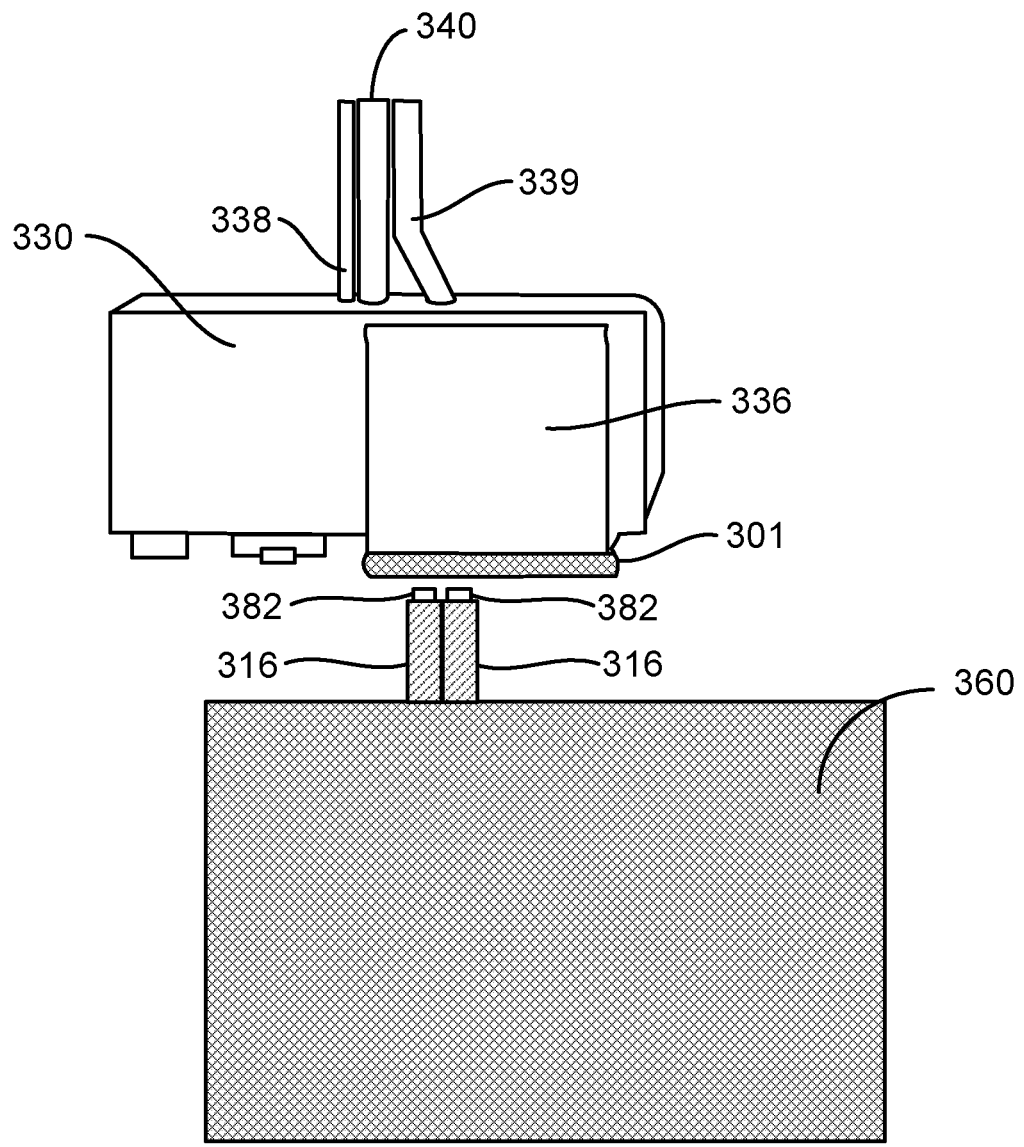
FIG. 7b shows an example of a multifunctional head with a transfer membrane about to transfer part of a specimen to an input device with two arrays of microchannels.

The multifunctional head 330 is then raised in the z direction, moved in the x and y direction as needed to dispense position 350, and lowered to contact the input device 360. FIG. 7b shows multifunctional head 330 about to contact input device 360. Input device 360 may contact all of the transferred specimen 302 or a subregion 150 of the transfer membrane 336. In a preferred embodiment, the input device 360 is an array of microfluidic channels. It will be apparent to one skilled in the art that the fluidics and microfluidics may be implemented in different forms including capillaries, molded microchannels, embossed microchannels, etched microchannels, and many other formats in many materials including plastics, glass, silicon dioxide, metals, and others. FIG. 7b shows a closeup of two ends of the input microchannels 382 held in connectors 316 about to contact the material transferred from specimen 301.

Figure 8A:
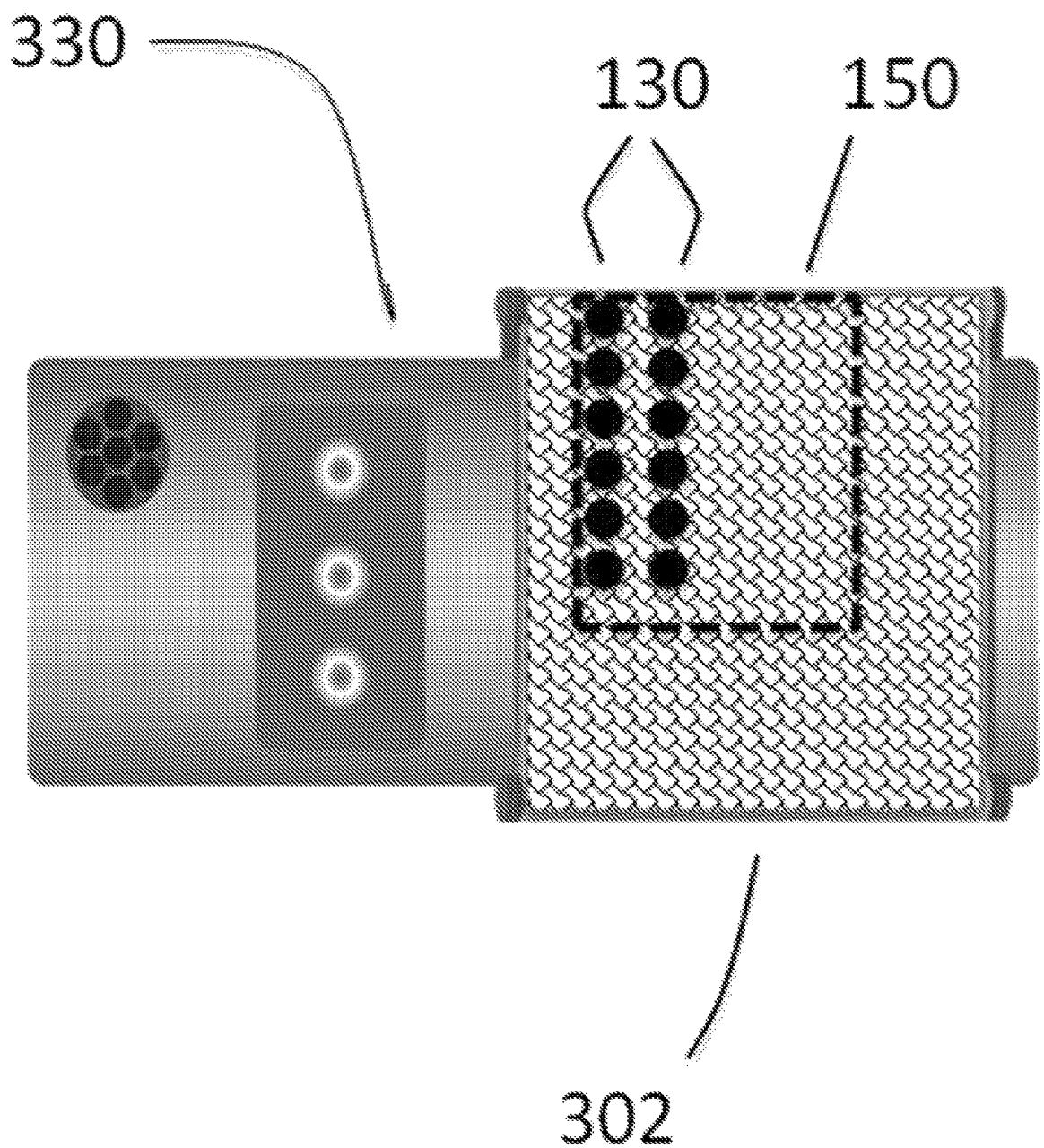
FIG. 8a shows a bottom view of a multifunctional head with a transferred specimen showing 12 microsamples transferred into input microchannels and illustrating a subregion.

FIG. 8a shows a bottom view of multifunctional head 330 that has transferred parts of specimen 302 onto transfer membrane 336 after contact by input device 360. Subregion 150 is outlined as the portion of the transfer membrane 336 that will be transferred into input device 360 in this example.

FIG. 8a shows 12 microsamples 125 from the spatial positions 130 (shown as black circles) have been transferred onto transfer membrane 336 and then into input microchannels 382. The transfer into input microchannels 382 may be any number of microsamples 125 at a time.

Figure 8B:
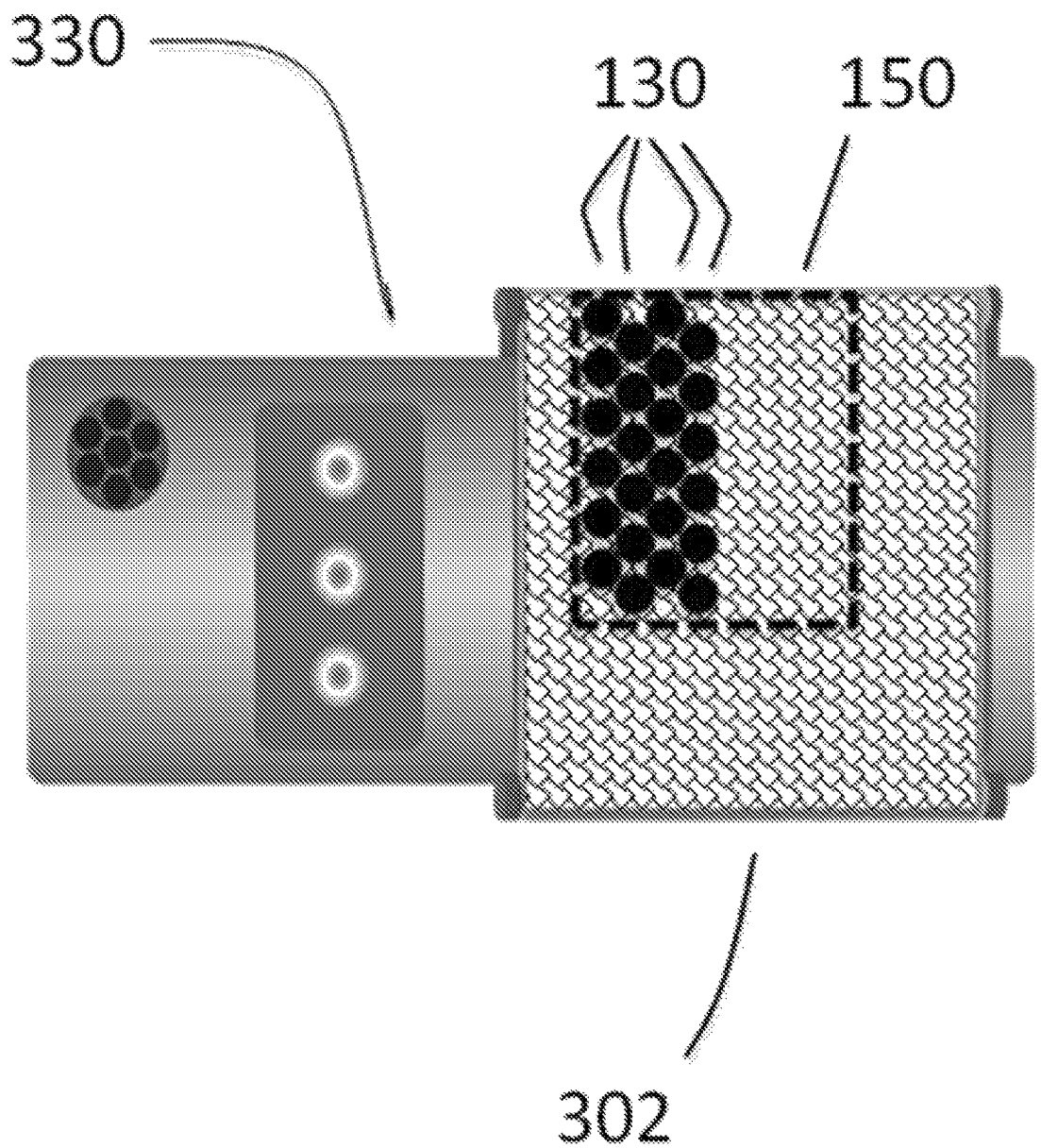
FIG. 8b shows a bottom view of a multifunctional head with a transferred specimen showing 24 microsamples transferred into input microchannels.

A 2×6 array of input microchannels 382 produces the pattern of microsamples 125 from spatial positions 130 shown in FIG. 8a in one input step. The second input step can produce a pattern of 24 microsamples 125 from spatial positions 130 that have been transferred as illustrated in FIG. 8b. Two more inputs steps would complete the input of 48 microsamples from subregion 150. In a preferred embodiment, the whole surface of transfer membrane 336 is used to transfer cells each time. In some embodiments the first pass of sampling microsamples 125 from subregion 150 of transferred specimen 302 may be followed by a second pass to transfer of cells from a second layer deep of transferred specimen 302 into input device 360. In another embodiment, a different subregion 150 of transferred specimen 302 may be input in the second transfer. In another embodiment, after input of a set of microsamples 125, the multifunctional head 330 can be moved to capture position 345 and another sample from specimen 301 collected from the same or different region of specimen 301 by transfer membrane 336; in some instances, additional optic information is gathered, the specimen treated with reagents by dispensers 335, or other activities may be performed before or after sampling specimen 301.

Input device 360 can adopt many different configurations. FIG. 8 shows the microsamples transferred to input device 360 that are circular in shape, like a capillary or other round microchannel would produce. The inside diameter (ID) can be matched to the size of the cells or material to be sampled. Capillaries could be used with, for example, 5 µm ID, or 20 µm ID, or 100 µm or 100s of µms to sample from different matrices. A 20 µm ID capillary can be used to sample mammalian tissue for single cells and input a microsample 125 from 30 µm deep for example; this microsample 125 could contain a single or multiple cells. A 100 µm ID capillary can be used to create microsamples 125 that could be 75 µm deep, for example, and might contain 10s or more cells. Other shapes than circular will enable sampling with different resultant patterns such as rectangular, triangular, and other shapes.

The number of samples collected from transfer membrane 336 will depend on the number of input microchannels 382 in input device 360. In some embodiments it is a single input microchannel 382 and in other embodiments two or more microchannels that may be arranged in one or more rows and columns. In some embodiments input device 360 collects microsamples 125 from the complete surface of transfer membrane 336 simultaneously.

The pattern of transfer of microsamples 125 from transferred specimen 302 is known and where in the subregion 150 input device 360 contacted transferred specimens 302 is known, therefore the spatial position 130 of where in the transferred specimen 302 each microsample 382 originated is known; therefore the Single Cell Spatial Analysis System 100 can keep track of the order of each microsample 125 until it is encoded with a marker or barcode to spatially encoded single cells 1000.

After encoding, as described below in detail, the microsamples 125, cells, or groups of cells, can then be pooled if desired. After sample preparation and analysis by an analytical method 1100, e.g., DNA sequencing, mass spectrometry, etc., the barcode is read out to produce Decoded Single Cell Spatial Data 1500. Decoding the barcode then determines from which microsample 125 each single cell orginated since known barcodes were added to ordered microsamples 125 in known order. Since the spatial position 130 of each microsample 125 is known, the three dimensional or two dimensional position of the single cells and groups of cells in multiple microsamples is known. Single Cell Spatial Analysis 2000 software analyzes the spatial position information with the spatial position 130 of each microsample 125 with Single Cell Analytical Data 1600 to produce Single Cell Spatial Information 3000.

Figure 9:
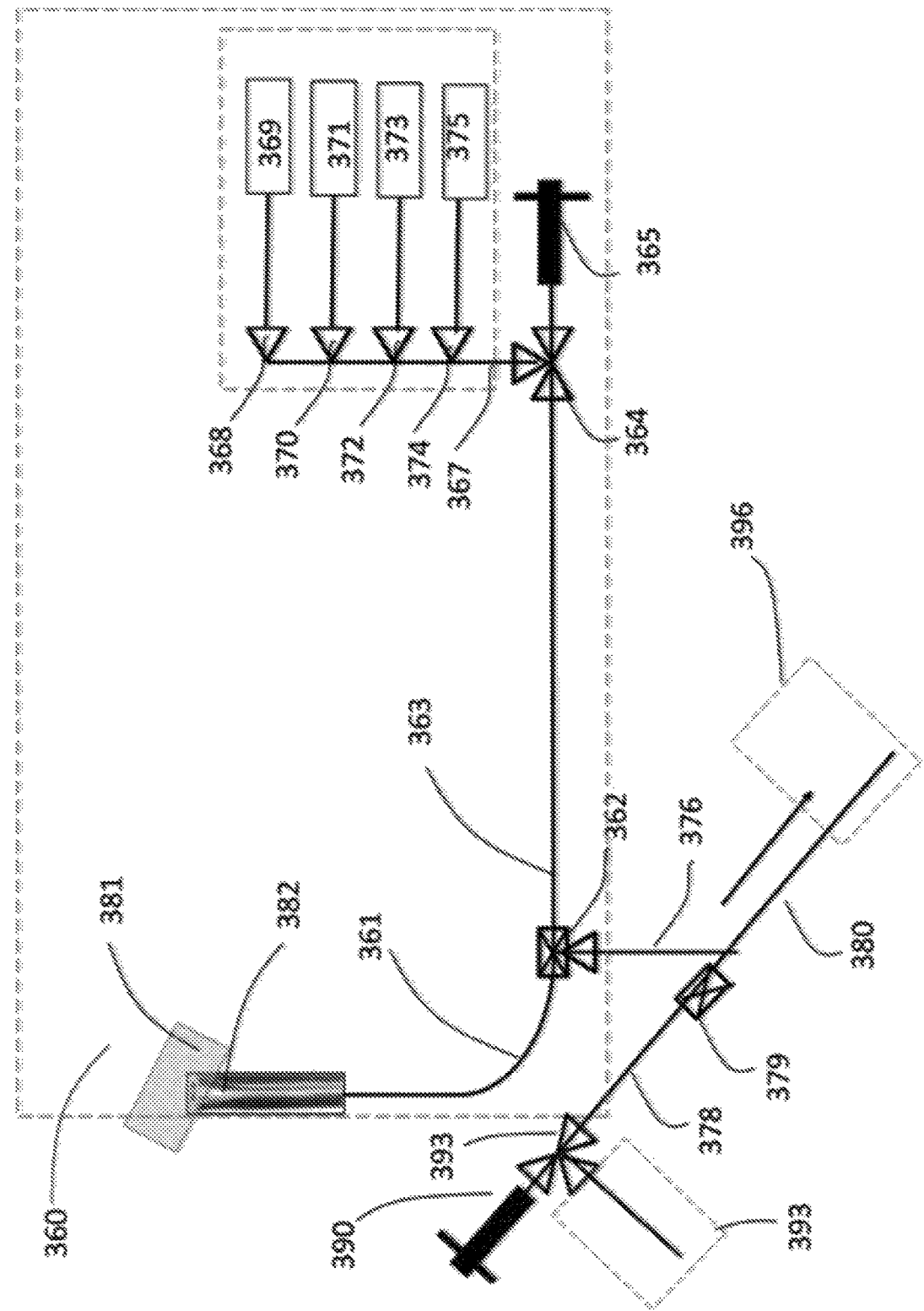
FIG. 9 shows an example of a single channel fluidic circuit of the input device to input a subregion of the specimen into a fluidic flow.

FIG. 9 shows one configuration of a single channel implementation of the input device 360. In this embodiment, the input device 360 connects of input microchannel 382 through two three-way valves to one or more syringe pumps. The end of input microchannel 382 contacts the transfer membrane 336 through an optional filter 381 such as a 50 µm stainless steel mesh to break up any clumps of cells and remove debri. Syringe pump 365 pulls reagents from reagent rail 366 using three-way valve 364 and fluidic channel 367 from one of the reagents, 369, 371, 373, and 375 with selection controlled by valves 368, 370, 372, and 374.

To input a microsample 125 into the end of input device 382, in one embodiment syringe pump 365 pulls buffer, e.g., 100 nL of PBS buffer, from buffer reservoir 369 through fluidic channel 367 by opening buffer valve 368 and three-way valve 364; a sample loop can be placed in between syringe pump 365 and three-way valve 364 or other locations as needed. Three way valve 364 can be replaced with valves such as 3 way or more way valves. After switching three-way valve 364, syringe pump 365 then pushes the buffer through three-way valve 364 through defining microchannel 363, three-way valve 362, input microchannel 361, the end of input microchannel 382 and through filter 381 to contact the portion of the transferred specimen 302 on transfer membrane 336. Pressure or liquid can be supplied through fluidic and pneumatic bundle 339 to individually addressable subregions 337 of the areas that match input device 360 to help elute microsamples 125 off of the transfer membrane 336 and into input device 360 as needed.

After changing the state of three-way valve 364, syringe pump 365 can pull the buffer and the transferred cells from transferred specimen 302, and moving it into input device 360, through filter 381, end of input microchannel 382, input microchannel 361, three-way valve 362, and into defining microchannel 363 which is flanked by three way valves 364 and 362 to create a microsample 125 in the fluidic stream. Three way valve 362 is then changed to connect defining microchannel 363 to connecting microchannel 376 and flow channel 380 and syringe pump 365 used to push the microsample 125 from defining microchannel 363 through three way valve 362 and connecting microchannel 376 and flow channel 380. Valve 379 may be closed to direct the flow in the direction of the arrow, towards the Sampler Encoder module 400 or other downstream processing.

Flow movement in flow channel 380 can also be accomplished using flow syringe pump 390 accessing flow reagent rail 391 through flow three way valve 393 to push fluids or gases to move the bolus(es) entrained in flow channel 380.

One or more optional bolus detector 396 can detect the edges of boluses using optical measurement, conductance, or other methods well known to one skilled in the art. The bolus detectors can be used to align the additional encoding beads downstream as needed.

The length of the bolus containing the microsample 125 can be defined by the volume in defining microchannel 363 which is flanked by three way valves 364 and 362, and the length and cross-sectional area of defining microchannel 363. In one preferred embodiment, the volume of the bolus is 100 nL, but volumes can range from subnanoliters to 10s of microliters or larger.

The bolus can be flanked by many materials including air, immiscible fluids (such as Fluorinert®; mineral oil; silicone-based oil; fluorinated oils; Droplet Generation Oil (Biorad, #1863005); emulsion oil (Life Technologies, Part No. 4469000); 73% Tegosoft DEC (Diethylhexyl Carbonate), 20% mineral oil, and 7% ABIL WE; 0.12% Span (v/v), 0.00325% Tween 80 (v/v), 0.0000125% Triton X-100 (v/v) in mineral oil; mineral oil containing 2% (v/v) ABIL EM 90 and 0.05% (v/v) Triton X-100 (Tanaka H, Yamamoto S, Nakamura A, Nakashoji Y, Okura N, Nakamoto N, Tsukagoshi K, Hashimoto M. Hands-off preparation of monodisperse emulsion droplets using a poly(dimethylsiloxane) microfluidic chip for droplet digital PCR. Anal Chem. 2015 Apr. 21; 87(8):4134-43. doi: 10.1021/ac503169h. Epub 2015 Apr. 7.) and other formulations) fluids with crowding agents such as polyethylene glycol that limit diffusion and interaction of the cells, fluids with reaction components, and many others. These materials can help define the placement of the bolus in the downstream flow, prevent mixing or dilution of microsample 125, provide reactants, or other functions. As used herein, the term "immiscible fluid" refers to a fluid that is immiscible with a solution containing a microsample.

Figure 10:
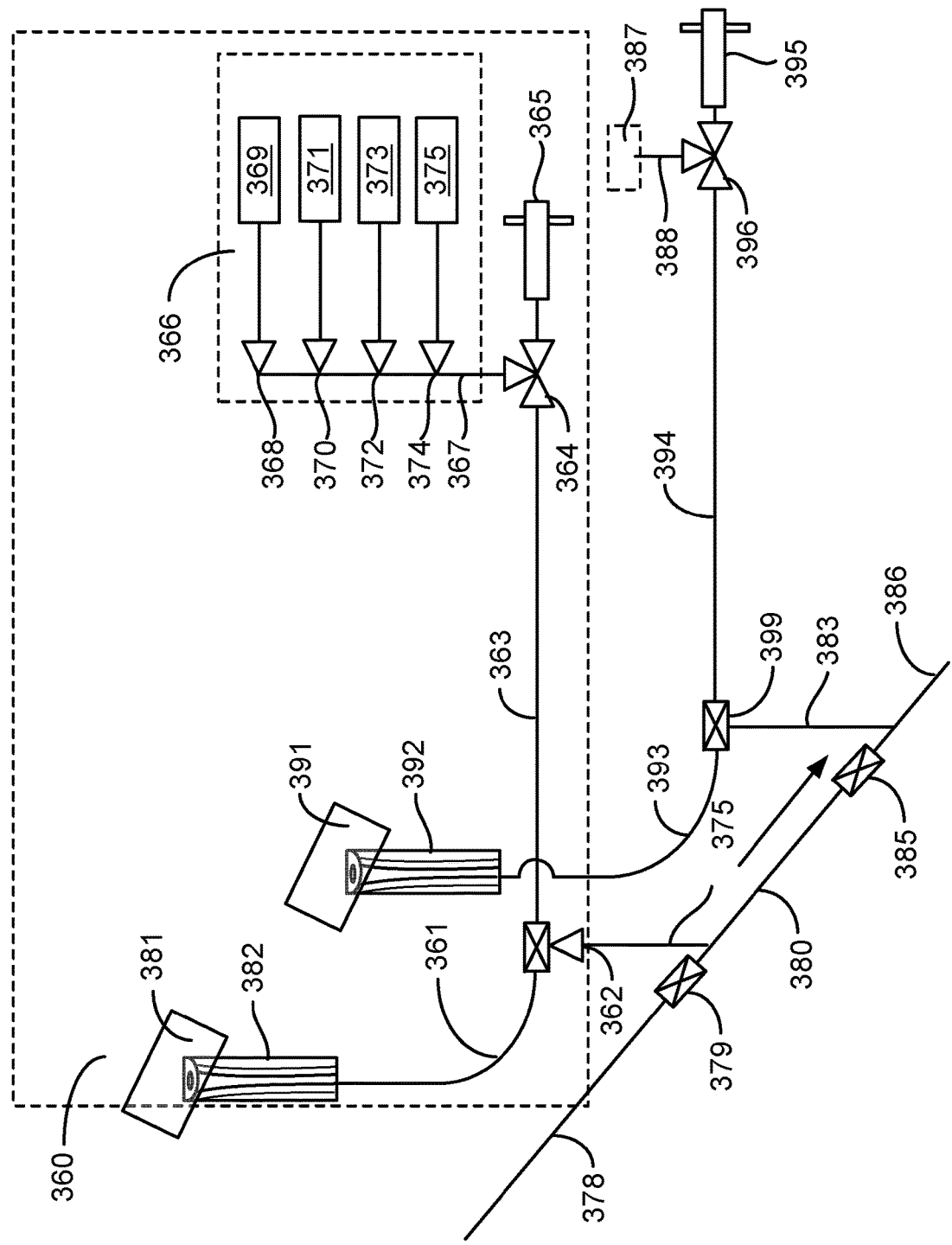
FIG. 10 shows an example of a two channel fluidic circuit of the input device that inputs two subregions of the specimen and combines them in known order into a single fluidic flow.

FIG. 10 shows an embodiment with the input device(s) 360 having two channels of input, through end of input microchannels 382 and 392. The two or more channels can be operated by two or more syringes 365 and 395 as shown in FIG. 10 or the microchannels can be ganged together to operate from a single syringe in parallel. Similarly the two channels may have separate reagent rails 366 and 387 or a single reagent rail. Multiple channels of input may have a single or reagent rails, for example, a bank of 16 input devices 360 could have two reagent rails, each of which services eight input channels. In some instances, different sets of reagents may be used in the different reagent rails, e.g., RNA sequencing preparation in one reagent rail and DNA targeted sequencing reagents in a second reagent rail. Many additional configurations are possible. It is within the scope of the present disclosure that one reagent such as 371 contain a dissociation solution to further loosen cellular attachments to extracellular matrix material. The dissociation solution or other solutions could be applied through the fluidics to a microregion of the sample on transfer membrane 336 before transfer of the microsample 125 or be used as the fluid to transport the microsamples to continue to dissociate any clumps. To separate boluses downstream flow microchannel 380 and output microchannel 386, one reagent can hold an immiscible fluid such as Fluorinert, mineral oil, Droplet Generation Oil (Biorad, #1863005) or other fluids. A cleaning reagent to remove debri, disinfect, flush,and other functions can be used in reagent 375. The number of reagents may be as low as one and be as large as needed for the application without limitation.

In some embodiments the reagents are in syringes operated by syringe pumps. In another embodiment, the reagents are in pouches, tubes, wells, or other containers and are moved by a pump or micropump such as a piezopump, e.g. a Bartels mp6, Dolomite Piezoelectric Pump 3200138, or others. In some embodiments, the reagents and other components of the Single Cell Spatial Analysis System 100 may be in cartridges 4000 that are readily changed by non-specialists.

When transfer membrane 336 is moved against the input device 360, if two or more end of input microchannels 382 and 392 are used, they may be directly adjacent or with known spacing. In a preferred embodiment the ends are adjacent. When the input microchannels are not adjacent, the transfer membrane 336 can be moved against the input device 360 for multiple samplings of the transfer membrane 336. For example, if the input device has microchannels of 20 µm ID and spacing between microchannels of 200 µm, then the multifunction head 330 could move ten times to pull in samples from the complete subregion 150 if it is linear. Similarly, multifunction head 330 could raster or use other patterns to insure that all of the transfer membrane 336 is sampled when desired.

Microsamples 125 for multiple input microchannels may be processed into defining microchannels 363 and 394 in parallel or independently. Similarly, to move the microsamples 125 downstream of flow channels 378 and 380 to be output into microchannel 386, three way valves 362 and 399 are changed to connect defining microchannels 363 and 394 to connecting microchannels 376 and 383 to flow channels 380 and output microchannel 386. Valve 379 may be closed to direct the flow in the direction of the arrow, leading to the Sampler Encoder module 400 or other downstream processing. In one embodiment, the microsample 125 in defining microchannel 394 is pushed by syringe pump 395 into output microchannel 386 and then the upstream microsample 125 in defining microchannel 363 is pushed by syringe pump 365 into flow channel 380 to place the two samples in a known order, separated by the volumes and initial material in connecting microchannel 376 and flow channel 380. In another implemention the microsamples 125 may be moved simultaneously.

To dispense microsamples 125 into the microfluidic stream in a known order, the multifunctional head or other device moves the transfer membrane 336 to a dispense position where released cells are pulled in the order of the original 2-D spatial position into end of input microchannels 382 and 392 on input device 360, driven initially by syringe pumps 365 and 395. For example, with an array of a column of microchannels on the input device, the top row could be input column by column. Boluses of air, immiscible fluids, or other gases or liquids can be introduced to separate microsamples 125 as needed. Cells are aligned in order and output in a single fluidic or microfluidic stream into the Spatial Encoder module 400.

i. One Channel Spatial Sampler Example.

In one implementation, a transfer device with a membrance with a single microchannel can be implemented using a single capillary, e.g., 20 µm ID capillary (Polymicro Technologies), which in a prefered embodiment is epoxied in a fiberoptic-like capillary (FROLC) connector with a membrane attached to one end, held in a moveable fixture; the other end of the capillary is attached through a three way valve using a FROLC connector to defining microchannel 363 of 100 nL to reagent rail 366 and syringe pump 365 as a vacuum and pressure source. The single 20 µm ID capillary may be able to sample about 1 nL from specimen 301.

Figure 11:
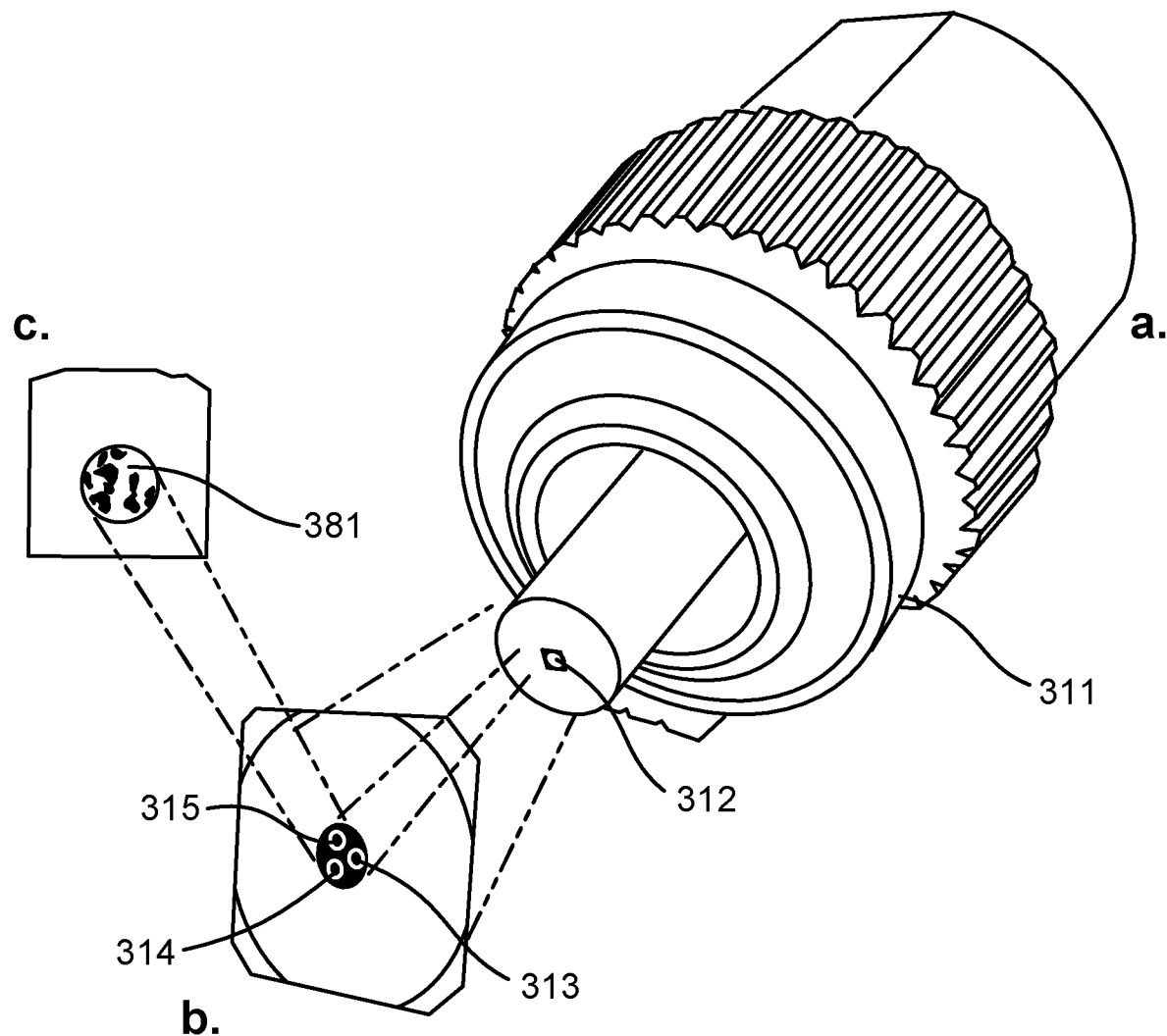
FIG. 11a shows a capillary connector, valve, and router.
FIG. 11b shows three 75 um ID capillaries mounted in a FC connector.
FIG. 11c shows a single capillary in a FC connector covered with filter paper as a transfer membrane.

The FROLC connectors, shown in FIG. 11, are true zero dead volume connectors and can join two or more capillaries to one, and be used as multiway microvalves. (Jovanovich, S. B. et. al. Capillary valve, connector, and router. Feb. 20, 2001. U.S. Pat. No. 6,190,616; Jovanovich; S. B. et. al. Method of merging chemical reactants in capillary tubes. Apr. 22, 2003. U.S. Pat. No. 6,551,839; Jovanovich, S., I. Blaga, and R. McIntosh. Integrated system with modular microfluidic components. U.S. Pat. No. 7,244,961. Jul. 17, 2007.) are incorporated by reference and their teachings which describe the FROLCs and details of FROLC connectors, including their use as multiway valves, routers, and other functions including microfluidic circuits to perform flowthrough reactions and flow cells with internally reflecting surfaces. FROLCs can be made by using a fiberoptic FC-, or other fiberoptic connectors 311 with cleaved capillaries plugged with wax or other materials, and then inserted into face 312, epoxy filled, polished to a dome like a fiber optic connector, and the wax removed. A spring in the connector provides compression to seal capillaries for liquid flow at >9,600 psi. Rotation of the connector can change the orientation of, for example, three capillaries to rout sample streams into any of three output capillaries. FROLC connectors can also be made from other designs than fiberoptic connectors in a matter that allows leak-free connection between one or more capillaries or microchannels. A FROLC connector is shown in FIG. 11a with three capillaries 313, 314, and 315, that are visible in FIG. 11b.

Membranes such as transfer membrane 336 or filters on input devices, such as a 20-40 um range filters or other materials can be mounted to the FC stainless surface over the end of the capillary in the FROLC (FIG. 11c). A collar to simplify mounting the membrane can be made with 3-D printing or other methods. Collection and dispensing requirements of different membranes can be evaluated for the ability to 'grab' the top layer from loosened tissue and to dispense into the input device 360.

Membrane filters can be from commercial sources with different characteristic, such as material, coating, and pore size. The amount of vacuum to pickup and hold, pressure to dispense, efficiency in pickup and delivery, and the depth of tissue picked up can be optimized for different membranes and specimens; the part of the FC connector without the capillary can be used as a control region when evaluating transfer membrane 336 candidates. Membranes can be examined under brightfield and, after fluorescent cell stains, with fluorescence microscopy for testing of capture and dispensing. Selected samples can be assayed with real-time PCR to develop the process and the requirements for repeatedly collecting cells onto a surface and then dispensing using a single capillary, and provide first insight into repeated sampling to generate 3-D spatial information.

To input a microsample 125 from transfer membrane 336 in a single channel implementation using a capillary held in a FROLC connector 311 for the input device 360, a microsample 125 can be pulled into a single channel with a capillary (e.g., 75 µm ID) with FROLC connectors on both ends. One end will contact the transfer membrane and might optionally have a filter or mesh on its outer surface to breakup cell clumps; the other end is a FROLC three way valve that is in turn attached to the defining microchannel 363 which can have FROLC at both ends with the FROLCS used as three way microvalves to connect at the upstream end to the input device end 382 and to a capillary as the connecting microchannel 376 and the other end of defining microchannel 363 through a FROLC three way valve to a syringe pump 365 and a reagent rail 366. Buffer, ~100 nL, will be delivered to the tip of the capillary and manually contacted to the transfer membrane area of the multifunctional head 330. Transfer protocols can be optimized for requirements for pulling samples into the input device, timing, and fluidic process.

The defining microchannel 363 can readily be a volume such as 100 nL, or larger or smaller. A 100 nL is an approximately 7 cm long bolus in a 40 µm ID capillary or 2.5 cm long bolus in a 75 µm ID capillary—sufficient length to be defined between two FROLC or other microvalves. If needed, the 100 nL sample can have immiscible fluid added to create a larger volume to manipulate. The ability to input a sample and then rout into the microfluidic flow can be tested with fluorescent beads and then cell suspensions. Multiple samples of alternating types (i.e., rat cells followed by murine cells) can be input and output to the fluidics stream to measure cross contamination rates. Cleaning solutions in reagent 375 can be used. In a single channel example, the connecting microchannel 376 can be used as the output line for the Spatial Sample module (microchannels 378 and 380, and valve 379 are not used). In addition to using a capillary, in a single channel implementation, it is within the scope of the present disclosure to use microchannel(s) that may be injection molded, milled, or otherwise made and covered with a material such as a heat-sealed membrane.

ii. Multi-Channel Spatial Sampler Example.

If neither pressure is needed to dispense from the membrane nor is continued vacuum needed to hold samples onto the membrane, the sample transfer portion of the multifunctional head 330 simplifies to a transfer membrane 336 with vacuum control. If dispensing requires pressure sequentially applied to individual subregions of the membrane, then to achieve high throughput the transfer device can be an array device that input collects and dispenses multiple samples at a time into a 'mirrored' input format, i.e., if the transfer device used 8×12 channels, the input device 360 would use 8×12 channels.

Figure 12:
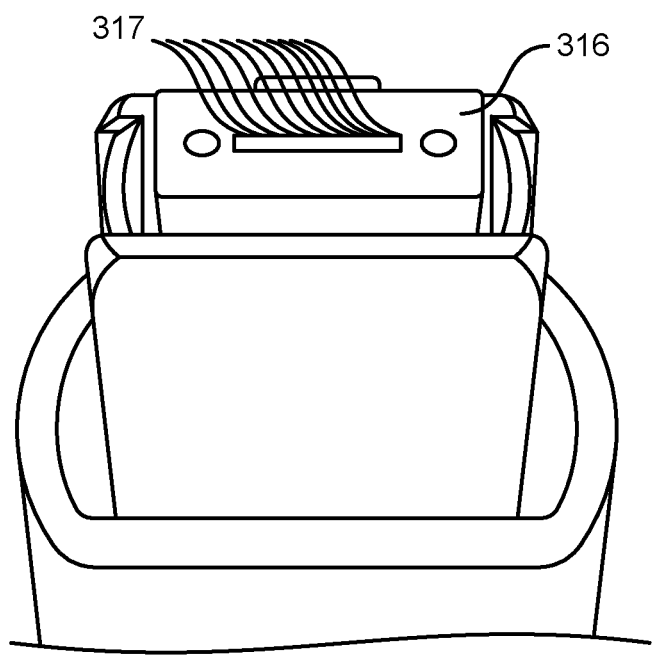
FIG. 12 shows 12 200 um OD capillaries arrayed in a linear connector.

FIG. 12 shows 12 capillaries 317 arrayed in a linear FROLC connector 316. For transfer, in one embodiment, the transfer region of the multifunctional head will have a membrane in front of the 12 capillaries to collect samples, each capillary individually addressable to deliver pressure to dispense the 12 microsamples 125 if needed. The input device 360 can be be another linear array of 12 capillaries 317 in inear FROLC connector 316, covered with a 30 µm filter, connected to a ganged syringe pump an array of 12 fluidic circuits. In other embodiments, the transfer region of the multifunctional head does not have a membrane in front of the 12 capillaries to collect samples.

a. Spatial Encoder Description.

The Single Cell Spatial Analysis System Spatial Encoder module 400 inputs the ordered microsamples 125 which may contain single cells or groups of cells from the Spatial Sampler module 300 using the Spatial Sampler output such as output microchannel 386 as an input to the Spatial Encoder module 400. The spatial encoder subsystem can place the microsamples in a sequential ordered arrangement in a fluidic stream. This sequential arrangement is referred to as a train, and microsamples in a train are said to be entrained. In a preferred embodiment for nucleic acid encoding, adds beads with known barcodes to correlate with the original spatial information into boluses, creates microdrops, (nanodroplets in some implementations, or boluses in other implementations), preferably with one or less cells per nanodroplet. A bolus is typically elongate in shape, while a nandroplet is typically spherical. A bolus typically has a volume of at least 3 microliters. A nanodrop typically has a volume of no more than 3 microliters, e.g., about 1.5 microliters. In a preferred embodiment, the Spatial Encoder module 400 outputs single cells with spatial barcodes in nanodroplets or boluses to the Spatial Librarian Subsystem 500.

Figure 13A:
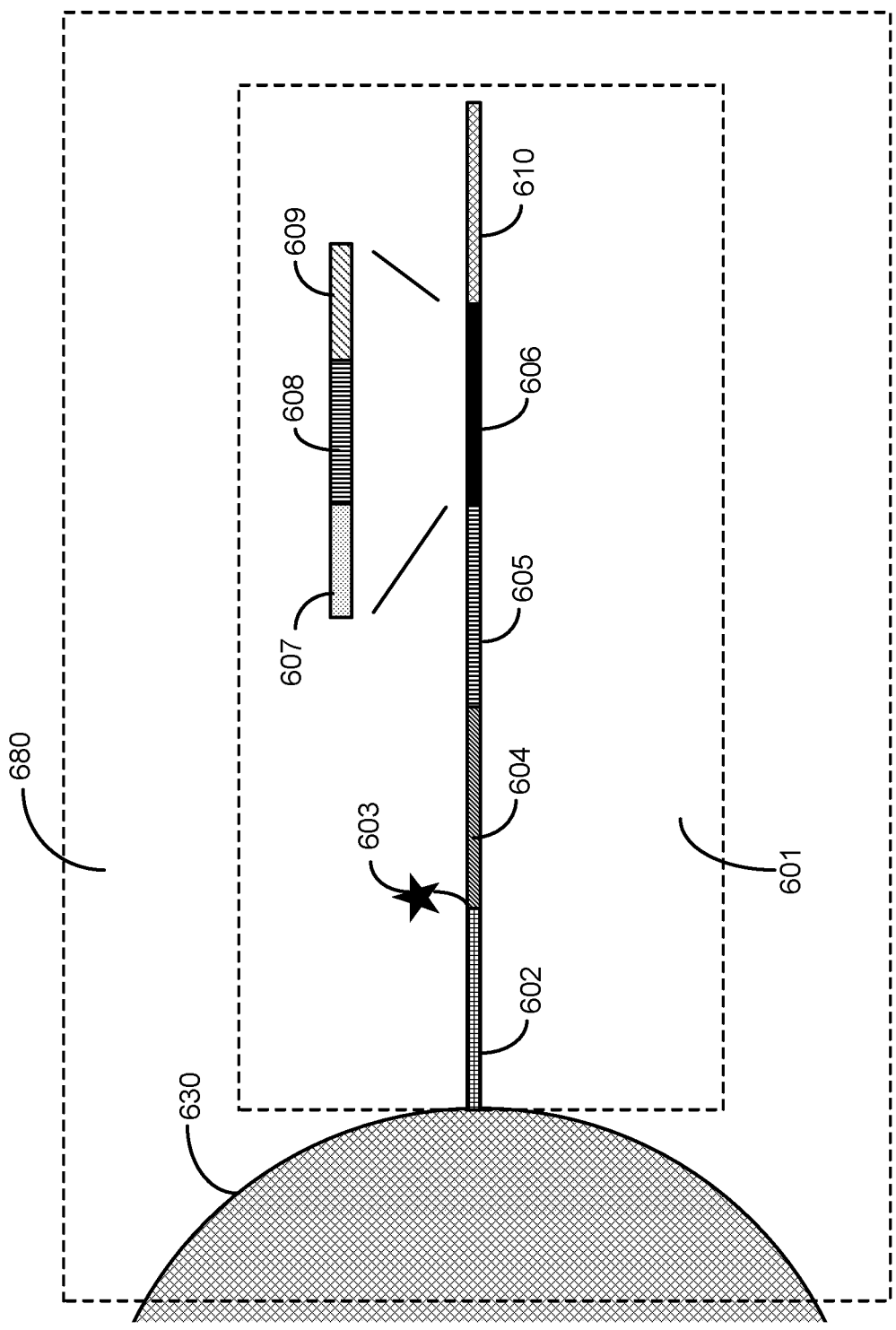
FIG. 13a is an illustration of a bead with an oligonucleotide attached that contains a spatial DNA barcode.

One embodiment of spatial barcoding is to use beads with oligonucleotides with spatial barcodes 680 is illustrated in FIG. 13a. The beads with oligonucleotides with spatial barcodes 680 can be paramagnetic beads, agarose beads, or others, and have surface chemistry optimized for the nucleic acid capture and subsequent chemistries. Oligonucleotides with spatial barcodes 601 can be generated by synthesis using standard commercially available phosphoramide or other technology. In one embodiment, the oligonucleotide has a cleavable linker 602, attached to an amplification primer 604 with fluorescent label 603, a sequencing primer 605, barcode region 606, and capture region 610. The barcode region is comprised of a spatial barcode 607, cellular barcode 608, and molecular barcode 609. In one embodiment the spatial barcode 607 can be 5 nucleotides long to provide 1,024 barcodes for spatial resolution. Cellular barcodes 608 can be 6 nucleotides, or other lengths, and synthesized by split-pool synthesis, and molecular barcode 609 can be 8 nucleotides synthesized by degenerate synthesis; the cellular barcodes 608 only need to identify cells from within a single microsample 125 since each microsample is encoded with a spatial barcode. In a preferred embodiment, each spatial barcode 607 is unique for each set of microsamples 125 that are analyzed together. In other embodiments, spatial barcode 607 can be shared between microsamples 125 and then resolved bioinformatically using cellular barcode 608 to sort and cluster by cells to resolve spatial barcode ambiguities. Spatial, cellular, and molecular barcodes can be of different lengths or in different orders, or dispersed among other elements of the oligonucleotide with spatial barcode 50 without limitation.

Figure 13B:
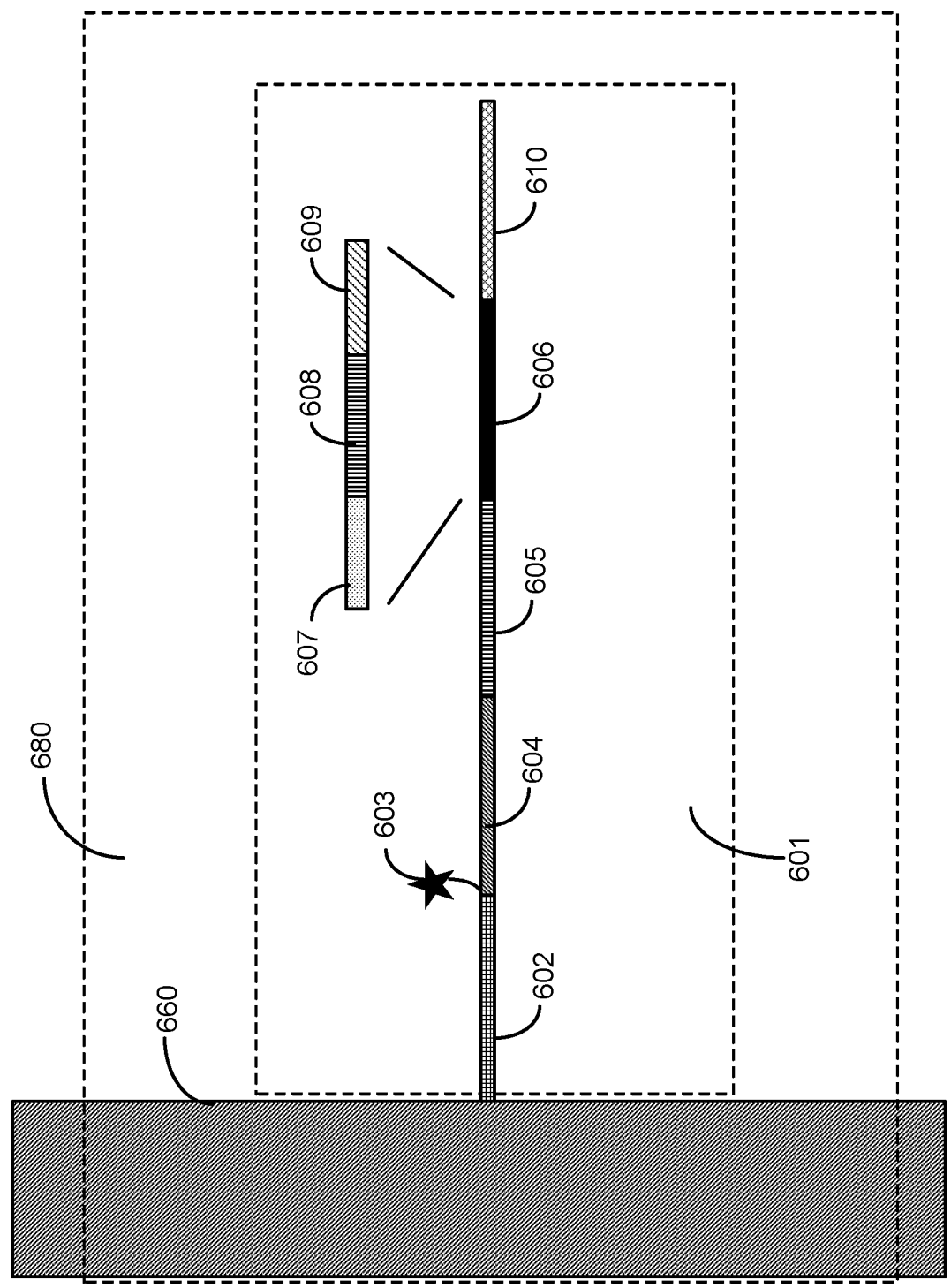
FIG. 13b is an illustration of a surface with an oligonucleotide attached that contains a spatial DNA barcode.

Another embodiment of spatial barcoding is to attach oligonucleotides with spatial barcodes 601 to surfaces 660 as illustrated in FIG. 13b, or flowcells 670. The surface 660 then can be used in similar ways to the beads. It will be obvious to one skilled in the art that surface 660 could be assembled into a flow cell.

The oligonucleotides, such as amino-modified oligonucleotides, can be initially attached to commercially available paramagnetic beads 630 by covalent crosslinking and may include a cleavable linker bond (Ju. J. et. al. U.S. Pat. No. 9,133,511. Sep. 15, 2015.), (Knapp D. C. et. al. Bioconjug Chem. 2010; 21(6):1043-55.), (https://www.click-chemistrytools.com/products/click_chemistry_toolbox), (Olejnik J. et. al. Nucleic Acids Res. 1996; 24(2):361-6.). Fluorescent probes can be attached to the oligonucleotide distal from the bead and cleavable bond or alternatively fluorescent nucleic acid base analogs can be used such as 2-Aminopurine (Wilhelmsson, Quarterley Reviews of Biophysics, 43, 2, 2010, 159-183). The cleavage of labeled oligonucleotides can be used for assay development since the oligonucleotide can be analyzed by fragment sizing on CE with the fluorescent tag to give the distribution of sizes to assess library quality.

Figure 14:
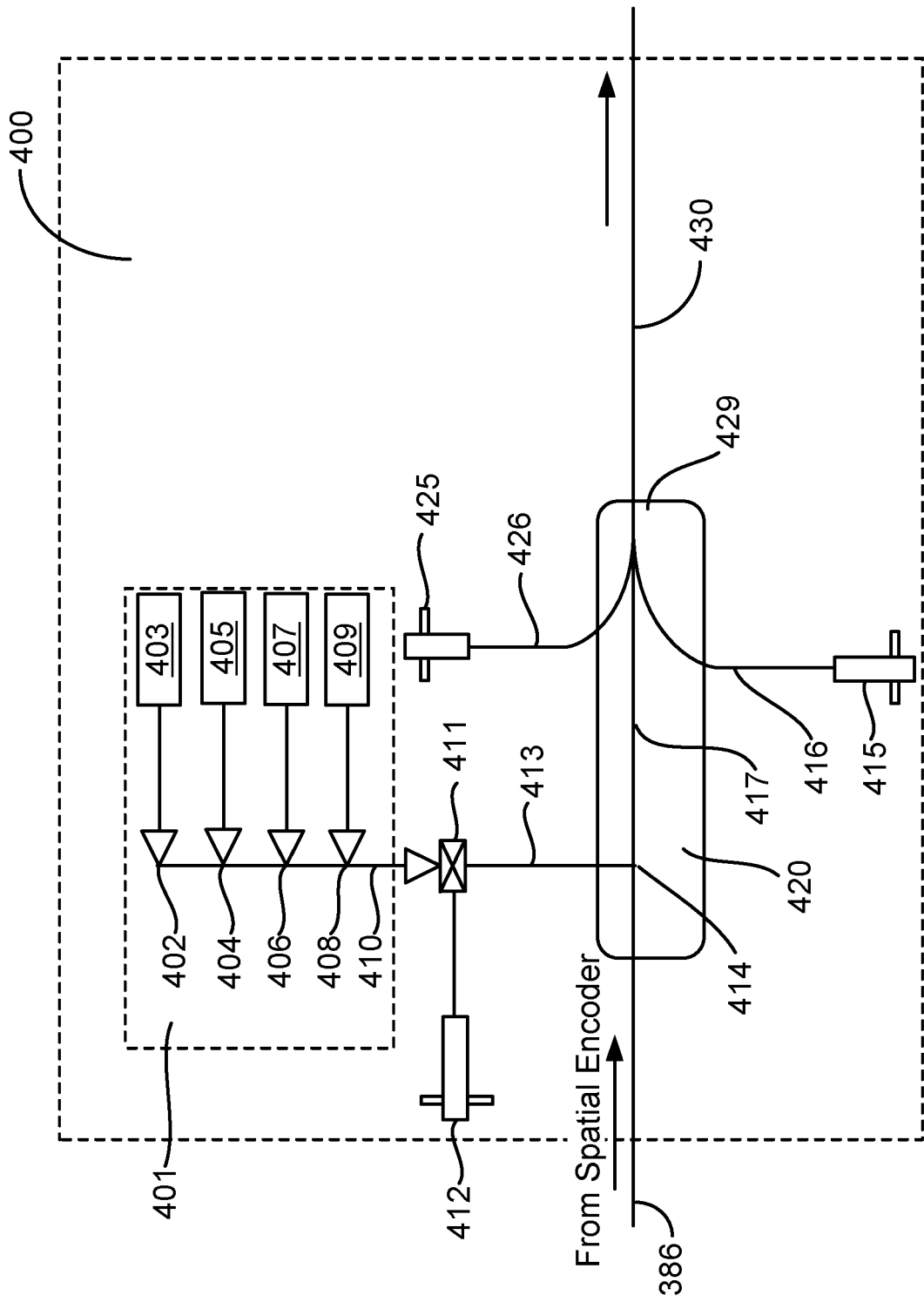
FIG. 14 shows a single channel fluidic design of a Spatial Encoder module that has four spatial barcodes.

The hardware and software of the Spatial Encoder module 400 must deliver a set of beads with a unique, known, spatial barcode 607 to each microsample 125. Referring to FIG. 14, the Spatial Encoding fluidic delivery can use a spatial barcode reagent rail 401 to access beads each with a single spatial barcode, for example 403, 405, 407, and 409, controlled by spatial barcode reagent rail valves 402, 404, 406, and 408 respectively, to deliver reagents through by spatial barcode fluidic channel 410 to spatial barcode syringe pump 412. It is within the scope that the spatially barcoded beads will scale to 1,024 or greater number of spatial barcodes per run for the Single Cell Spatial Analysis System. Spatial barcode three way valve 411 and spatial barcode reagent rail 401 can be implemented with many other variations, including having spatial barcode reagent rail valves 402, 404, 406, and 408 each being multiway valves, such as 8-way valves that in turn access 8 sets of spatial barcode reagents, or additional valves be added to the reagent rail. The multiway valves can be FROLC or other microvalves, molded microfluidic valves, valves on microchips, or other embodiments. An alternative approach is an ordered series of boluses of beads with different spatial codes that are merged with the microsample 125 boluses in known order.

As microsamples 125 are moved from Spatial Sampler output, such as microchannel 386, reagent rail syringe pump 412 and spatial barcode reagent rail 401 can select a reagent of singly spatially barcoded beads, such as beads all with a single spatial barcode 403, and delivers a bolus of beads 403 through spatial barcode connecting channel 413 to spatial encoder junction 414 to merge with the microsample 125 in spatial encoder microfluidic device 420. Optical, conductance, or other sensors can be incorporated as needed to detect the microsample 125 in the bolus and coordinate the addition of the spatially barcoded beads to the bolus.

The bolus then passes through spatial encoder microchannel 417 to nozzle 429 where an immiscible fluid such as Fluorinert, Droplet Generation Oil (Biorad, #1863005), or other solutions can be added by nanodroplet generation syringe pumps 425 and 415 to the bolus to produce nanodroplets, preferably 1.5 nL, and sent down spatial encoder output microchannel 430 as output from the Spatial Encoder. Nanodroplet generation syringe pumps 415 and 425 can also be combined into one syringe pump that has two microchannels 416 and 426 that split in two from nanodroplet generation syringe pump output to join the microsample 125 with barcoded bead bolus from either side to produce nanodroplets, eliminating the need for a second nanodroplet generation syringe pump. Nozzle designs and circuits are incorporated by reference (Macosko E. Z. et. al. Cell. 2015; 161(5):1202-14.) (Klein A. M. et. al. Cell. 2015; 161(5): 1187-201.) (Geng T. et. al. Anal Chem. 2014; 86(1):703-12).

In an alternative embodiment, the microsample 125 bolus with the added spatially barcoded beads are processed as a bolus without the formation of nanodroplets. In this approach, the bolus may be preferably less than 5 nL, or 10 nL, or 25 nL, or 100 nL, or 250 nL, and 10,000 microsamples 125 may be less than 2.5 mL.

Figure 15:
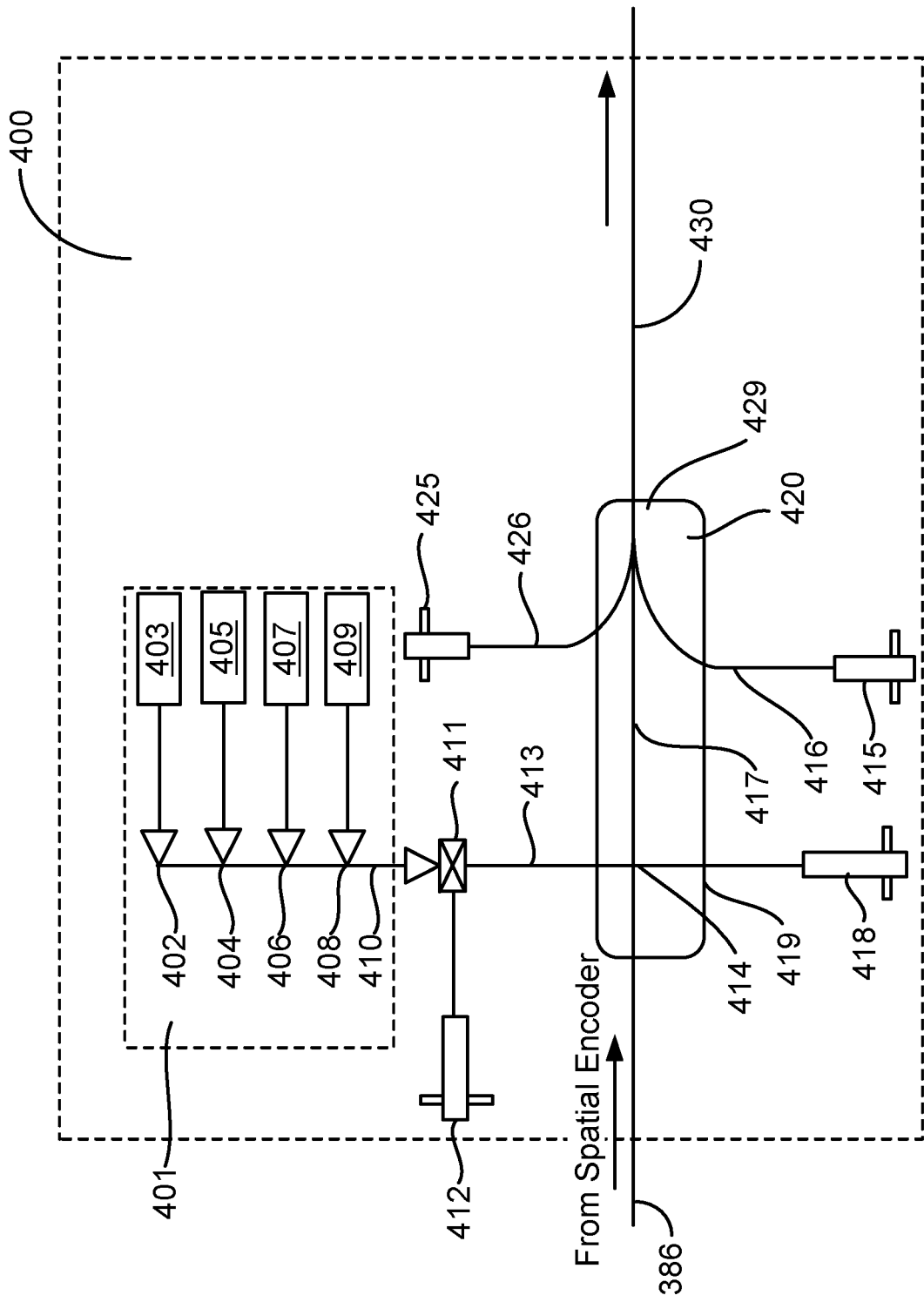
FIG. 15 shows a single channel fluidic design of a Spatial Encoder module with a spatial encoder reagent syringe pump that can add additional reagents to a bolus or a microsample.

In one embodiment, single channel fluidics are used. Referring to FIG. 15, a bolus of, for example, 100 nL of beads with one spatial code are added in junction 414 to the, for example, 100 nL of microsample 125 in output microchannel 386 and lysis and/or reaction mixtures, such as lysis/reverse transcriptase mix, added separately through spatial encoder reagent syringe pump 418 and reagent connecting microchannel 419.

Monodispersed nanodroplets from single cells with spatially coded beads with lysis and/or reaction mixtures, e.g., lysis/RT mix for RNA-Seq, lysis/restriction mix for DNA sequencing, are then be produced using a nozzle 429 (Macosko E. Z. et. al. Cell. 2015; 161(5):1202-14.) (Klein A. M. et. al. Cell. 2015; 161(5):1187-201.) (Geng T. et. al. Anal Chem. 2014; 86(1):703-12.) and output through spatial encoder output microchannel 430. As needed, the geometry and flow rates can be altered to adjust size and flow rates to produce a Poisson distribution of single cells with each nanodroplet preferably having a spatially barcoded bead. In other embodiments, the bolus from the Spatial Sampler module 300 is physically separated by structures, volumes, or surfaces, for example, by placing the bolus into a microtiter or smaller well or tube. The Spatial Sampler module 300 output can be used to be physically dispersed onto the surface of a material comprised of agar, membranes, arrays of beads, microscope slides, flow cells, and others. The physical dispersion can be by moving the surface under a capillary or other flow, by printing with a microarray pen, by piezospraying, electrowetting, microfluidics, or other methods. The physically separated microsample 125 bolus can be dispersed such that, for example on the surface of agar, all cells are far enough apart to be processed as single cells.

In one embodiment, spatial encoder reagent syringe pump 418 adds a low melting temperature agarose to encapsule the nanodroplet with heated liquified agarose (Geng T. et. al. Anal Chem. 2014; 86(1):703-12.) during the formation of nanodroplets. Once cooled, the agarose can be used as a barrier permeable to low molecular weight components, such as reaction components, but not to high molecular weight components such as nucleic acids when it is cooled. The use of agarose to encapsulate the reactions enables multiple sequential reactions or manipulations in a row to be performed in the nanodroplet.

b. Spatial Librarian Subsystem Description

In one embodiment, the Spatial Librarian Subsystem 500 receives the output of the Spatial Preparation Subsystem 200 and can process the microsamples 125 including single cells and groups of cells from a single spatial position 130 of the specimen with a spatial barcode added. The Spatial Librarian Subsystem 500 can perform enzymatic reactions, chemical reactions, and purifications, quality control, and other functions.

Figure 16:
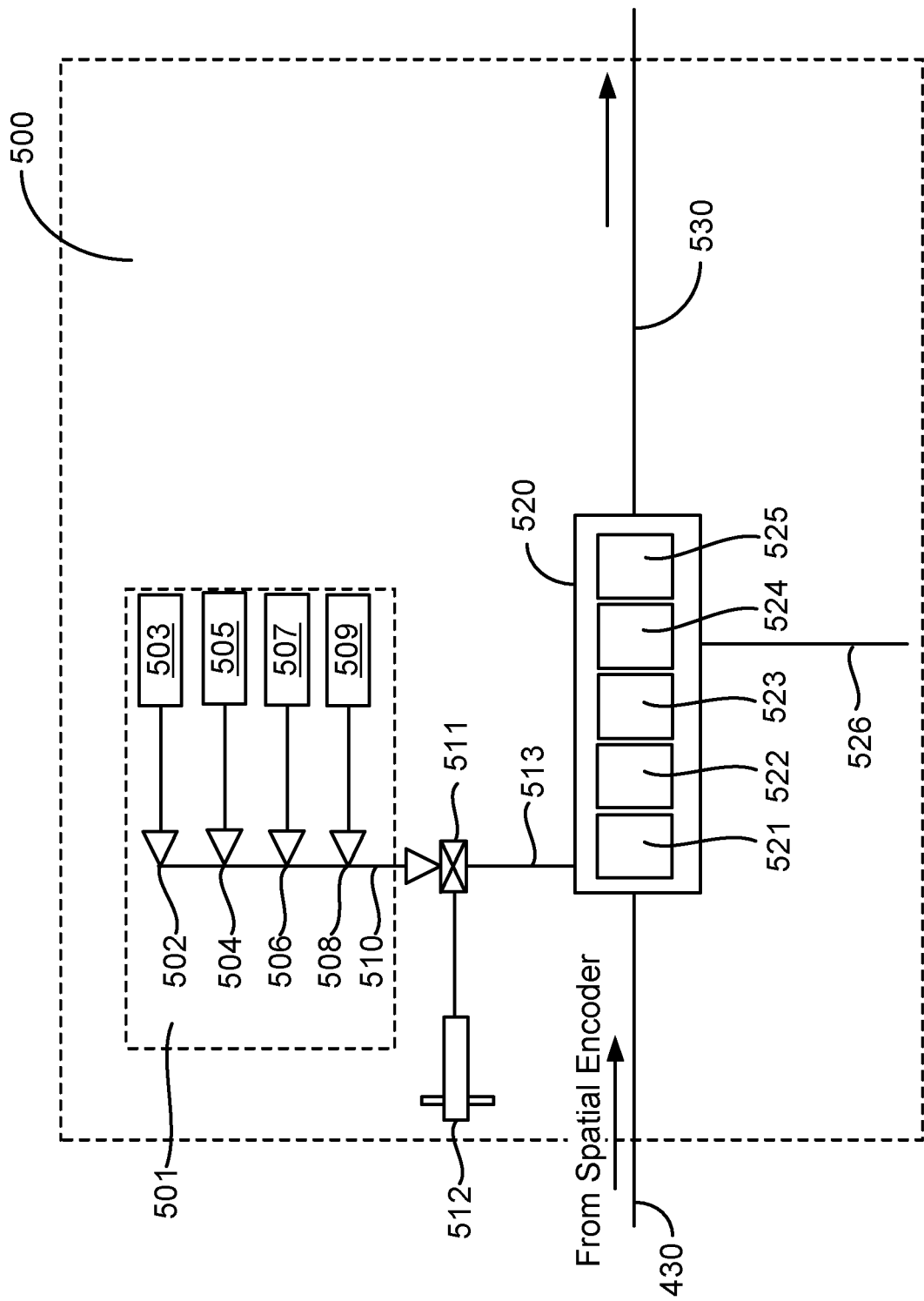
FIG. 16 illustrates a Spatial Librarian embodiment with a reagent rail and reaction chamber with temperature control, optical interrogation, paramagnetic bead purification, and quality control analysis functionality.

Referring to FIG. 16, in one embodiment, the output from the Spatial Encoder module 400, e.g., output microchannel 430, is input into the Spatial Librarian Subsystem 500 to reaction device 520. In one embodiment, the microdrops (e.g., nanodroplets or boluses) are pooled in reaction chamber 523 and reagents added from spatial librarian reagent rail 501 accessing spatial librarian reagents 503, 505, 507, and 509 through spatial librarian valves 502, 504, 506, and 508 respectively to allow access through spatial librarian reagent rail connecting microchannel 510 with spatial librarian syringe pump 512 and spatial librarian three-way valve 511. Reagents can be added to reaction chamber 523 to mix with pooled microdroplets. In other embodiments, reaction device 520 is a flowthrough system. Waste can be flowed into waste line 526 as needed. Temperature can be controlled including thermal cycling by temperature control device 521 which can include sensors and heaters well known to one skilled in the art including resistive heating, infrared heating, flowing air or water, and other methods. Optional optic device 522 can monitor reactions such as quantitative polymerase chain reaction (qPCR), reverse transcriptase-PCR, Raman spectroscopy, or other optical measurements including fiberoptic delivery and collection of light from lasers, filters, imaging devices such as CCD and CMOS, and other optical methods. Quality control device 525 can assess the quality of the processing integrated devices such as capillary electrophoresis with laser induced fluorescence to determine the amount and the size distribution of fragments in the library, mass spectrometry, Raman, electrochemistry, or other devices.

When needed, the spatial librarian can break or create emulsions by accessing reagents on spatial librarian reagent rail 501. To break an emulsion, many standard methods can be used including adding isobutanol ("Idiot-proof emulsion PCR", Lab Times, 1-2011, p50); isopropanol and detergent buffer (10 mM Tris pH 7.5, 1 mM EDTA pH 8.0, 100 mM NaCl, 1% (v/v) Triton X-100, 1% (w/v) SDS); water-saturated diethyl ether; salt including sodium pyrophosphate; or demulsifiers such as Dow Corning® DM4 Demulsifier or others can be added. In an alternative approach, an organic extraction solvent, selected from the group consisting of: butanol, octanol, hexanol and chloroform,is added to an aqueous phase of a breaking solution includes sodium dodecyl sulfate (SDS) or phosphate buffered saline (PBS), further including an inorganic salt in the aqueous phase prior to forming the breaking solution wherein the inorganic salt is selected from the group consisting of potassium chloride, potassium acetate, sodium chloride, sodium acetate, lithium chloride, lithium acetate, Na2SO4, potassium carbonate, ammonium sulfate, and ammonium acetate (Jeffrey Sabina, Ilya Zlatkovsky, Rachel Kasinskas, "Methods and kits for breaking emulsions" WO 2012138926 A1, Published Oct. 11, 2012) or. The solution can be allowed to separate by gravity and then the bottom phase collected with spatial librarian syringe 512 with connection line 513 positioned in the bottom of reaction chamber 523. The top phase can be discarded through waste line 526. In an alternative embodiment, a centrifuge device is included in reaction device 520 to separate emulsion phases, with a pipetting device to withdraw the aqueous phase from the bottom of the centrifuge tube.

To create an emulsion, the appropriate emulsion oil is selected by spatial librarian reagent rail 501 and added to the reaction chamber 523 with a vigorous back and forth motion of the solution in the reaction chamber 523.

A moveable magnet device 524 can position a magnet near reaction chamber 523 to collect paramagnetic beads to the surface of the reaction chamber 523 or retract a magnet to release paramagnetic beads as required. A magnetic separation (He J. et. al. J Pharm Biomed Anal. 2014; 101:84-101.) can be used to change the buffer in a reaction, to remove residual traces of emulsion oil or breaking solution, to remove an enzyme, to concentrate a product, or to capture nucleic acid or other components onto beads for ease of handling. The surface chemistries of the paramagnetic beads and conditions to precipitate, wash, and elute nucleic acids and other biomolecules onto surfaces is well understood, (Boom, W. R. et. al. U.S. Pat. No. 5,234,809. Aug. 10, 1993.), (Reeve, M. and P. Robinson. U.S. Pat. No. 5,665, 554. Sep. 9, 1997.), (Hawkins, T. U.S. Pat. No. 5,898,071. Apr. 27, 1999.), (McKernan, K. et. al. U.S. Pat. No. 6,534, 262. Mar. 18, 2003.), (Han, Z. U.S. Pat. No. 8,536,322. Sep.

17, 2013.), (Dressman et al., "Transforming single DNA molecules into fluorescent magnetic particles for detection and enumeration of genetic variation" Proc. Natl. Acad. Sci. 100(15):8817-8822 (2003)), (Ghadessy et al., "Directed evolution of polymerase function by compartmentalized self-replication", Proc. Natl. Acad. Sci. 98(8):4552-4557 (2000)), (Tawfik and Griffiths, "Man-made cell-like compartments for molecular evolution" Nat. Biotech. 16(7):652-656 (1998)), (Williams et al., "Amplification of complex gene libraries by emulsion FOR" Nat. Meth. 3(7):545-550 (2006)), and many chemistries are possible and within the scope of the instant disclosure for spatial analysis. When the nucleic acids and other biomolecules are covalent or otherwise attached to a paramagnetic bead, the beads and attached biomolecules can be separated from solution without the additive of a precipitation solution such as a crowding agent, e.g., polyethylene glycol, ethanol, etc. If the biomolecules are not attached to paramagnetic beads, reagent rail 501 can add the appropriate precipitation solution(s) to reaction chamber 523 to force the biomolecule of interest onto the surface of the paramagnetic bead.

A magnetic separation can be performed using moveable magnet device 524 to position a magnet near reaction chamber 523 to collect the paramagnetic beads to a surface of reaction chamber 523 and the reaction mix pumped to waste line 526. A wash solution, such as 80% ethanol, is added by reagent rail 501 and the beads released by retracting the magnet. In some embodiments, the wash solution can include Triton X-100 (Octylphenol ethylene oxide condensate). In some embodiments, the wash solution can include about 0.01% to about 5% Triton X-100. In some embodiments, the wash solution can include about 0.05% to about 1% Triton-X. In some embodiments, the wash solution can include Tris-HCl or Tris-EDTA. The beads can be agitated by pumping, magnetic stirrers, bubbling air, or other methods. The beads are recaptured by using moveable magnet device 524 to position a magnet near reaction chamber 523 to collect the paramagnetic beads to a surface of the reaction chamber 523 and the wash solution pumped to waste line 526. This can be repeated with the same or different wash solutions as needed to purify the reaction products, to remove unincorporated reactants, to remove emulsion oil or breaking solution, or other reasons. The biomolecule of interest can be associated with the bead or with the solution phase as desired. In addition, reaction chamber 523 can be heated to activate or inactivate enzymes. As is obvious to one skilled in the art, other devices and functionality can be added to reaction device 520 including a centrifuge device or a pipetting device.

In some embodiments, the nanodroplet or bolus generation was performed with a reversible gelling agent such as ultra low gelling agarose as taught by Geng T. et. al. Anal Chem. 2014; 86(1):703-12. In a preferred workflow, low melting agarose is added to the microsample before nozzle 429 and nanodroplets are produced with at times a single cell and a single barcoded bead with the cells compartmentalized within nanoliter agarose droplets. The nanoliter agarose droplets are transformed into microgels by cooling. The agarose microgels allow small molecules to diffuse into and out of the nanodroplets but retains macromolecules such as DNA. This enables lysis and removal of PCR inhibitors and PCR amplification (as taught by Geng T. and R. A. Mathies Forensic Sci Int Genet. 2015 January; 14:203-9).

The utility of the nanoliter agarose droplets can be further extended in the instant disclosure to couple multiple reactions in a row. As needed, the microgels can be harvested and reagents infused. The substrates and enzymes can be changed between reactions, such as a DNA library construction; see "Library Preparation for Double-Stranded DNA example." In one example, spatial analysis of polyadenylated mRNA from single cells and tissue can be performed in nanoliter agarose droplets by lysing cells, capturing mRNA, reverse transcriptase, followed by second strand synthesis. In another embodiment, precipitation agents are diffused into the nanoliter agarose droplets to force precipitation for separations onto the bead inside the nanoliter agarose droplets if the biomolecule of interest is not attached to the bead. Unbound materials can diffuse out.

c. Spatial Encoding by Adding Internal Markers or Standards Directly to the Specimen In another preferred embodiment, markers, comprised of internal markers, standards, nucleic acids, enzymes, chemicals such as isotopes, mass tags, or ratios or mixtures of enzymes, fluorescent markers, Raman markers, optical markers, carbohydrates, lipids, other biomolecules, or chemicals, are added to the specimen in known order by dispensers 335 on the multifunctional head 330 or alternatively by direct transfer from prefabricated arrays 900 of markers 901 on a support carrier, backing surface or membrane (see FIG. 17) attached to and manuevered by the multifunctional head 330. The markers are later analyzed to decode the spatial position in the specimen of the microsample 125. In some embodiments, the decoding can be an orthogonal method to the analytic method for the analyte of interest, i.e., a DNA marker could be used to decode spatial information while the sample analysis might be by mass spectrometry. In some embodiments, the markers are attached to antibodies or other bioaffinity agents such as to exterior cell surface epitopes. In other embodiments, the markers are attached to motifs, compounds, or structures that are transported, electroporated, or otherwise enter into the cells. The markers can be used to identify the spatial position of the microsample 125 and cell for many different types of analyses comprising metabolic characterization and profiling, proteomics, genomics, gene expression, carbohydrate characterization and profiling, lipid characterization and profiling, and combinations of analyses.

Figure 17:
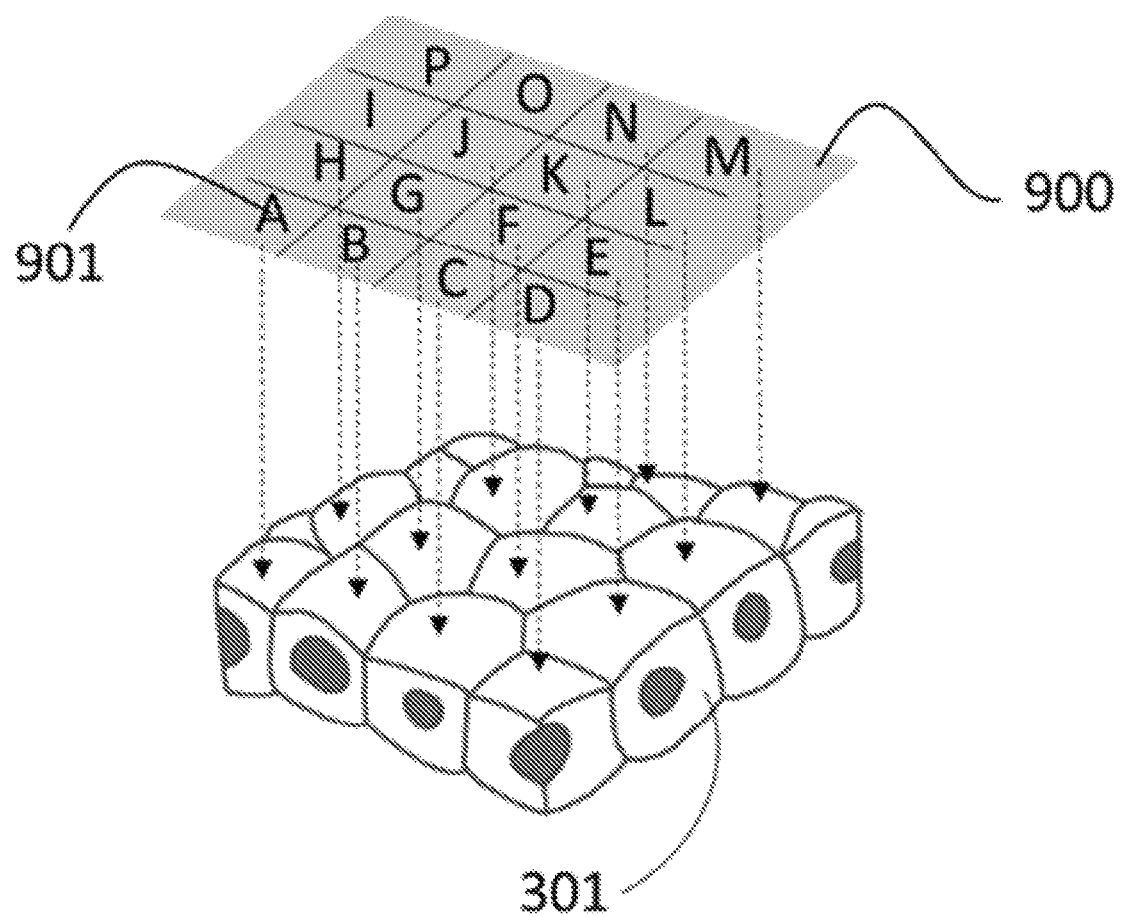
FIG. 17 shows the direct transfer of spatial markers from an array onto the specimen.

Referring to FIG. 17, the markers depicted by letters A to P are each unique and arranged in patches 901 to form a two dimensional array 900. These markers can be physisorbed as mono- or multilayers onto the surface of a membrane or support material which is connected to the multifunctional head 330. Alternatively, the markers can be arrayed in form of beads or contained in micro/nanowell architectures, or immersed in hydrogels or other surfaces 660 or structures. During sampling the array is brought into direct contact with the specimen 301 resulting in the transfer of marker reagents onto the topmost layer of the specimen thereby encoding the spatial order information directly onto the cells. It is understood that the patch-to-cell registry shown in FIG. 17 is an idealized version. It is more likely that in certain cases multiple adjacent markers will be transferred to the same cell or one marker will be transferred to multiple adjacent cells which can be used to further define boundaries between patches.

For spatial analysis of proteins, a dispenser(s) 335 or array 900 on the multifunctional head 330 can apply different solutions of markers to each microsample 125 on the specimen. For example, mass isotopes or ratios of mass isotopes can be added, and, after microsample 125 is processed in the Spatial Sampler 300 to produce single cells, the isotopes can be determined by mass spectrometry to determine where in the sample the cell or cells originated. In other embodiments, the markers are added as barcodes in the Spatial Encoder module 400.

For nucleic acid analysis, nucleic acids or other markers can be added to the specimen in known order by dispensers 335 or an array 900 on the multifunctional head 330. The nucleic acids can be electroporated into the specimen by addition of suitable electrodes and buffer, applied to the surface, or designed to be uptaken by the cells. Nucleic acid sequences can be added that are not found in the organisms being studied and their signature used to decode the spatial position of microsample 125. In some embodiments, an affinity label, such as biotin, can be attached to the nucleic acid marker and the mating affinity label, such as streptavidin, attached to beads 630 to capture the nucleic acid marker after lysis.

The following details one embodiment to add spatial barcodes to the specimen 301 directly on sampling in the Spatial Sampler module 300.

One embodiment uses a physical array of paramagnetic beads that are pre-arrayed on a Collection multifunctional head 330 with positional information encoded in the primers attached to the beads with oligonucleotides with spatial barcodes 680. This approach greatly simplifies engineering approaches for the Single Cell Spatial Analysis System 100. The Spatial Sampler module 300 uses the two-dimensional stage 320 with a multifunctional head 330. Fluidic dispensers 335 first applies solution(s) to tissue to dissolve intercellular adhesion.

Figure 18:
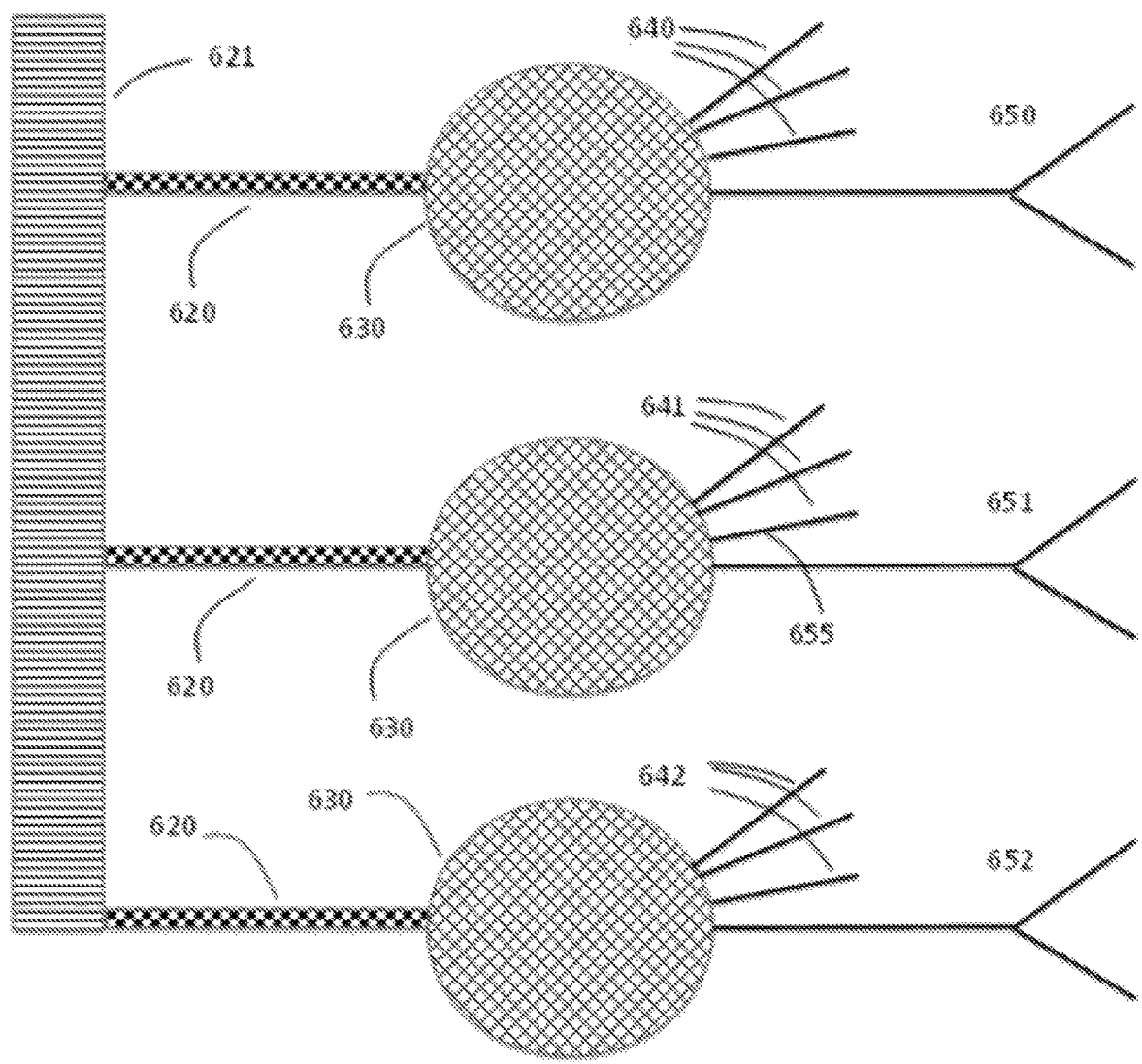
FIG. 18 shows an array of beads with known spatial barcodes and antibodies against cell surface markers attached to a surface.

In this embodiment, the transfer membrane 336 is replaced with a collection head that has an array 900 of paramagnetic beads 630 each with a single spatial barcode and in a known order. Referring to FIG. 18, the beads can be attached by cleavable linker 620 to backing surface 621, alternatively held by magnets located behind backing surface 621 or arrayed and attached by other methods. In one embodiment, each bead can have two types of biologicals attached: antibodies to binding cell surface markers 651, 652, and 653 which can all be the same or different and each individual bead has a DNA oligonucleotide with a unique spatial barcode 640, 641, and 642, and optional barcodes for cellular identity and molecular identity, and other elements comprised of sequencing primer, poly T sequence when capturing polyadenylated mRNA, targeted capture sequence, or other elements. Each bead has a different spatial barcode marker and is placed in a known order upon backing surface 621. Decoding the spatial barcode in turn allows the sequenced DNA or RNA to be traced back to its original location in the specimen.

In this embodiment, to collect cells, after dissolution of the extracellular matrix and intercellular adhesion, the collection head with backing surface 621 of the multifunctional head 330 is pressed against the top layer of the tissue and cells bound to the beads by antibodies 651, 652, and 653. To dispense, the multifunctional head 330 is moved to the cell input port of the Spatial Encoder module 300 and the linkers cleaved (or the magnet removed) to deposit all of the beads into the input port simultaneously or in groups, with gas pressure applied if needed. Individual portions do not need to be dispensed because the spatial barcode on the beads, which are attached to the cells through the antibody, can be used to decode the position of the microsample 125 after amplification. This embodiment obviates the need for spatial barcode reagent rail 401 to add spatially barcoded beads to the microsamples 125. However, this approach requires a more complicated manufacturing process to generate the arrays of spatially encoded beads.

d. Spatial Data Analysis, Representation and Information Description

The Single Cell Spatial Analysis System 100 encodes the physical location of microsamples 125 within the specimen 301 to produce spatially encoded single cells 1000. Following analysis method 1100, such as DNA sequencing, mass spectrometry, Raman spectroscopy, or other analytical methods, single cell analytical data 1600 is produced of analytes of interest, such as DNA sequence of target sequences, and at the same time the encoded spatial information from each sequence can be decoded to produce decoded single cell spatial information 1500 which identifies the spatial position 130 where microsample 125 originated in specimen 301. The decoded single cell spatial information 1500 can be, for example, 5 nucleotides or ratios of isotopes, or other decoding of markers.

The single cell analytical data 1600 is analyzed by single cell spatial analysis 2000 software to produce single cell spatial information 3000 which has the analytical data and associated physical position information of the microsample 125. For single cell spatial analysis 2000, scripts can sort reads by the spatial barcode 607 and reconstruct, for example, the DNA sequence or expression patterns from individual cells from the specimen by position in three dimensions. Types of cells, activity, gene expression, mutation, networks of genes, and expression patterns can be mapped to two or three dimensional spatial coordinates. Information from optical or other measured properties can be combined and represented visually with two and three dimensional plots of the origin of the microsample and the activity measured, genomic, proteomic, metabolomics, systems biology, etc.

The data analysis can build upon existing analytic platforms. For example, downstream (N)NGS workflow can use existing (N)NGS sequencing analysis and bioinformatics. For the bioinformatics pipeline, the quality of the data is assessed and, optionally, the reads trimmed and those with poor quality filtered out. High quality reads are aligned to the reference genome or transcriptome using one of the many available high-throughput sequencing mapping tools. Alignments are assembled into full-length transcripts or contigs based on a reference genome. For gene expression, the aligned reads are subsequently passed to quantification tools to obtain a measure of expression. After the completion of these main steps, several differential analyses can be executed to identify differentially expressed genes and transcripts. For all reads, the spatial barcode 607 information in either the same analysis or an orthogonal analysis are used to decode the origin of the same and provide input into the creation of single cell spatial information 3000, which combines single cell analytical data with the spatial data.

e. Examples of Workflows and Applications

Many applications are enabled by the Single Cell Spatial Analysis System 100. The capability of analyzing the identity, genetic sequence, gene expression, proteomic and metabolomic profiles of specimens and how groups of cells function in three dimensional matrices can be applied to forensics, molecular diagnostics, pathology, cell biology, cell discovery, histology and many other applied areas to understanding of how tissue functions. Spatial analysis of tissue at the single cell level will provide extraordinary insight and understanding, tissue composition of different cell types, structure, and how cells function in a microenvironment. Animal, plant, and microbial communities, such as biomes and films, will be important applications and how biomes change at interfaces of different organs and microenvironments. The Single Cell Spatial Analysis System 100 can be applied to molecular diagnostics where spatial analysis of biopsies can provide information about the state of the tissue, subregions 150 of activity, such as cancerous growths, and sources of qualified material for treatment; many raw and processed samples can be addressed including blood, forensic samples, tissue samples, fine needle aspirates and many others. In many of examples, the production of single cells with spatial barcodes is discussed. It will be clear to one skilled in the art that ensemble measurements of groups of cells with the same spatial barcodes, such as for a microsample 125, is within the scope of the present disclosure.

Examples are discussed in the following sections. Many other permutations, workflows, modules, devices, and combinations are possible. The names of the modules and subsystems are not limiting and functionality can be distributed differently between modules.

i. Example: Spatial Analysis of Polyadenylated mRNA from Single Cells and Tissue.

mRNA analysis from single cells has been developed and working conditions based upon the pioneering works of Macosko E. Z. et. al. Cell. 2015; 161(5):1202-14 and Klein A. M. et. al. Cell. 2015; 161(5):1187-201 and others cited therein are incorporated by reference, including instrumentation, chemistry, workflows, reactions conditions, flowcell design, and other teachings. However, no information about where in the specimen the cells originated is encoded with current methods and therefore all spatial information about the cell's physical position in the specimen and the identity of cells located near each cell are lost. The instant disclosure encodes the spatial position 130 to allow increased understanding of the identity of each cell, its state of gene expression, and the network of interactions in specimen 301 to be better understood.

Figure 19:
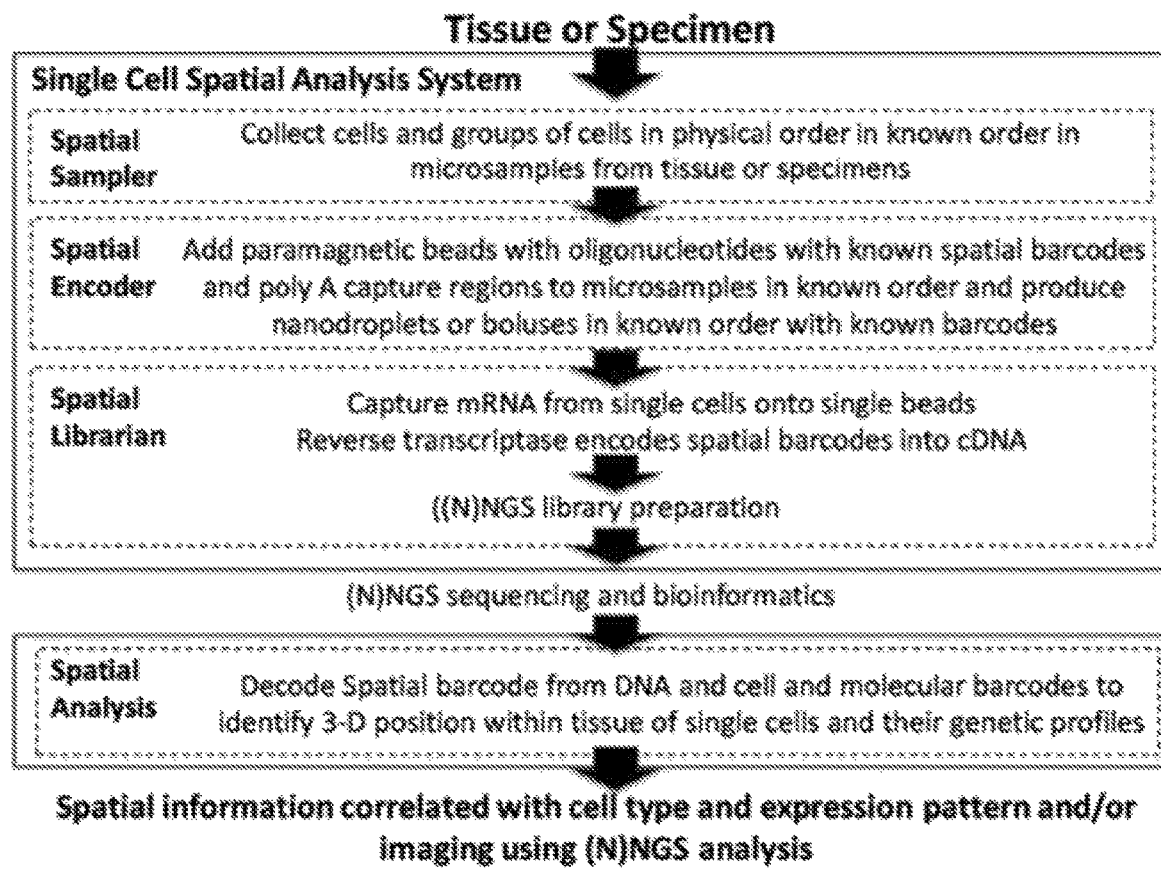
FIG. 19 shows an example workflow encoding spatial information into DNA from polyadenylated mRNA.

A preferred workflow for mRNA to encode spatial position of the microsample 125 into DNA is shown in FIG. 19. The workflow begins with sampling from tissue or other specimens 301 to collect microsamples 125, i.e., cells and groups of cells, in known physical order, one layer at a time; the layer can be a single layer of cells or multiple layers of cells. In a preferred embodiment, the microsample 125 is then input into a fluidic flow system in known order in the Spatial Sampler module 300. After the spatially encoded bead(s) has been added in the Spatial Encoder module 400, the microsample 125 and beads pass through nozzle 429 which then generates nanodroplets or small boluses each with preferably a single bead and one or less cells. In the Spatial Librarian Subsystem 500 the cells are lyzed, and the released mRNA captured onto the barcoded oligonucleotide on the bead 680. A reverse transcription reaction is performed either in the bolus or after pooling nanodroplets or boluses. The reverse transcription reaction uses the oligonucleotide as a primer and synthesizes complementary DNA (cDNA) to the mRNA sequence attached to one strand of the spatial encoded oligonucleotide, thereby covalently linking the cDNA to the DNA of the oligonucleotide. Since the oligonucleotide contains a spatial barcode, the cDNA now has a spatial barcode which can be read out by DNA sequencing after library preparation.

In other embodiments, the microsample 125 can be output into a well such as a microtiter plate or test tube, or into a flow cell, or other ordered substrate in known order from the Spatial Sampler module 300. In a preferred embodiment, a spatially encoded bead or set of beads all with the same spatial barcode is added to the microsample 125 or to single cells or groups of cells from the microsample 125. Alternatively, the spatial encoding can be on nucleic acid attached to the surface of a flowcell, or on a hydrogel, or on the interior of a capillary or microchannel, or other surfaces or matrices; these alternatives are all within the scope of the present disclosure when the term bead is used.

Figure 20:
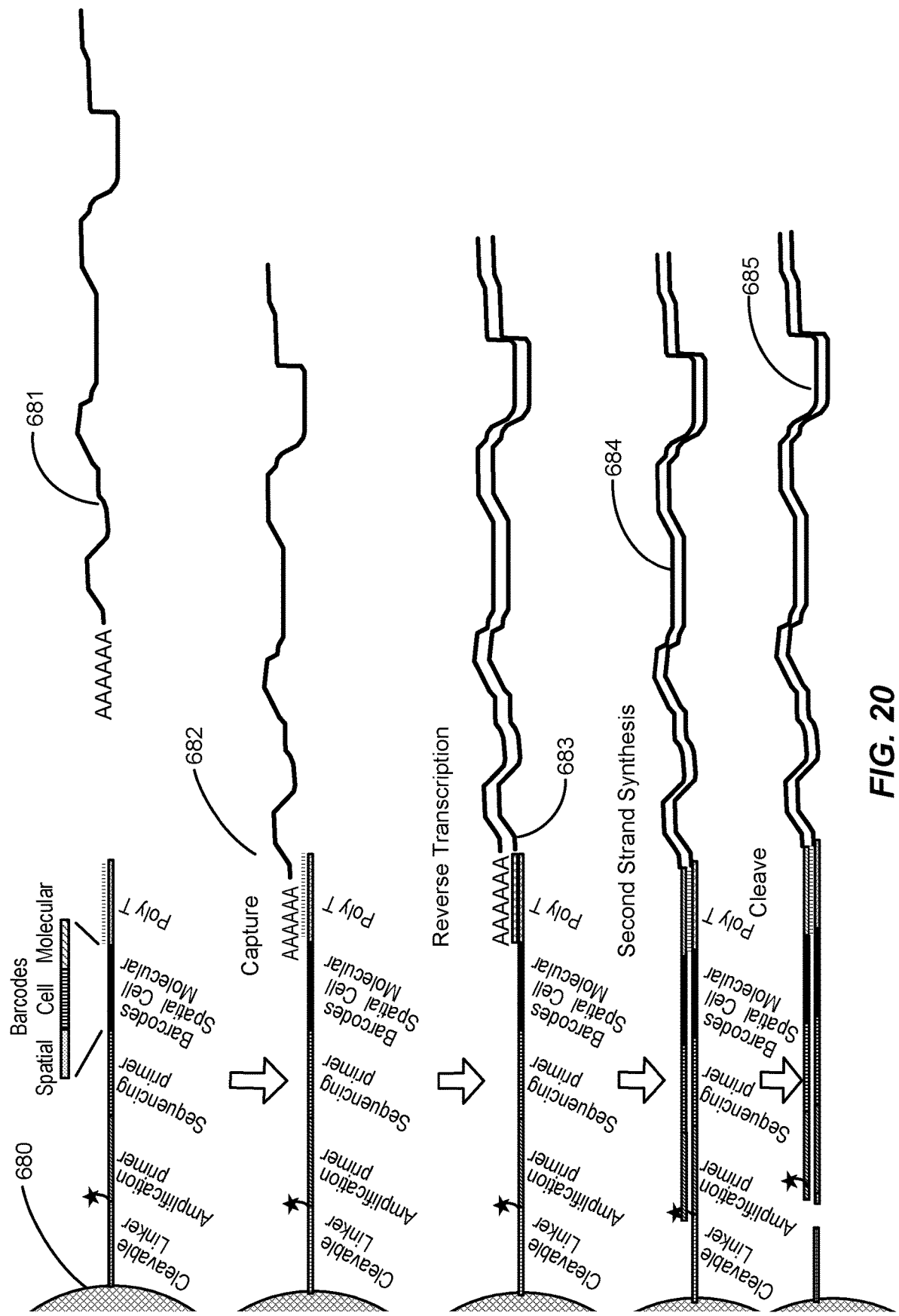
FIG. 20 illustrates the capture and molecular biology to encode spatial information into DNA from polyadenylated mRNA.

A preferred embodiment for spatial analysis of mRNA is described in more detail. In one embodiment, single channel fluidics are used. Referring to FIG. 20, a bolus of 100 nL of spatially barcoded oligonucleotide-functionalized beads 680 with a poly T sequence as the capture region 610 with a single spatial barcode is added in junction 414 to 100 nL of microsample 125 from spatial sampler output microchannel 386 and lysis/reverse transcriptase mix added separately through spatial encoder reagent syringe pump 418 and reagent connecting microchannel 419; the lysis conditions and reverse transcriptase described by (Fekete R. A. and A. Nguyen. U.S. Pat. No. 8,288,106. Oct. 16, 2012) are incorporated by reference. Monodisperse nanodroplets from single cells with spatially coded beads with lysis/RT mix, are produced using a nozzle 429 (Macosko E. Z. et. al. Cell. 2015; 161(5):1202-14.) (Klein A. M. et. al. Cell. 2015; 161(5):1187-201.) (Geng T. et. al. Anal Chem. 2014; 86(1): 703-12) and output through spatial encoder output microchannel 430.

After processing with the Spatial Preparation Subsystem with spatially barcoded oligonucleotide-functionalized beads 680 with a poly T sequence at capture region 610, the nanodroplets or boluses with a distribution of beads and single cells can be input in the Spatial Librarian Subsystem 500. Cells are lysed by heating or other methods and polyadenylated mRNA 681 captured onto the oligonucleotide to form captured mRNA structure 682. The oligonucleotides 601 are barcoded for spatial barcode information 607 as well as cellular barcodes 608 and molecule barcodes 609. Amplification primer 604 and sequencing primer 605 may be included on the oligonucleotide, or may be added in downstream library preparation methods as needed. The amplification primers can be for T7 polymerase for amplified RNA production (Van Gelder R. N. et. al. Proc Natl Acad Sci U S A. 1990; 87(5):1663-7.), PCR, rolling circle transcription-based amplification, rapid amplification of cDNA ends, continuous flow amplification, and other amplification methods.

After lysis and capture of the mRNA onto the poly T, a reverse transcriptase reaction is performed in Library Preparation Module 500 to produce cDNA attached to bead 683, formed from the mRNA, and now containing spatial, cellular, and molecular barcodes in addition to any sequencing and amplification primers and is attached to the bead 680 through a cleavable linker. Cleavage of the linker can release the cDNA from the bead when desired. A photocleavable or chemical cleavable linker and fluorescent tag(s) to aid in quality control and process development is included in the instant disclosure. As required, fragmentation of the RNA or cDNA can be performed using methods comprised of chemical, biochemical, and physical methods.

The reverse transcription reactions can be assayed by qPCR using reagents added from spatial librarian reagent rail 501 to reaction chamber 523 with thermal cycling from temperature control device 521 with optic device 522 monitoring the qPCR reaction. cDNA produced by cleaving the fluorescently tagged cDNA can be analyzed by QC device 525 with capillary electrophoresis. External polyadenylated transcripts 250-2,000 nt in length at a $10^6$ range of concentrations can be added from spatial librarian reagent rail 501 to assess the dynamic range and range of detection with NGS analysis (ERCC RNA Spike in Controls, 4456740, Life Technology).

Alternative preferred embodiments include performing an RNA ligase reaction to covalently join the mRNA to one strand of the double stranded oligonucleotide after lysis and capture of the mRNA onto spatially barcoded oligonucleotide-functionalized beads 680 with a poly T sequence as the capture region 610, or ligating RNA to a single stranded RNA or DNA attached to the bead.

In some embodiments, the emulsion is broken at this stage in a demulsification step. The emulsion can be broken, for example by heating the mixture, acidification, centrifugation and ultrasonic treatment. When nanoliter agarose droplets are used, the solidified nanoliter agarose droplets can be separated from the oil with a filter, e.g., a 40 µm or other pore size filter, incorporated into reaction chamber 523 and washed with water or solvents from spatial librarian reagent rail 501. The agarose can be melted when required to release the bead with spatial information encoded. When nanoliter aqueous droplets or boluses are used, the demulsification can be performed in the reaction chamber 523 or in some embodiments externally using chemistry and process flows as known to the skilled artisan (Kasinskas, R. et. al. WO 2012138926 A1) (Xu, M. et. al. J. Gen. Eng. Biotech. 10, 239-245, 2012) including adding solvents, aqueous solutions, non-aqueous solutions, boluses of aqueous solutions interspersed with non-aqueous solutions, while using magnetic separations, filters, membranes, charge, or other properties, to retain the spatially encoded beads while the emulsification agents are removed. Multiple solutions can be added in appropriate order.

In some embodiments, nanoliter droplets or boluses are broken and then new nanodroplets or boluses are created for a second time preferably with a single bead in each nanoliter droplet or bolus in an emulsification agent.

Following cDNA synthesis, the reverse transcriptase can be heat inactivated and/or depending on the downstream chemistries, the cDNA bound to the bead can be purified by magnetic separation, when paramagnetic beads are used, to remove inactive reverse transcriptase and change buffers and purify double stranded cDNA attached to bead 684.

Second strand synthesis of DNA can be performed by adding second strand synthesis reaction mix and DNA polymerase or enzyme mix in appropriate volumes to reaction chamber 523 from spatial librarian reagent rail 501 and incubating the reaction to produce double stranded cDNA attached to bead 684. For example, NEBNext Second Strand Synthesis Reaction Buffer and NEBNext Second Strand Synthesis Enzyme Mix NEB #E6111S may be used with incubation at 16° C. for 2.5 hr. A magnetic separation can be used to purify the double stranded DNA and remove reactants and enzymes. Double stranded cDNA attached to bead 684 can be processed in downstream library preparation for double stranded DNA, as per the section 'Library Preparation for Double-Stranded DNA example' and other methods of preparing NGS and (N)NGS sequencing libraries either in the Spatial Librarian subsystem 500 or externally.

The cleavable linker can be cleaved if desired to produce double stranded cDNA released from the bead 685 from double stranded cDNA attached to bead 684 or to produce cDNA attached to bead 682. The double-stranded DNA released from the bead 685 is ready for quality control and may include a fluorescent or other tag.

ii. Library Preparation for Double-Stranded DNA Example.

Double-stranded DNA can be prepared into a library ready for amplification and (N)NGS sequencing. The double stranded DNA can be attached to a paramagnetic bead through an oligonucleotide or double stranded DNA in solution can be used with addition of paramagnetic beads.

Figure 21:
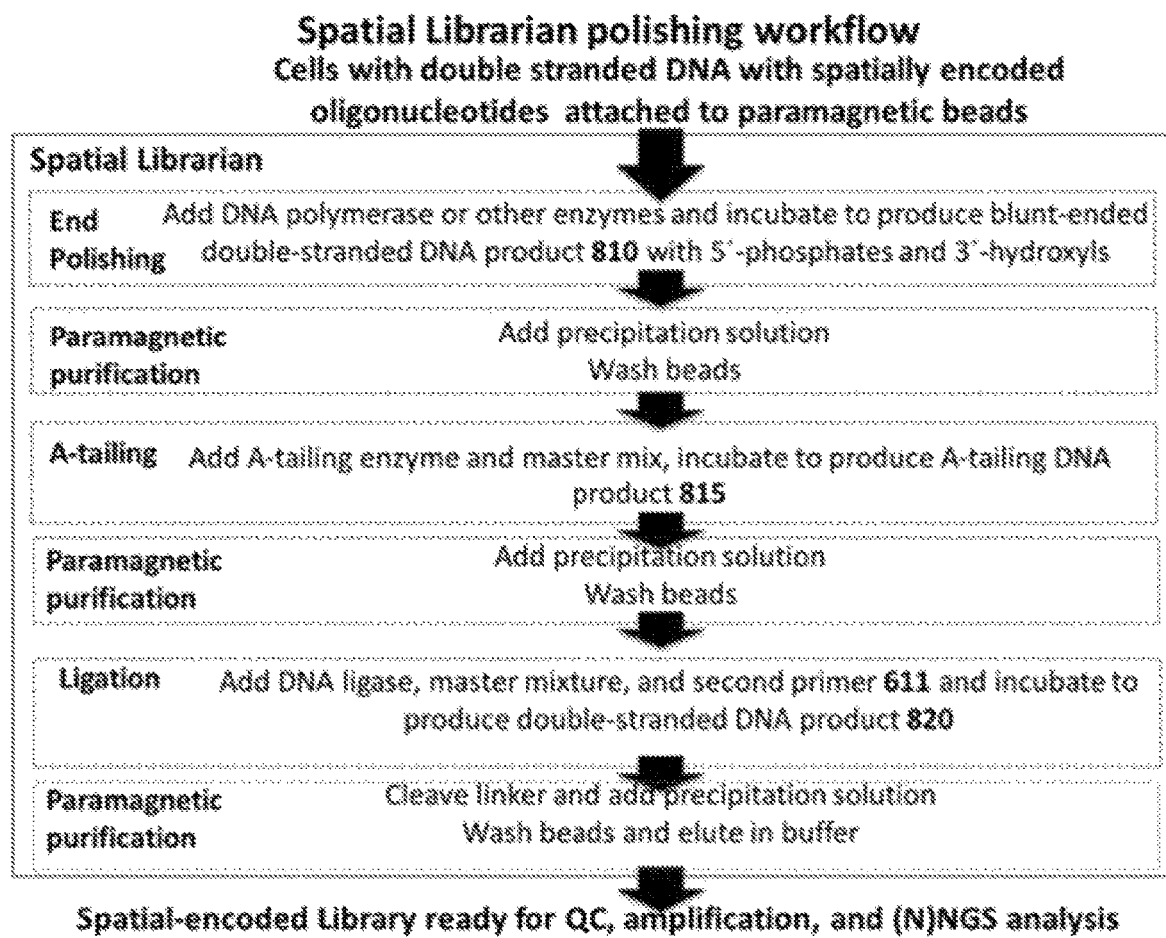
FIG. 21 shows an example workflow of library preparation from spatially encoded double stranded DNA.

One embodiment of the workflow is illustrated in FIG. 21. Double-stranded DNA attached to a bead, such as double stranded cDNA attached to bead 684, can be end-polished in reaction chamber 523 by addition of reaction mix and enzymes, for example, the NEBNext® End Repair Module (NEB E 6050S) reagents, from reaction rail 501 to generate end-polished DNA product 810, an end-polished, blunt-ended double-stranded DNA having 5'-phosphates and 3'-hydroxyls; other kits such as Agilent PCR polishing kit 200409 and other enzymology can perform the same function. Following end polishing, a magnetic separation is performed in reaction chamber 523 to remove reactants and enzymes from end-polished DNA product 810.

Following polishing, A-tailing is used to generate fragments ready to ligate with a primer with a complementary T overhang and to prevent concatamer formation during ligation. A-tailing can be performed using commercially available kits such as the NEBNext® dA-Tailing Module (NEB E6053S) with enzyme and master mix added from the spatial librarian reagent rail 501 to reaction chamber 523 containing end-polished DNA product 810 and incubating the reaction to produce blunt-ended double-stranded DNA having 5'-phosphates with an A residue overhang on the 3' end, A-tailing DNA product 815. Following A tailing, a magnetic separation is performed in reaction chamber 523 to remove reactants and enzymes from A-tailing DNA product 815.

A double stranded second primer 611 with a complementary T overhang can be ligated by DNA ligase onto the 3' end of A-tailing DNA product 815 which in some embodiments is attached to a bead or surface 660. DNA ligase, DNA ligase reaction mix, and second primer 611 are added from spatial librarian reagent rail 501 to reaction chamber 523 and incubating the reaction. DNA ligation can be performed using commercially available kits or reactions, e.g. NEBNext® Quick Ligation Module, NEB E6056S. Following DNA ligation, a magnetic separation is performed in reaction chamber 523 to remove reactants and enzymes. The product is now a double stranded DNA product 820 that has incorporated on one end the oligonucleotide 601, which can still be attached to bead 630, and the other end has incorporated second sequencing primer 611. Oligonucleotide 601 can have a cleavable linker 602, attached to an amplification primer 604 with fluorescent label 603, a sequencing primer 605, barcode region 606, and capture region 610 and other functionality such as affinity tags, e.g., biotin and others as described in Uhlén, M. BioTechniques. 2008. 44:649-654. The barcode region is comprised of a spatial barcode 607, cellular barcode 608, and molecular barcode 609.

Second primer 611 can contain functionality comprising a second sequencing primer 612, second barcode region 613, second amplification primer 614, and additionality functionality such as affinity tags.

In one embodiment of the present instant disclosure, the double stranded DNA product 820 is attached to beads and then released by cleavage of cleavable linker 602 and eluted with water, buffer, or other liquids while magnets hold the paramagnetic beads to produce double stranded DNA product in solution 830. This further purifies the double stranded DNA product in solution 830 which can be output for analysis with NGS, NNGS, nanopore, electrochemical, Sanger sequencing, single molecule sequencing, or other genetic analysis systems. If a fluorescent label 603 is attached, the cleaved product can be analyzed either on the device using quality control device 525 or collected and analyzed off of the Single Cell Spatial Analysis System 100. The analysis results can be used to assess the quality and quantity of double stranded DNA product 830.

In one embodiment of the present instant disclosure, second primer 611 is attached to a bead attached to second primer 650 which may have similar or different properties such as different magnetic moment than bead 630. For example, bead attached to second primer 650 may have a different size, magnetic moment, surface coating, affinity tags, or other property(s) that allows bead attached to second primer 650 to be manipulated differently than bead or surface 630. The difference in properties can be manipulated to purify double stranded DNA product 820 which is attached to bead 650 through the second primer.

In another embodiment of the present instant disclosure, second primer 611 is attached to a surface 660. The surface can be a flow cell 670. In one embodiment, the product of the A-tailing reaction, the blunt-ended double-stranded DNA having 5'-phosphates and an A residue overhang on the 3' end, A-tailing DNA product 815, is cleaved off of the bead 630 to produce freed A-tailed DNA product 816 and introduced to a surface 660 or flow cell 670 which has second primer 611 with a T overhang bound to the surface 660 or to flow cell 670. DNA ligase and DNA ligase reaction mix are added to produce a double stranded DNA product 840 that has incorporated on one end the oligonucleotide 601 except the cleavable linker and the other end has incorporated sequencing primer 611 attached to surface 660 or flow cell 670. Oligonucleotide 601 can be comprised of amplification primer 604, fluorescent label 603, a sequencing primer 605, barcode region 606, and capture region 610 and other functionality such as affinity tags. The barcode region is comprised of a spatial barcode 607, cellular barcode 608, and molecular barcode 609.

iii. Example: Spatial Analysis for Whole and Partial Genome Sequencing from Single Cells in a Specimen.

The Single Cell Spatial Analysis System can spatially encode cellular location in specimen 301 for whole genome DNA sequencing applications by addition of spatial barcodes 607. As described in this instant disclosure, single cells and groups of cells from subregions 150 of a specimen 301 can be input as an individual microsample 125; the analysis can be using whole or partial genome sequencing.

In one preferred embodiment, referring to FIG. 22, the Spatial Sampler module 200 collects microsamples 125 from specimen 301 as described, or other embodiments. The Spatial Encoder module 400 adds beads with oligonucleotides with spatial barcodes 680 or other surfaces with spatial barcoding in known order as nanodroplets or boluses are produced in Spatial Encoder module 400. In other embodiments, spatial barcodes are added directly to the specimen as described in the "Spatial Encoding By Adding Internal Markers or Standards Directly to the Specimen Description".

The Spatial Library module 500 performs the chemistry on the nanodroplets or boluses from the microsamples 125. For example for DNA sequencing, the microdrops can be formed with cell lysis buffer such as 0.5% sodium dodecyl sulfate (SDS), 0.1 mg/mL proteinase K, 100 mM EDTA, and 10 mM Tris-HCl. After lysis, if low melting point agarose is used, the temperature can be decreased to gel the agarose and the gel droplets can be repeated washed. A restriction digest can then be performed by mixing a restriction digest buffer, for example, 100 mM potassium acetate, 25 mM Tris-acetate, pH 7.6, 10 mM magnesium acetate, 10 µg/ml BSA, 0.5 mM β-mercaptoethanol, containing a blunt end restriction enzyme or a restriction enzyme that generates an overhang with the beads. After diffusion, emulsion oil can be added and the temperature can be raised to 37° C.; the digestion of the genomic DNA will occur to produce blunt ended fragments or fragments with overhangs.

In embodiment, the oligonucleotide has a cleavable linker 602, attached to an amplification primer 604 with fluorescent label 603, a sequencing primer 605, barcode region 606, and capture region 610. In one embodiment, the capture region 610 is blunted ended while in other embodiments the capture region 610 is single-stranded to capture specific or non-specific DNA sequences. The barcode region is comprised of a spatial barcode 607, cellular barcode 608, and molecular barcode 609. In some embodiments, the molecular barcode 609 is not used. When restriction enzymes are used, the oligonucleotide on the bead can be designed to not contain the relevant restriction site.

When the agarose encapsulation is used, after restriction digest, the temperature can be lowered to gel the agarose, and after an optional rinse step(s), either DNA polymerase with appropriate reaction mixture or DNA ligase with appropriate reaction mixture is added. After diffusion of the DNA polymerase or ligase and mixture into the gelled microdroplets, emulsion oil is added and the temperature raised, for example to 37 C. DNA captured using overhangs or hybridization is replicated with a DNA polymerase to incorporate the spatial barcode 607 into the DNA strand in the microdroplet. For blunt ended capture, DNA ligase incorporates a spatial barcode 607 on a blunted ended bead with spatial barcode 680 with the ligated DNA strand in the nanodroplet, bolus, or well. The microdroplets or microsamples 125 in wells can be pooled for the remaining library preparation. For single stranded capture regions, the length of the capture region and hybridization conditions can be adjusted to tune the specificity of capture. In some cases, related sequences might be desired to be captured while in others increased specificity of capture may be desired: either can be accommodated including a plurality of capture sequences comprised of sequences that interrogate different signatures, networks, diseases including cancer, microbes, genetic traits, introns, exons, and groups of sequences without limitation.

DNA or RNA can be fragmented in the Spatial Library module by methods well known to one skilled in the art, using chemical, biochemical, or physical fragmentation when required. In one embodiment, the Spatial Librarian Subsystem 500 adds restriction enzymes to double stranded whole genome DNA to create restriction fragments with specific sequences. The restriction fragments can have an overhang that can be captured or ligated to its complementary sequence on the capture region 610 on the oligonucleotide. In another embodiment, the Spatial Librarian Subsystem 500 adds polishing reagents to fragments DNA to produce blunt ended fragments.

iv. Example: Spatial Encoding Nucleic Acids with Targeted Sequencing

The Single Cell Spatial Analysis System 100 can spatially encode where in the specimen 301 the cell was located to prepare libraries for targeted DNA sequencing. The overall workflow for one embodiment is shown in FIG. 23. Beads with oligonucleotides with spatial barcodes 680 or other surfaces 660 with spatial barcoding are used with capture region 610 designed to be complementary to the DNA sequence to be captured. In another example, an overhang such as a restriction site can be captured or ligated to its complementary sequence. The sequences to be captured can be generated by using a restriction digest mixture to form the microdroplets and then performing the digest in the microdroplets and hybridization. In another embodiment, the microdroplets are formed with fragmentase such as NEB-Next® dsDNA Fragmentase and the DNA is fragmented. The length of the capture region and hybridization conditions can be adjusted to tune the specificity of capture. In some cases, related sequences might be desired to be captured while in others increased specificity of capture may be desired: either can be accommodated. A plurality of capture sequences comprised of sequences that interrogate different signatures, networks, diseases including cancer, microbes, genetic traits, introns, exons, and groups of sequences without limitation are within the instant disclosure.

The targeted DNA captured is replicated with a DNA polymerase, e.g., phi29, Taq, or others, to incorporate spatial barcode 607 into the captured targeted DNA strand in the nanodroplet, bolus, or well. The captured DNA with the spatial barcode 607 on beads can be pooled and processed into (N)NGS libraries either in the Single Cell Spatial Analysis System or externally, with amplification when required, comprised of PCR, rolling circle amplification (RCA), Loop mediated isothermal amplification (LAMP), Helicase-dependent amplification (HDA), Nicking Enzyme Amplification Reaction (NEAR) and other methods.

v. Example: Library Preparation Using Transposons.

Libraries for (N)NGS can be prepared using tagmentation with transposons including the Nextera Tagmentation (http://www.epibio.com/docs/default-source/protocols/nextera-dna-sample-prep-kit-(illumina—compatible).pdf?sfvrsn=4). In this embodiment, referring to FIG. 24, double stranded DNA with spatial encoding attached to a bead or surface is used as the input in the Spatial Library Subsystem 500. Once the double stranded DNA is produced in reaction chamber 523, transposons, e.g., Nextera enzyme, reaction mix, and water are added from reagent rail 501. The reaction is incubated for example at 55 C for 5 min. A bead purification is performed to remove reactants and purify the double stranded product with transposon inserted 840. In the example shown in FIG. 24, precipitation agents are not added since the desired material is attached to a bead or surface; the inclusion or not of precipitation reagents is not limiting. Reagent rail 501 is used to add Nuclease-Free Water, Nextera Adaptor 2 (or other barcoded adapters), Nextera PCR Enzyme, PCR Buffer, Nextera Primer Cocktail. Nine cycles of PCR can be performed. A bead purification is performed to remove reactants and purify the double stranded DNA product 850 before elution into buffer or water. The double stranded DNA product 850 library is now ready to QC and bridge amplification on the flow cell. Many variations of the method described here are within the instant disclosure and are obvious to one skilled in the art.

Figure 24:
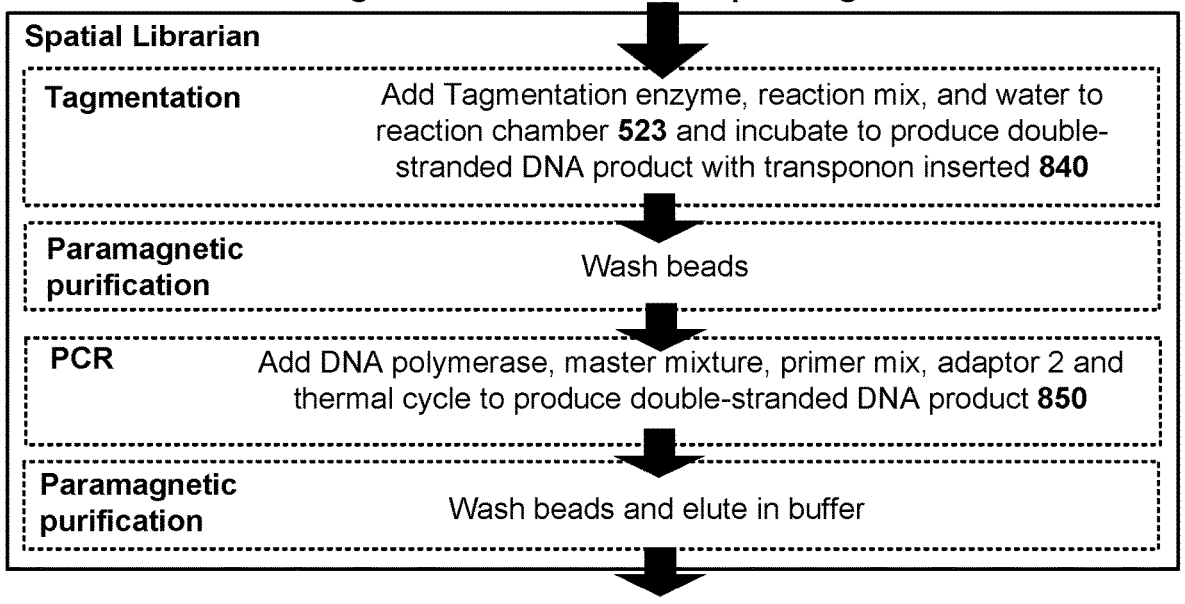
FIG. 24 shows an example of using transposons to produce a sequencing library from double stranded DNA with spatial encoding from single cells from a specimen.

In another embodiment, the double stranded DNA with a spatial barcode is attached to a flow cell 670 or surface 660. In this example, same chemistry as shown in FIG. 24 could be applied except the products are attached to the flow cell 670 and flow cell 670 is washed rather than the beads.

vi. Example: Single Cell Spatial Systems Biology

Single cell spatial analysis 1000 and its integration into a Single Cell Spatial Analysis System 100 can be applied to systems biology. Systems biology connotes the integration of two or more data streams from specimen 301, e.g., DNA sequencing with RNA sequencing; DNA and RNA sequencing with mass spectrometry for proteins, DNA sequencing with metabolomics; and other combinations without limitation. In the instant disclosure, the benefits of single cell spatial analysis 2000 include all the benefits of systems biology extended with the benefits of understanding the identity, location, activity, and interplay of single cells in a matrix such as tissue, organs, organisms, biofilms, molecular diagnostics samples, and in the environment.

1. Spatial Encoding DNA and RNA from Single Cells Simultaneously

It is frequently of interest to sequence both the DNA and RNA from single cells and in the instant disclosure with information of the spatial position 130 of microsample 125 in specimen 301. In this workflow, the paramagnetic beads can be a mixture of, for example, two types of beads with oligonucleotides with spatial barcodes 680 with a capture region 610 with one type of bead having poly T sequences and the other type sequences for targeted DNA capture. The beads can be synthesized by split pool, and mixed in the appropriate ratios.

In the workflow to spatially encode both DNA and RNA, the cells are lysed and the DNA and RNA bound by hybridization. Reverse transcription is performed to convert the bound mRNA into cDNA. Second strand synthesis can convert the cDNA to double stranded DNA and at the same time incorporate the target DNA captured to the oligonucleotide attached to the bead. The beads can then be pooled, the emulsion broken, and libraries created. On sequencing, the molecular barcodes and string of Ts or As will identify RNA products for quantitation of gene expression.

2. Simultaneous Spatial Analysis of Nucleic Acids and Other Analytes.

An alternative configuration of single cell spatial analysis 2000 is to analyze nucleic acids simultaneously with other cellular components comprised of proteins, lipid, carbohydrates, metabolites,etc. The spatial encoding can be any method including DNA analysis or by adding internal markers or standards directly to specimen 301. In a preferred embodiment, markers, e.g., internal markers, standards, nucleic acids, chemicals etc., are added to the specimen in known order by dispensers 335 on the multifunctional head 330. In some embodiment single cells from a microsample 125 with spatial barcoding are prepared as described and nanodroplets with a single cell and single bead with a single spatial barcode are produced. The sample can be processed by two analysis modulaties. For example, when polyadenylated mRNA is analyzed, after cDNA synthesis, if a magnetic separation is performed, the material unbound to the paramagnetic bead can be analyzed by a orthogonal method such as an mass spectrometry to determine proteomics and the double stranded cDNA attached to bead 684 can be used for mRNA analysis with nucleic acid decoding. One or both sets of markers can be analyzed to decode the spatial position in the specimen of the microsample 125.

In some embodiments, the decoding can be an orthogonal method to the analytic method for the analyte of interest, i.e., a DNA marker could be used to decode spatial information while the sample analysis might be by mass spectrometry. In some embodiments, the markers are attached to antibodies such as to exterior cell surface epitopes. In other embodiments, the markers are attached to motifs, compounds, or structures that are transported, electrophorated, or otherwise enter into cells. The markers can be used to identify the spatial position 130 of the microsample 125 for many different types of analyzes comprising metabolic characterisation and profiling, proteomics, genomics, gene expression, carbohydrate characterisation and profiling, lipid characterisation and profiling, and combinations of analyzes.

In some embodiments, the spatial encoding of single cells or groups of cells is only encoded with one modality. For example, single cell spatial analysis 1000 of specimen 301 can determine through nucleic acid sequencing the spatial information needed to identify the microsample 125 and individual cells. The nucleic acid sequencing provides the spatial information which can then be used even when the same sample is analyzed by a different modality, such as mass spectrometry, to provide spatial information of where the microsample 125 was in specimen 301 since the order of the barcoded microsample 125 can be tracked. In these embodiments therefore only one barcode is required for systems biology or other applications.

vii. Example: Forensics Applications

For forensics, specimens 301 can be recovered from crime scenes by tape lifts, swabs, and other collection devices from a diverse set of sample types, such as blood, semen, sputum, etc., on a diverse set of surfaces with possible mixtures of cells from different contributors. Specimen 301 can be input into the Single Cell Spatial Analysis System 100 and the pattern of cells from the two-dimensional or three-dimensional specimen analyzed by methods comprised of short tandem repeats (STRs), such as the Combined DNA Index System (CODIS) or other STR panels, for single nucleotide polymorphisms (SNPs), gene sequencing, protein profiling, and other methods. Specimen 301 can be directly contacted by a portable Single Cell Spatial Analysis System 100 or Spatial Sampling Module 300.

Single cell analysis can identify the contributors to a mixture, regardless of the number of contributors. In addition to identifying contributors to mixtures, spatial analysis retains information of the pattern of the cells which may contain important evidence about the crime and how it was reflected in the crime scene. The patterns revealed by single cell spatial analysis 1000 may show layers, edges of contact, spatter, or other information. SNP analysis with single cell spatial analysis 1000 will allow facial reconstruction of victim, suspects, and contributors (Claes P. et. al. PLoS Genet. 2014; 10(3):e1004224.) as the field continues to advance.

viii. Example: Portable Single Cell Spatial Analysis System

A portable Single Cell Spatial Analysis System 100 will enable direct sampling and single cell spatial analysis 1000 at a non-laboratory location. In one configuration of the Spatial Preparation Subsystem 200, multifunctional head 330 directly contacts specimen 301 when the specimen is a surface, material, or other two or three dimension matrix. The multifunctional head 330 enables the application of stain to the sample, for example, to identify regions with human cells at a crime scene, regions with malignant cells, live/dead, or other attributes. The appropriate subregions can be transferred by transfer membrane 336 into the Single Cell Spatial Analysis System 100 for preparation of samples for single cell spatial analysis 1000.

A portable Single Cell Spatial Analysis System 100 will enable single cell spatial analysis 1000 while the system is physically moved on its way to an analysis system. Alternatively the spatial encoded sample might be produced at the non-laboratory location and transported to an analysis system in a cartridge 4000. A sample-to-answer portable system can be produced by combining the Single Cell Spatial Analysis System 100 with a miniaturized detection system such as Oxford nanopore sequencing, a portable mass spectrometer, Raman, capillary electrophoresis, real-time PCR, or other miniaturized detection system.

f. Integration with Upstream and Downstream Analysis

The Single Cell Spatial Analysis System 100 or a portable version can be integrated with upstream specimen processing and downstream sample preparation and analysis processing in a preferred embodiment. For upstream specimen processing, that is processing before transferring any of specimen 301, the Single Cell Spatial Analysis System 100 in one embodiment adds reagents to the specimen and optionally measures attributes with optics head 331 such as fluorescence, colorimetric, Raman, Surface Enhanced Raman, or other optical properties. This upstream information can inform whether subregions 150 are of interest in the specimen and/or the workflow to be performed. In another embodiment, multifunctional head 330 has an additional sensor such that can perform electrophysiology measurements before destructive transfer of microregions 150 of specimen 301. In another embodiment, the Single Cell Spatial Analysis System 100 collects raw samples with a device that produces specimen 301 from tissue or other matrices, for example, sectioning tissue, contact transferring, or by dissolution to create microsamples 125.

In another embodiment, downstream analytical subsystems are incorporated such as a DNA sequencer, mass spectrometer, real time PCR, single molecule, capillary array electrophoresis, DNA or protein microarray, or other analytical systems. For nucleic acid analysis, a sample-to-answer system embodiment can be produced by combining a Single Cell Spatial Analysis System 100 with the Spatial Librarian subsystem 500 with a miniaturized detection system such as nanopore sequencing, capillary array electrophoresis, or real time PCR system.

What is claimed is:

1. A spatial preparation system comprising:
   a) a spatial sampler subsystem comprising:
      (1) a specimen holder comprising a plate having a flat surface, and, on the flat surface, a biological specimen comprising a tissue, and
      (2) a multifunctional head comprising a transfer head comprising a plurality of extraction channels, wherein the extraction channels comprise openings covered with one or more transfer membranes, and wherein the extraction channels are in communication with a first liquid source under positive and/or negative pressure, and wherein the multifunctional head is mounted on a three axis stage to position the multifunctional head over the specimen holder at different spatial positions; and
   b) a spatial encoder subsystem comprising:
      (1) a plurality of spatial encoder microchannels, each microchannel having an inlet, and each communicating with a common output microchannel at different first junctions;
      (2) a reagent rail comprising a plurality of containers, each container comprising different marker molecules comprising different spatial information, wherein the reagent rail communicates with the common output microchannel;
      (3) a microdroplet generator comprising a source of immiscible liquid in communication with the common output microchannel at a second junction downstream of the first junctions; and
      (4) one or more pumps communicating with the spatial encoder microchannels, the common output microchannel, the reagent rail and the source of immiscible liquid; and
   wherein:
      (1) the spatial sampler subsystem is configured:
         (i) to extract, by contact adhesion or by vacuum, a plurality of microsamples from each of a plurality of different original spatial positions on the biological specimen onto the one or more transfer membranes;

(ii) to move the multifunctional head using the stage to the inlets of the spatial encoder microchannels; and (iii) to deliver through application of positive or negative pressure, each extracted microsample to an inlet of one of the spatial encoder microchannels in a pattern based on their original spatial position in the biological specimen; and (2) the spatial encoder subsystem is configured:

(i) to move each microsample from a spatial encoder microchannel to the common output microchannel through application of positive or negative pressure;

(ii) to move different marker molecules from containers in the reagent rail into the common output microchannel through application of positive or negative pressure; and (iii) to generate microdrops in the common output channel, wherein the microdrops are spatially separated by the immiscible fluid, wherein a plurality of the microdrops comprise a microsample and a marker molecule.

2. The system of claim 1, wherein the multifunctional head further comprises a dispense head configured to dispense liquid onto the biological specimen.

3. The system of claim 1, wherein the extraction channels are arrayed in a linear array or a planar array.

4. The system of claim 1, wherein the multifunctional head comprises a gas source.

5. The system of claim 1, wherein the spatial encoder subsystem comprises:

a microsample encoder assembly comprising a plurality of reservoirs, each comprising a different spatial marker and each communicating with the spatial encoder microchannel, and, reservoirs comprising a reverse transcriptase, a polymerase or a ligase.

6. The system of claim 1, wherein the transfer membranes have attached thereto a plurality of capture elements, each capture element comprising a particle having attached thereto one or more antibodies that bind into cells in the biological specimen, and nucleic acid markers comprising positional barcodes comprising spatial information where the spatial information calling to the position of the particle on the multifunctional head.

7. The system of claim 6, wherein, the particle is paramagnetic.

8. The system of claim 6, wherein, the nucleic acid markers further comprise cell markers identifying the cell to which particle binds, and/or molecular barcodes that differently label different nucleic acid molecules and a single cell.

9. The system of claim 1, wherein the spatial sampler subsystem comprises a vacuum source that applies vacuum to the multifunctional head for extracting cells from tissue deposited on the specimen holder and a pressure source to push extracted cells from the multifunctional head.

10. The system of claim 1, wherein the spatial markers comprise oligonucleotide barcodes attached to solid supports.

11. The system of claim 2, wherein the multifunctional head comprises cell dissociation solution comprising at least one protease that digests extracellular matrix.

12. The system of claim 1, further comprising:

c) a spatial librarian subsystem configured to perform a series of biochemical reactions on an emulsion comprising microdrops produced by the spatial preparation subsystem, wherein the spatial librarian subsystem comprises:

a reaction device comprising an inlet communicating with an outlet of the common output microchannel, at least one reaction chamber, and an outlet;

a reagent rail communicating with the reaction device through a microchannel and comprising a reverse transcriptase or a polymerase and;

one or more pumps configured to move the reagents from the reagent rail through the microchannel to the reaction chamber of the reaction device.

13. The system of claim 12, wherein the spatial librarian subsystem further comprises:

a temperature controller configured to control temperature in the reaction chamber.

14. The system of claim 12, wherein the spatial librarian subsystem further comprises:

a magnet configured to reversibly immobilize paramagnetic particles contained in the reaction chamber.

15. The system of claim 12, wherein the biochemical reactions comprise at least:

(i) reverse transcription of messenger RNA into cDNA; and (ii) amplification of cDNA.

16. The system of claim 12, wherein the biochemical reactions comprise at least:

(i) primer extension of a primer hybridized to a DNA template to create an extension product; and (ii) amplification of the extension product.

17. The system of claim 2, wherein the fluid comprises an imaging reagent or dissociation solution.

18. The system of claim 1, wherein the extraction channels each comprise ends covered with an air permeable, cell impermeable transfer membrane.

19. The system of claim 18, wherein a single membrane covers the ends of the plurality of extraction channels.

20. The system of claim 1, wherein the extraction channels are arrayed in a line or a plane.

21. The system of claim 1, wherein the spatial sampler subsystem is configured to deliver each microsample to an inlet of one of the spatial encoder microchannels in one step.

* * * * *